United States Patent
Merk et al.

(10) Patent No.: US 10,463,470 B2
(45) Date of Patent: Nov. 5, 2019

(54) METHODS OF MAKING A PROSTHESIS WITH A SMOOTH COVERING

(71) Applicant: Cook Medical Technologies LLC, Bloomington, IN (US)

(72) Inventors: James C. Merk, Terre Haute, IN (US); Brent A. Mayle, Spencer, IN (US); Gary Neff, Bloomington, IN (US); Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 337 days.

(21) Appl. No.: 15/224,101

(22) Filed: Jul. 29, 2016

(65) Prior Publication Data
US 2017/0027682 A1    Feb. 2, 2017

Related U.S. Application Data

(60) Provisional application No. 62/199,764, filed on Jul. 31, 2015.

(51) Int. Cl.
*A61F 2/07*    (2013.01)
*A61F 2/915*    (2013.01)

(52) U.S. Cl.
CPC ............... *A61F 2/07* (2013.01); *A61F 2/915* (2013.01); *A61F 2002/072* (2013.01); *A61F 2002/91575* (2013.01); *A61F 2240/001* (2013.01)

(58) Field of Classification Search
CPC ................. A61F 2/07; A61F 2002/072; A61F 2002/91575; A61F 2240/001; A61F 2/915
(Continued)

(56) References Cited

U.S. PATENT DOCUMENTS

| 4,781,046 A | 11/1988 | Porowski |
| 4,955,899 A | 9/1990 | Della Corna et al. |

(Continued)

FOREIGN PATENT DOCUMENTS

| WO | WO 01/15633 A1 | 3/2001 |
| WO | WO 01/16533 A1 | 3/2001 |
| WO | WO 02/24247 A1 | 3/2002 |

OTHER PUBLICATIONS

Article titled, "Bioweb", from the Zeus website, obtained from the Internet at: http://www.zeusinc.com/advances-products/bioweb on Jul. 8, 2015, 3 pgs.

*Primary Examiner* — Sarang Afzali
*Assistant Examiner* — Darrell C Ford
(74) *Attorney, Agent, or Firm* — Brinks Gilson & Lione

(57) ABSTRACT

The present invention relates to methods of making a prosthesis or a stent with a smooth covering. The method includes providing an elastomeric tube including an inner diameter and an outer diameter, positioning the elastomeric tube in a tube expander including a vacuum, expanding the inner diameter and the outer diameters of the elastomeric tube by applying the vacuum, providing a mandrel, positioning an inner covering over the mandrel, positioning a stent over the inner covering, positioning an outer covering over the stent to form a covered stent, positioning the mandrel and the covered stent in the tube expander, releasing the vacuum, removing the elastomeric tube, the covered stent, and the mandrel form the tube expander, applying pressure and heat to the elastomeric tube, the covered stent, and the mandrel, removing the elastomeric tube, the covered stent, and the mandrel from the pressure and the heat, removing the elastomeric tube from the covered stent, and removing the mandrel from the covered stent.

19 Claims, 37 Drawing Sheets

(58) Field of Classification Search
USPC ......... 29/517, 428, 505, 506, 507, 515, 516, 29/743, 623; 623/1.13, 1.46
See application file for complete search history.

(56) References Cited

U.S. PATENT DOCUMENTS

| | | | |
|---|---|---|---|
| 5,591,222 A | 1/1997 | Susawa et al. | |
| 5,620,763 A | 4/1997 | House et al. | |
| 5,628,788 A | 5/1997 | Pinchuk | |
| 5,749,880 A | 5/1998 | Banas et al. | |
| 5,948,191 A * | 9/1999 | Solovay | A61F 2/07 156/247 |
| 7,560,006 B2 * | 7/2009 | Rakos | A61F 2/06 156/285 |
| 7,641,844 B2 | 1/2010 | Melsheimer | |
| 7,678,144 B2 | 3/2010 | Bailey et al. | |
| 7,779,261 B2 | 8/2010 | Moskowitz et al. | |
| 8,100,683 B2 | 1/2012 | Orr et al. | |
| 8,123,884 B2 | 2/2012 | Kujawski et al. | |
| 8,211,168 B2 | 7/2012 | Purdy et al. | |
| 8,257,431 B2 | 9/2012 | Henderson et al. | |
| 8,403,979 B2 | 3/2013 | Paul, Jr. | |
| 8,637,109 B2 | 1/2014 | Grewe et al. | |
| 8,696,738 B2 | 4/2014 | Noesner et al. | |
| 8,795,577 B2 | 8/2014 | Orr et al. | |
| 8,801,750 B2 | 8/2014 | Cully et al. | |
| 8,876,849 B2 | 11/2014 | Kratzberg et al. | |
| 9,060,852 B2 | 6/2015 | Grewe et al. | |
| 10,005,269 B2 * | 6/2018 | Hall | D01D 5/18 |
| 2001/0010012 A1 * | 7/2001 | Edwin | A61F 2/07 623/1.13 |
| 2006/0282147 A1 * | 12/2006 | Andreas | A61F 2/91 623/1.11 |
| 2007/0207186 A1 * | 9/2007 | Scanlon | A61F 2/07 424/424 |
| 2008/0132999 A1 * | 6/2008 | Mericle | A61F 2/07 623/1.34 |
| 2008/0157444 A1 | 7/2008 | Melsheimer | |
| 2009/0142505 A1 | 6/2009 | Orr et al. | |
| 2009/0151819 A1 * | 6/2009 | Charlebois | B23K 20/129 148/521 |
| 2009/0187240 A1 | 7/2009 | Clerc et al. | |
| 2009/0319023 A1 | 12/2009 | Hildebrand et al. | |
| 2010/0249907 A1 * | 9/2010 | Dorn | A61F 2/95 623/1.23 |
| 2010/0323052 A1 | 12/2010 | Orr et al. | |
| 2011/0054512 A1 | 3/2011 | Hendriksen et al. | |
| 2012/0065583 A1 * | 3/2012 | Serna | A61M 25/1029 604/103.02 |
| 2012/0141656 A1 | 6/2012 | Orr et al. | |
| 2012/0259170 A1 | 10/2012 | Grewe et al. | |
| 2013/0018220 A1 | 1/2013 | Vad et al. | |
| 2013/0085565 A1 | 4/2013 | Eller et al. | |
| 2013/0122248 A1 | 5/2013 | Haselby et al. | |
| 2013/0184808 A1 * | 7/2013 | Hall | D01F 6/12 623/1.22 |
| 2014/0081386 A1 | 3/2014 | Haselby et al. | |
| 2014/0188212 A1 | 7/2014 | Haselby et al. | |
| 2014/0222039 A1 * | 8/2014 | Khosrovaninejad | A61F 2/04 606/151 |
| 2014/0324149 A1 * | 10/2014 | Slattery | A61F 2/958 623/1.11 |
| 2015/0112383 A1 | 4/2015 | Sherman et al. | |
| 2019/0133747 A1 * | 5/2019 | Janardhan | A61M 29/00 |

* cited by examiner

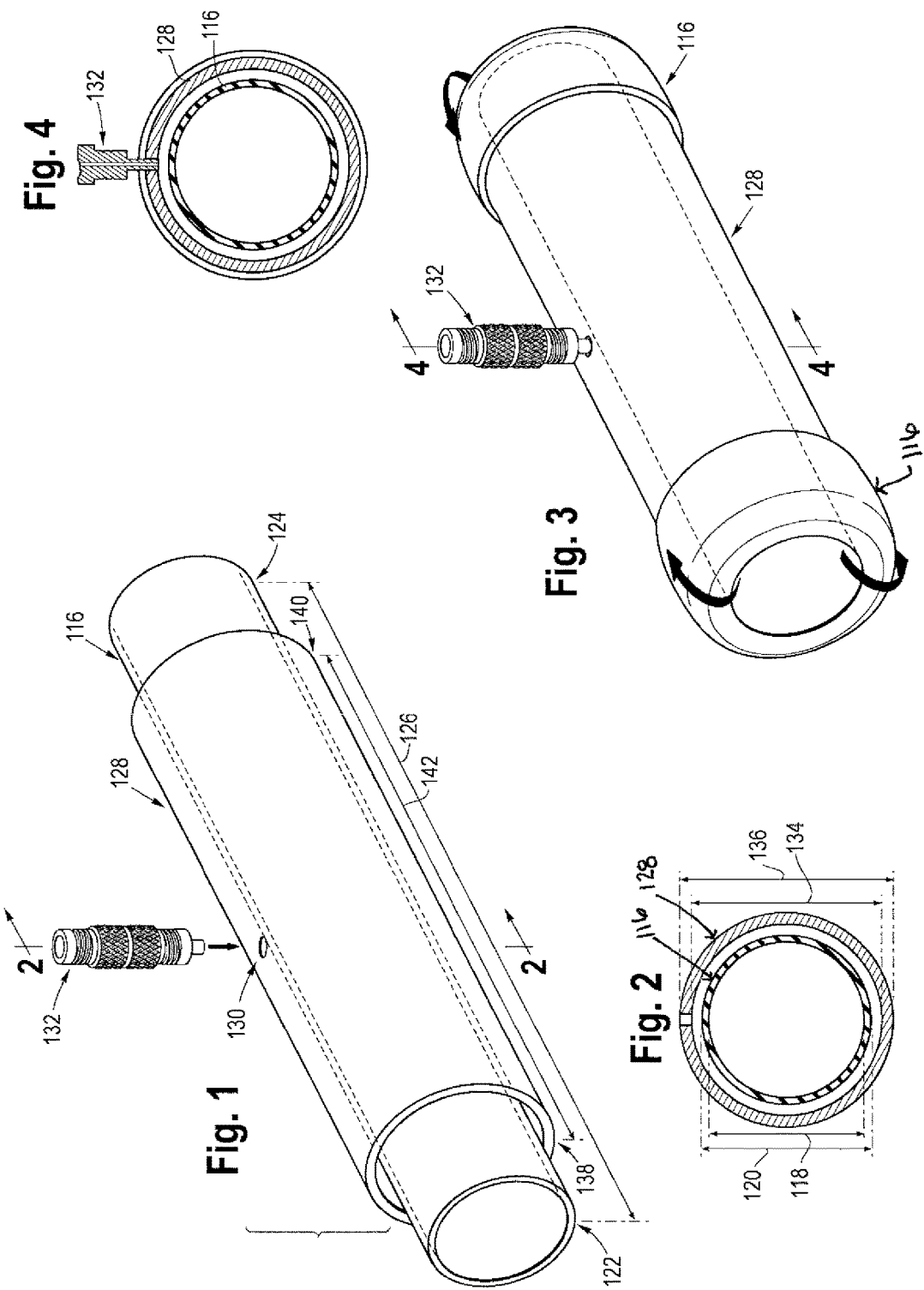

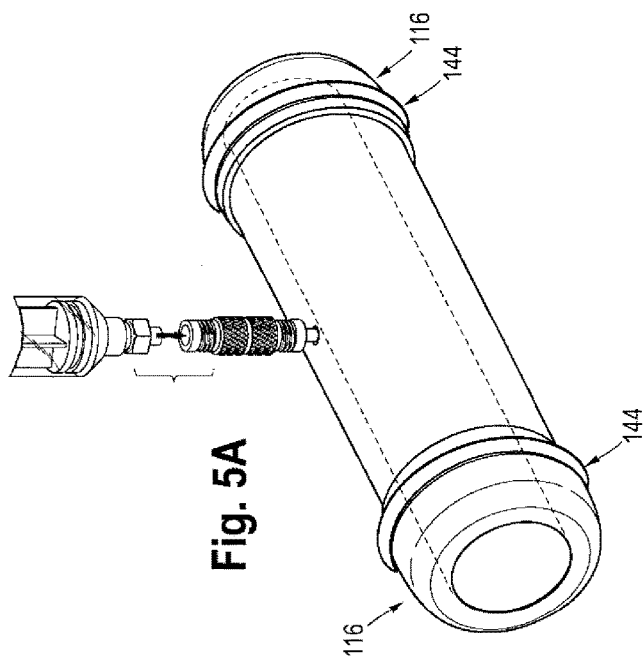
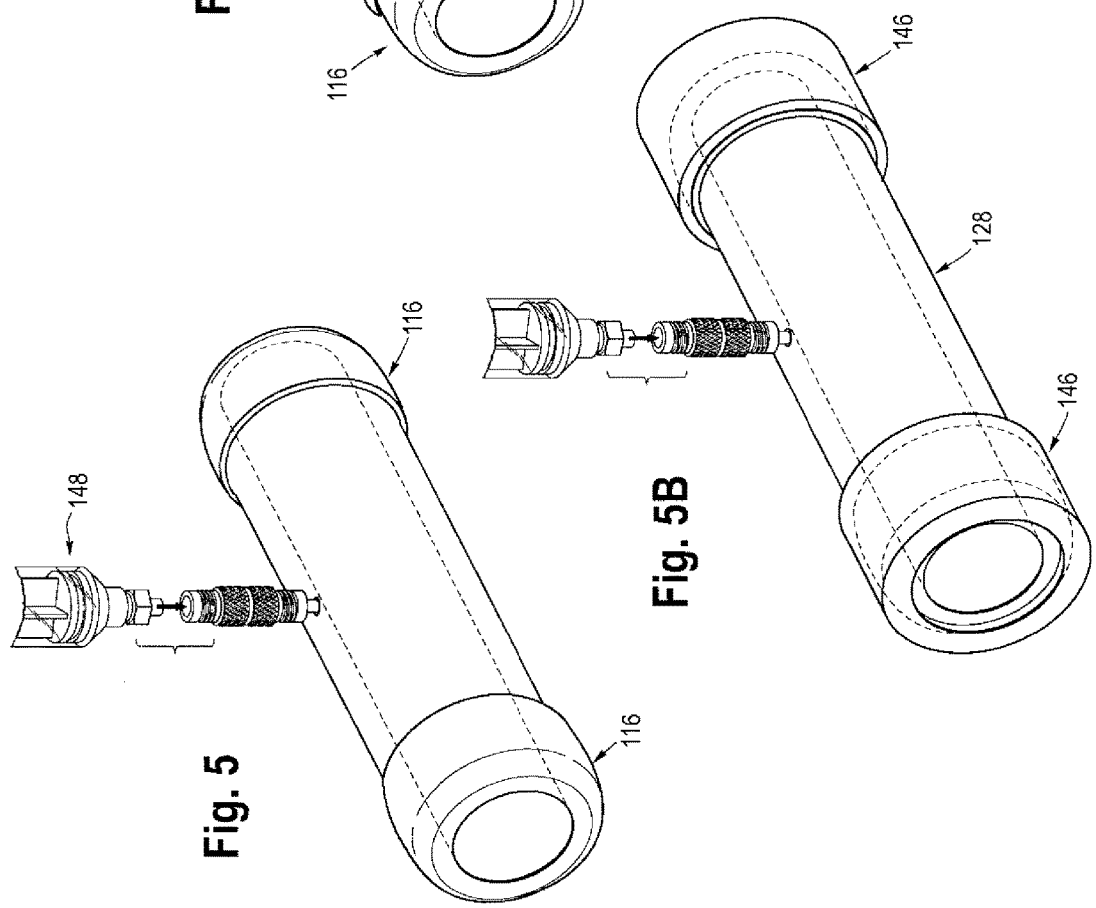

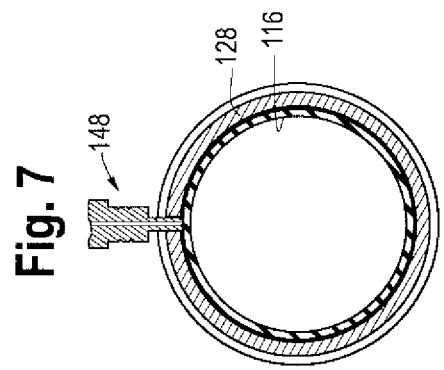
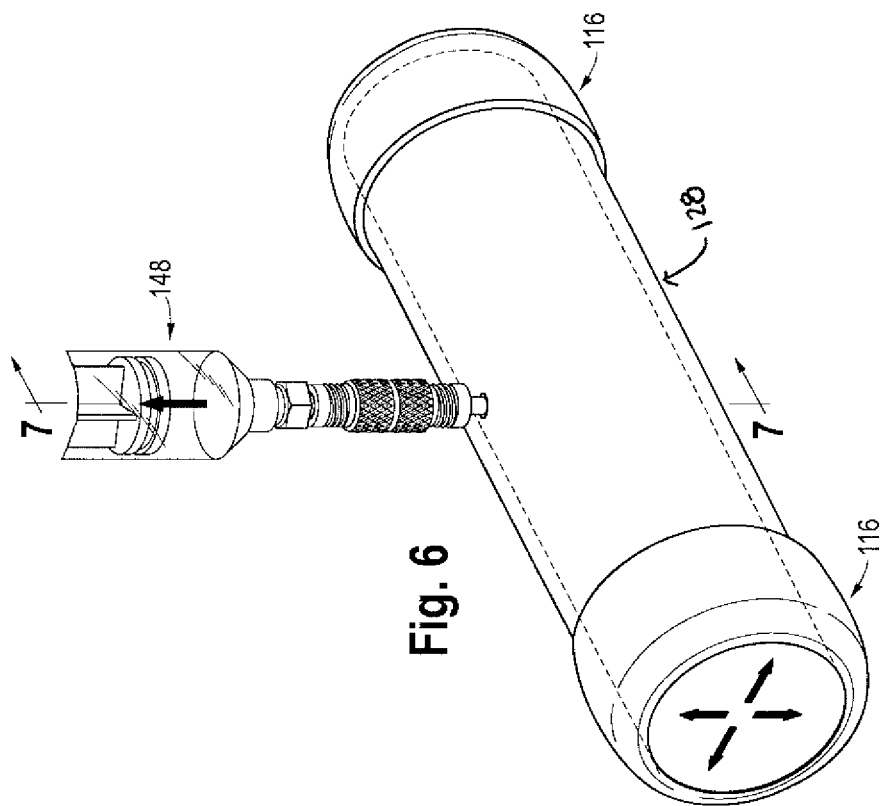

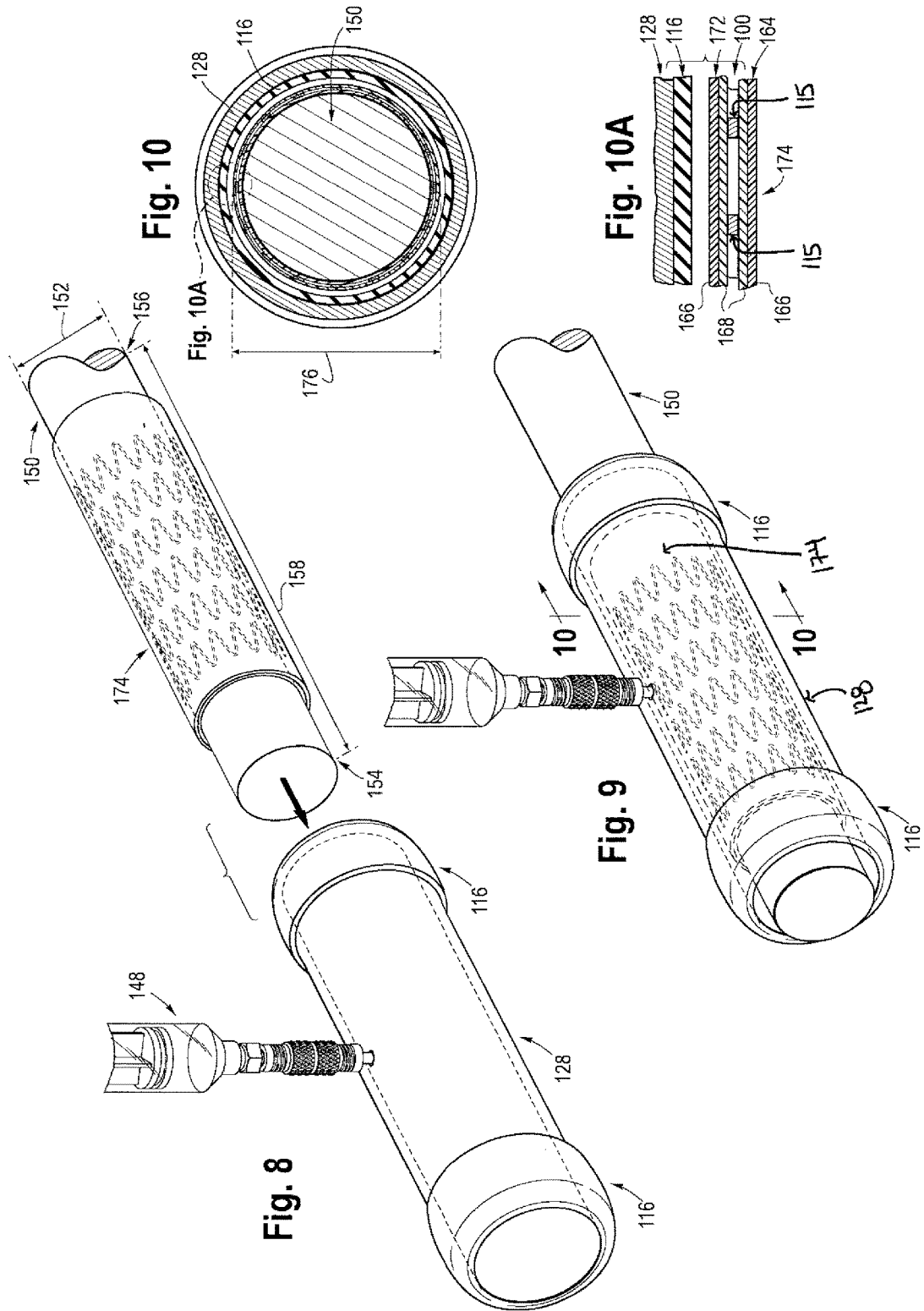

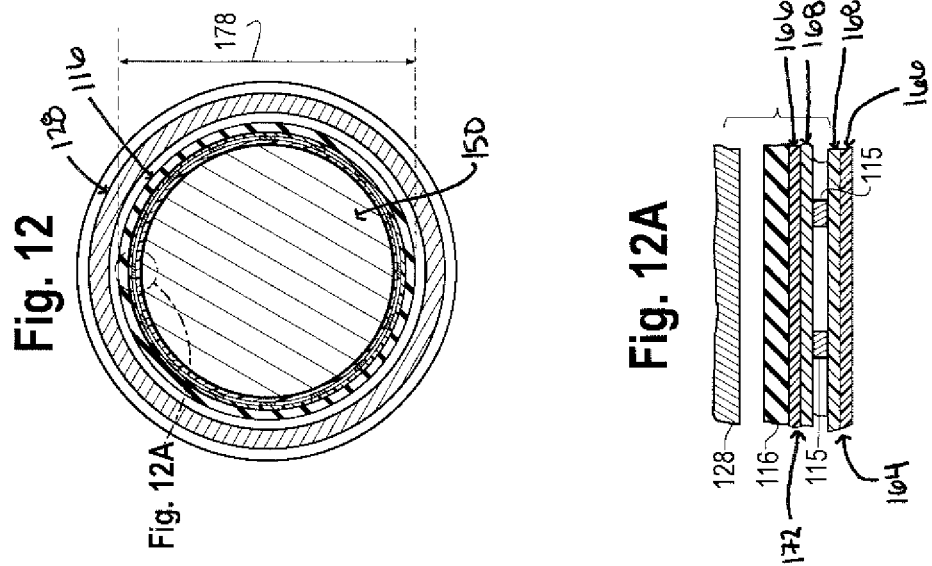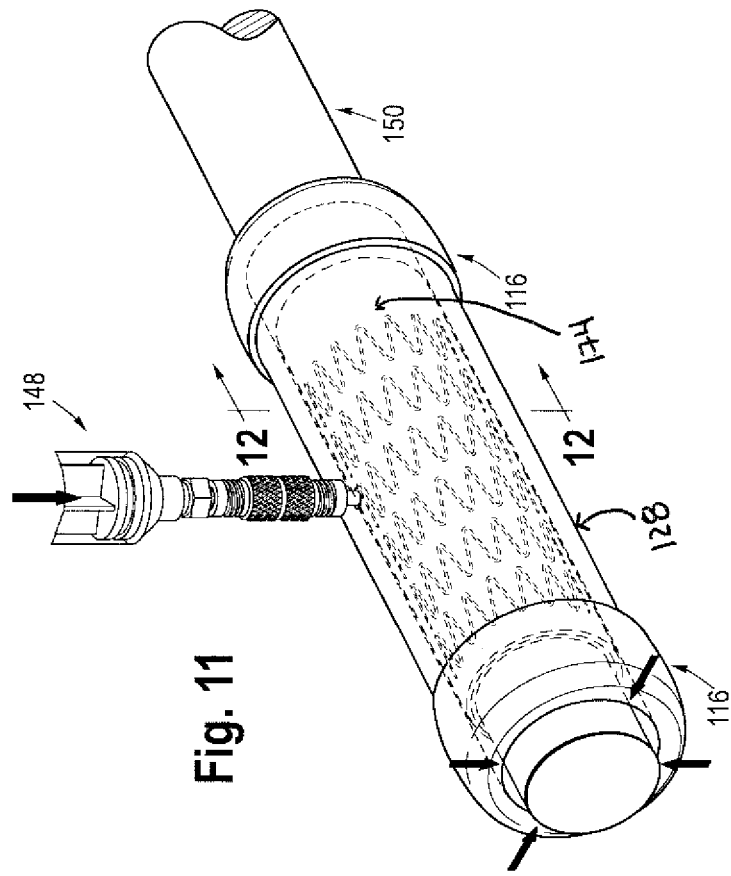

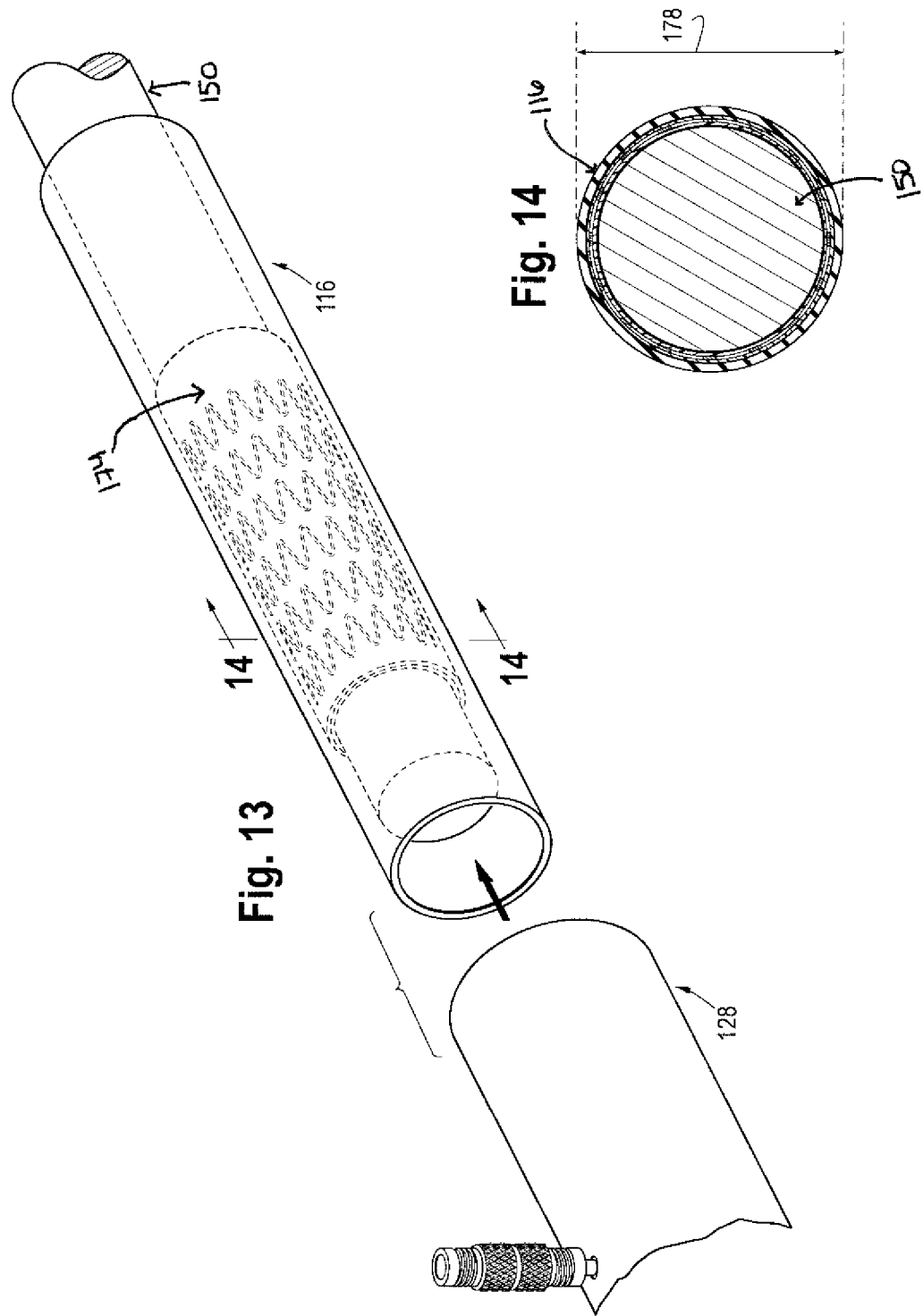

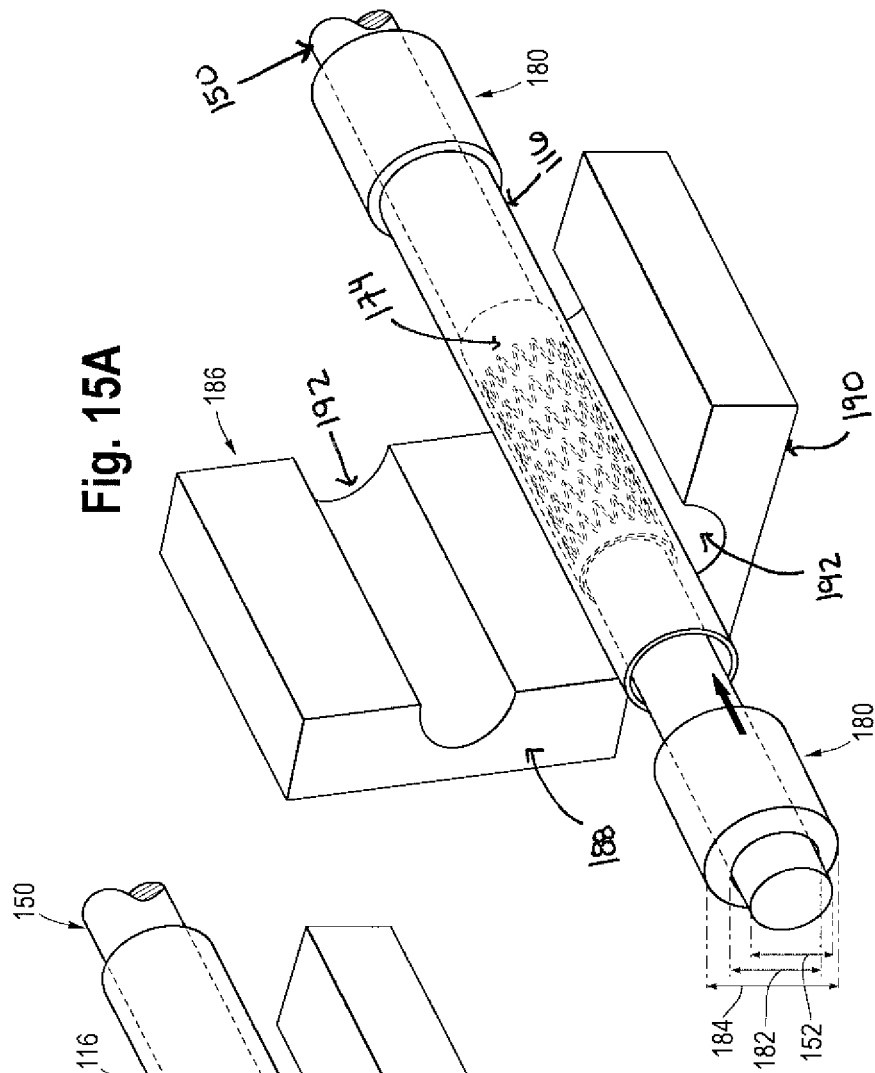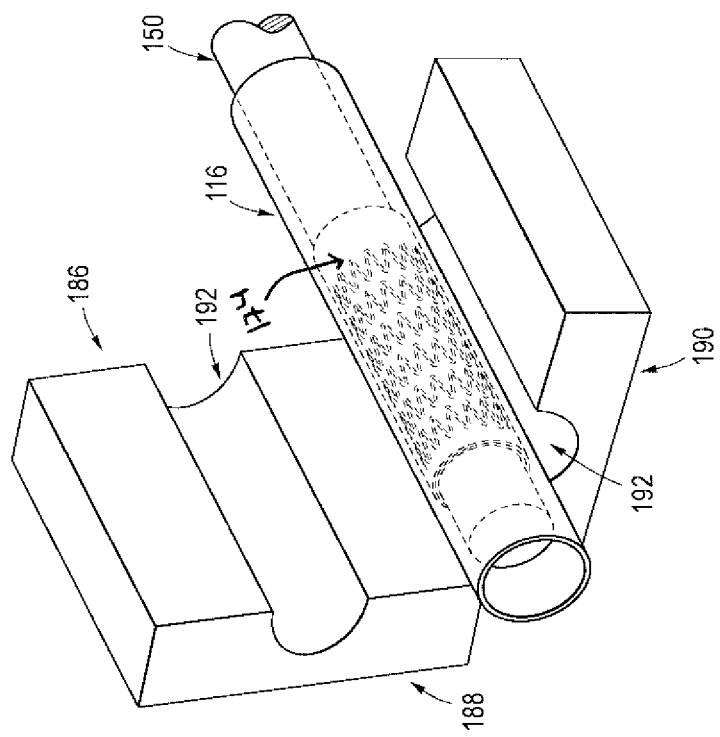

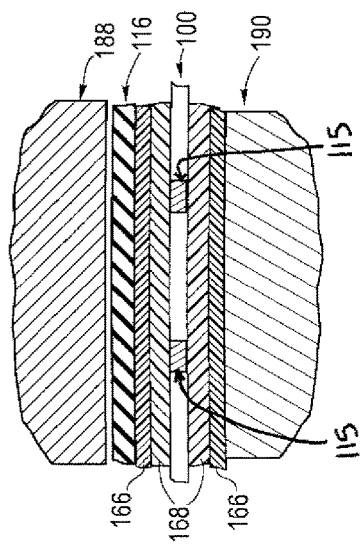
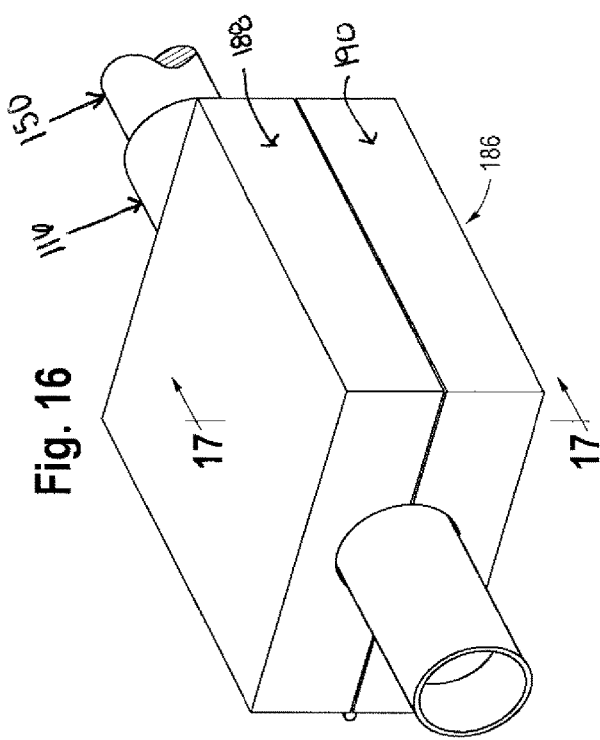
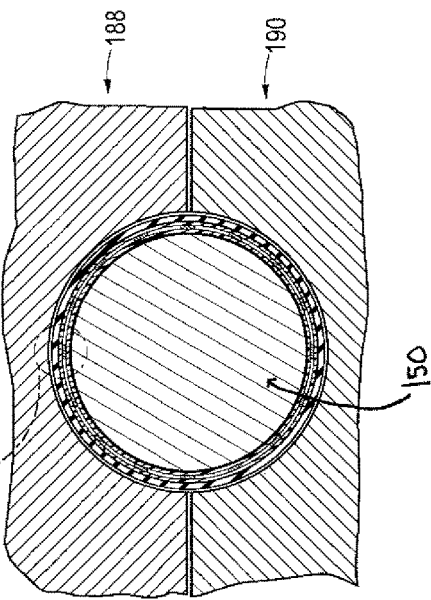

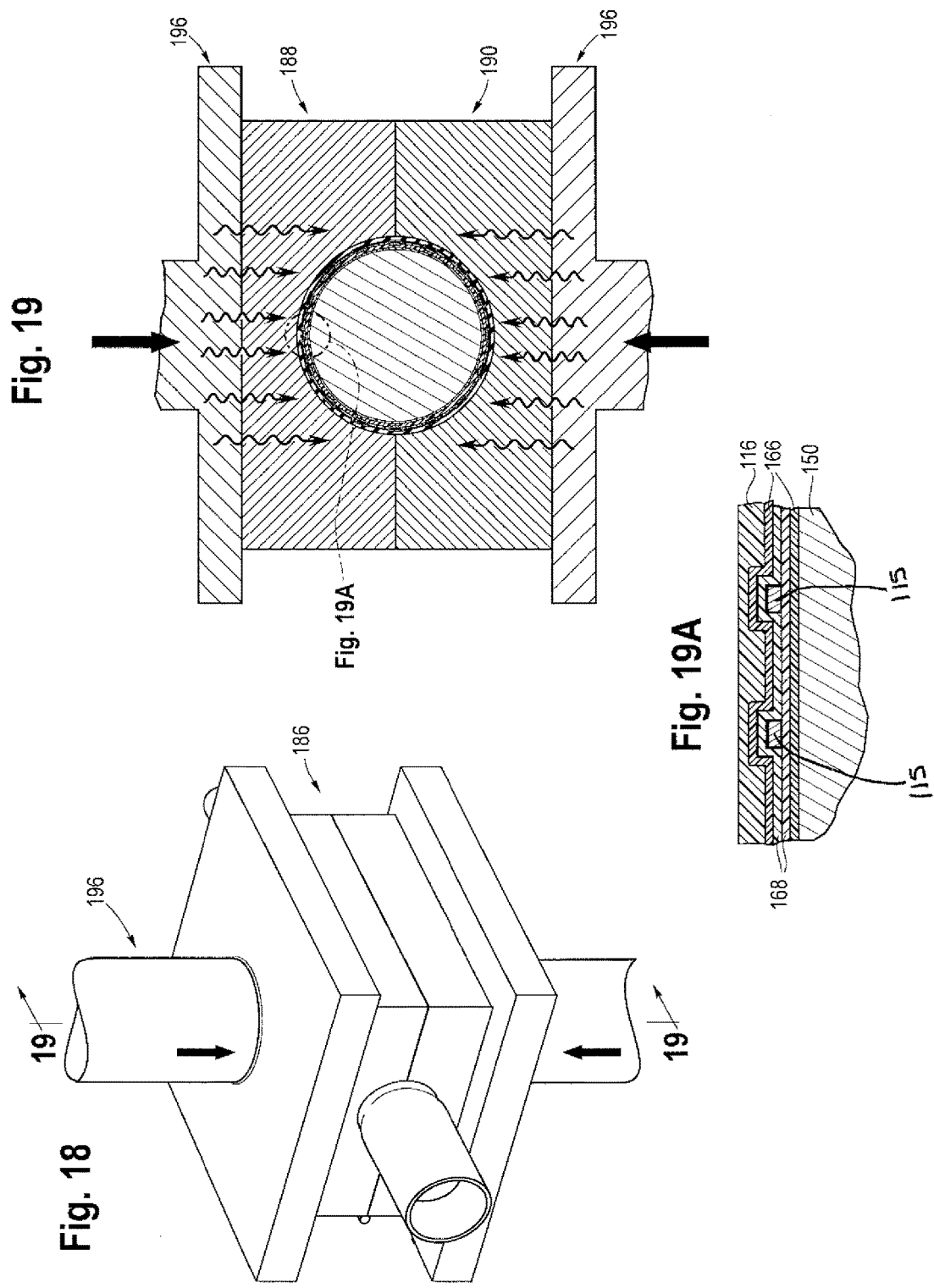

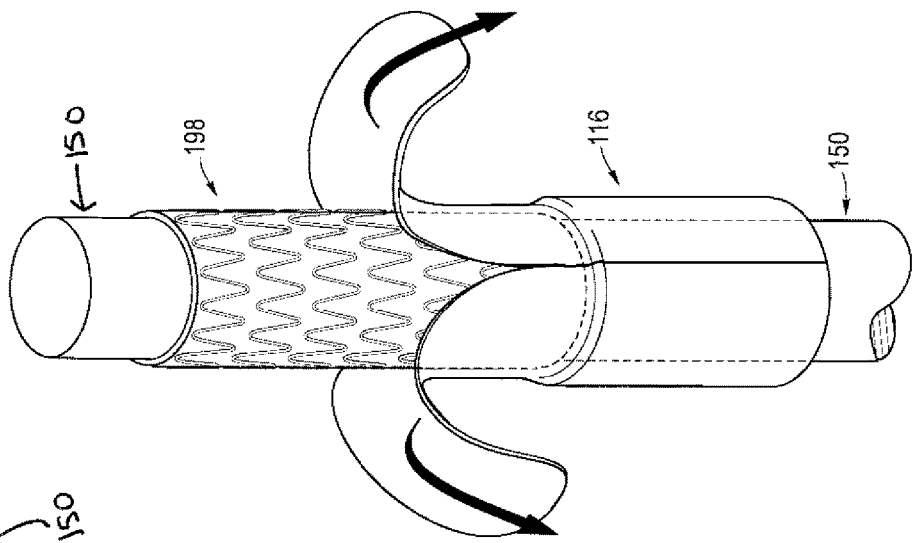
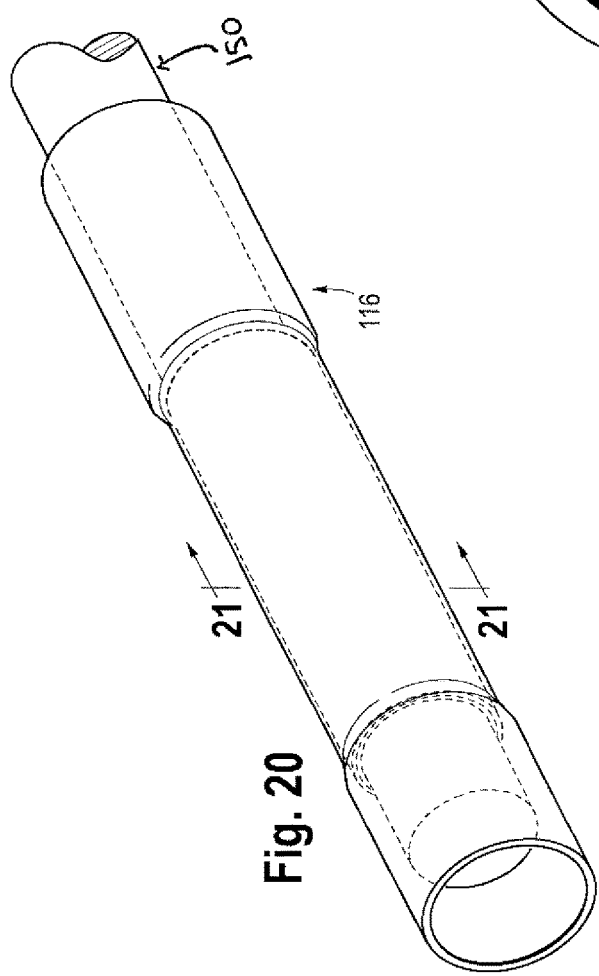
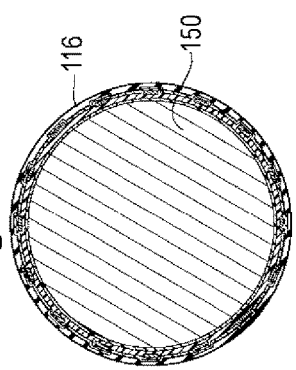

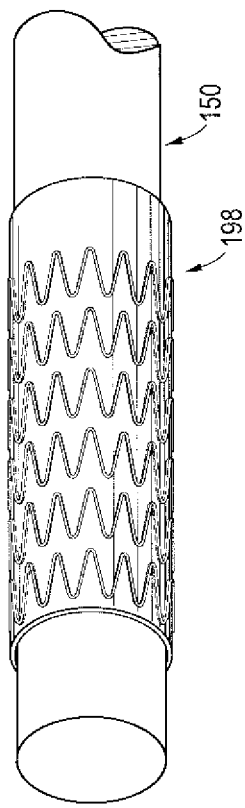
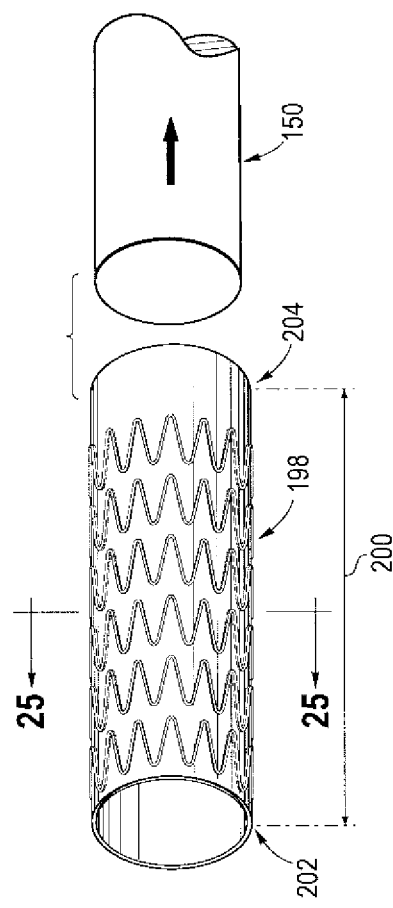
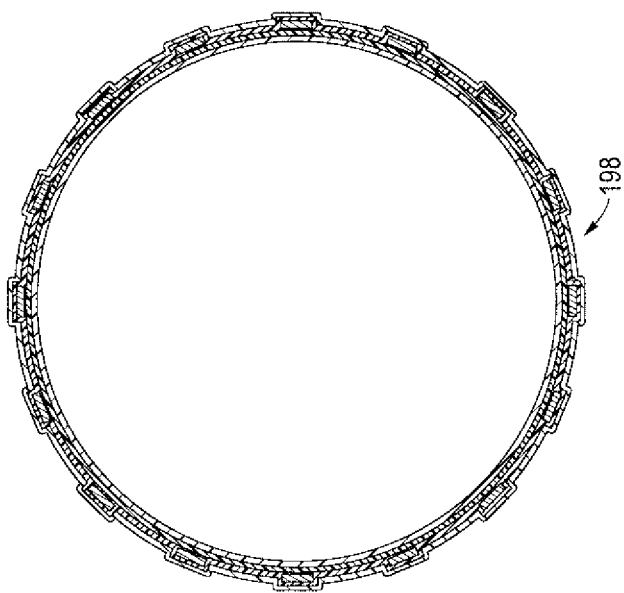

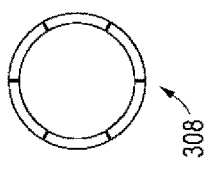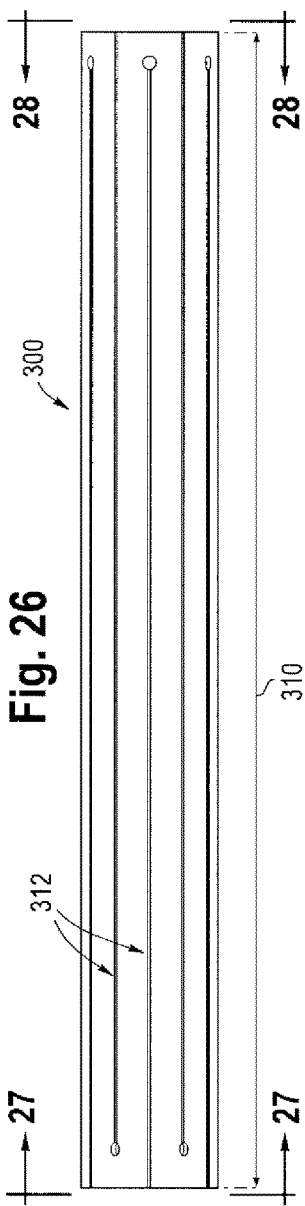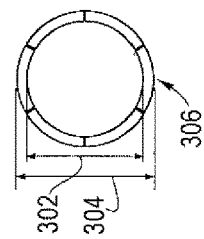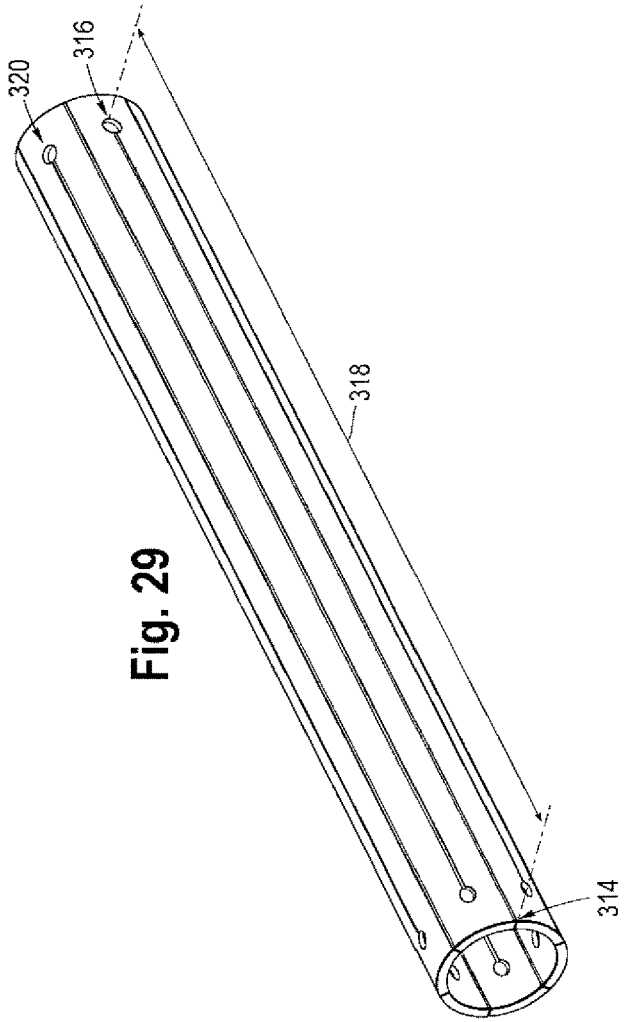

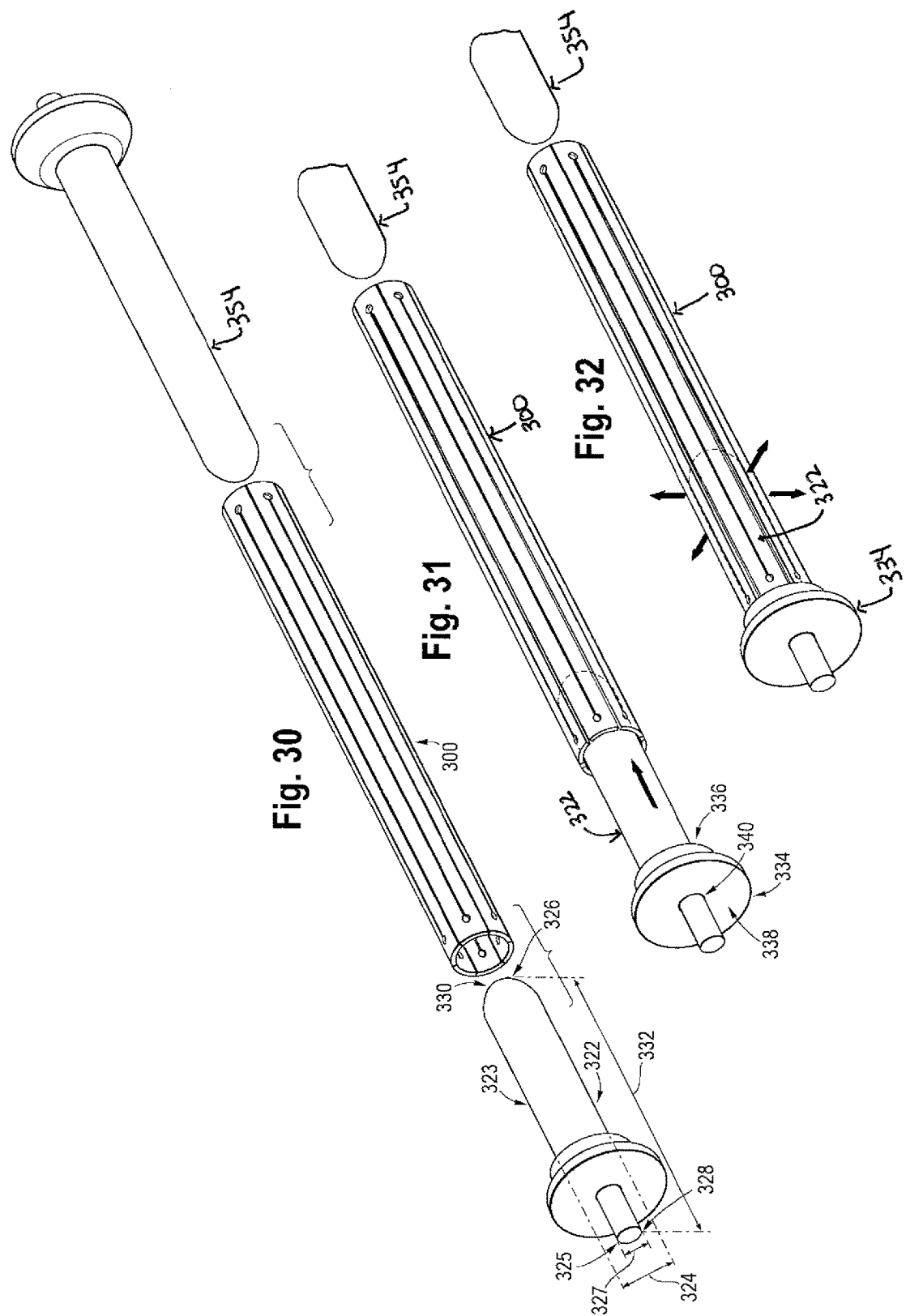

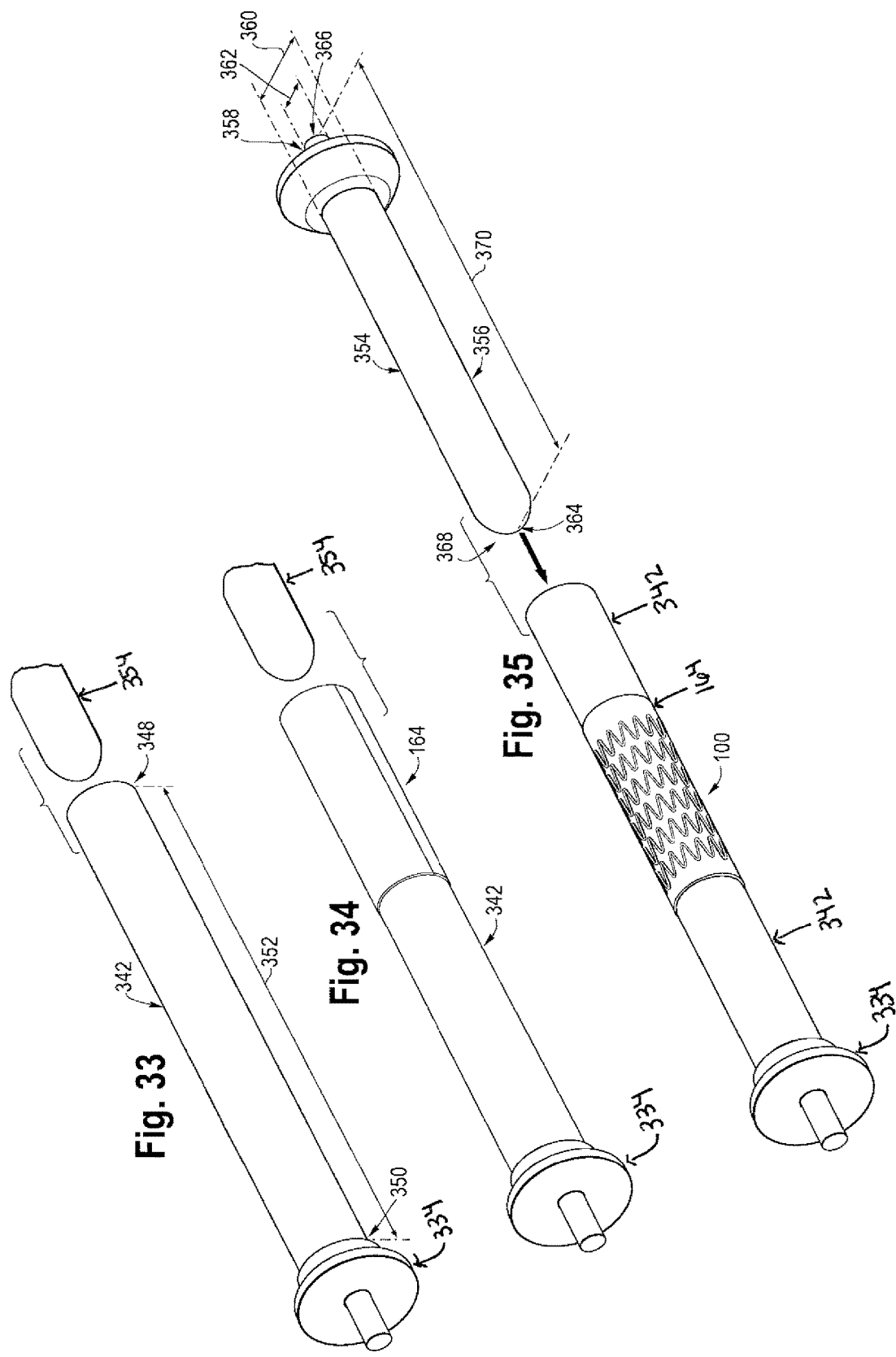

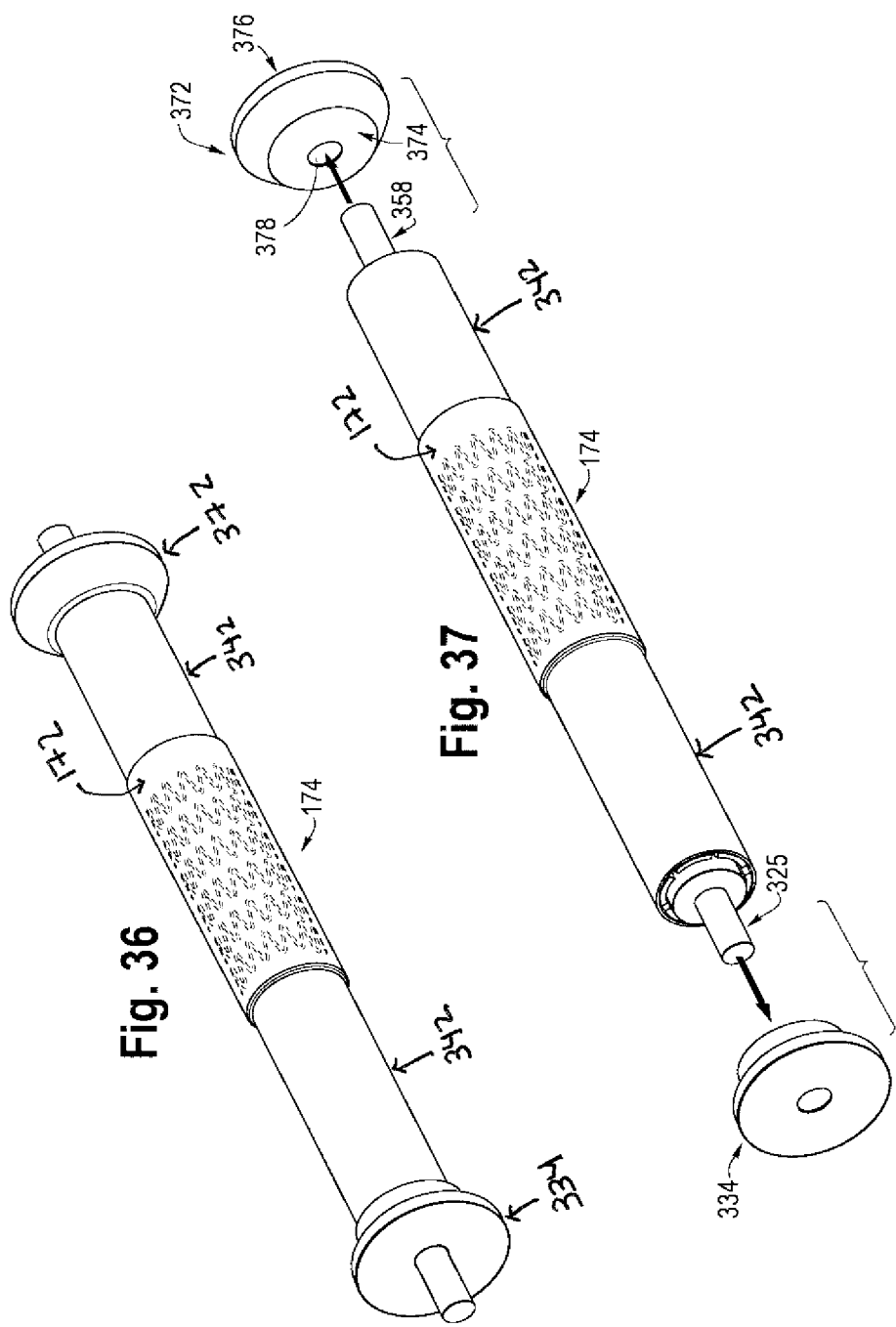

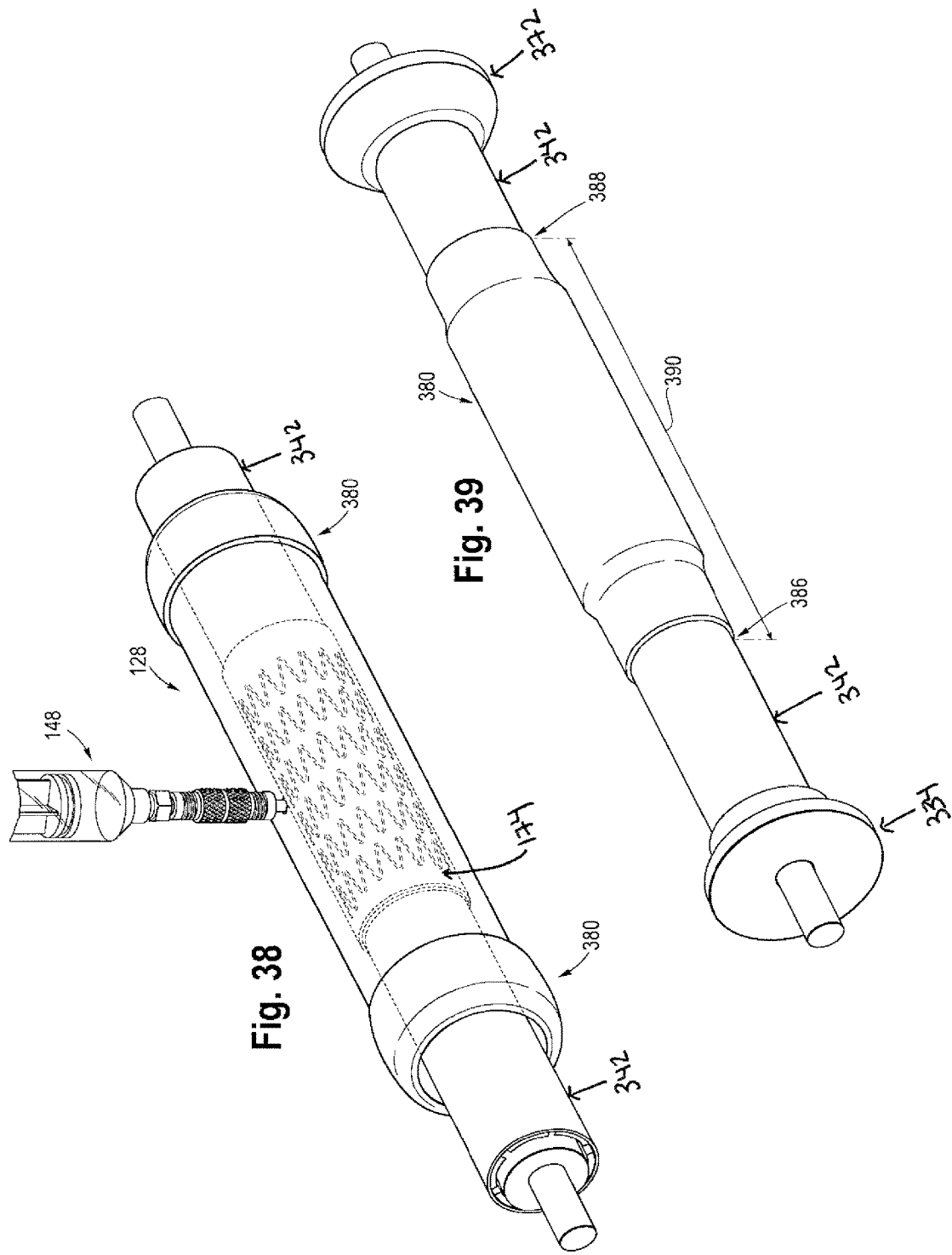

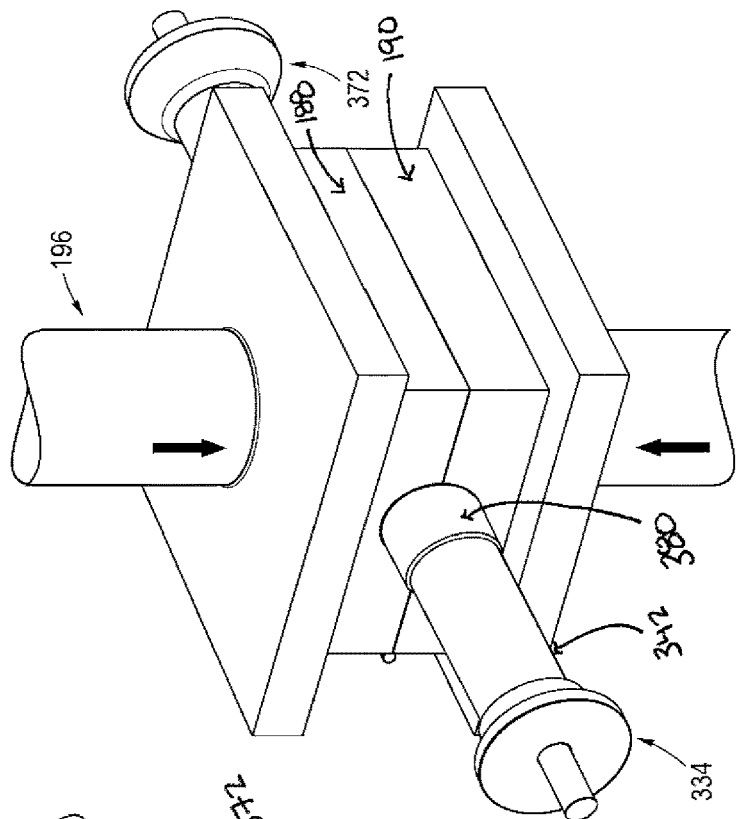
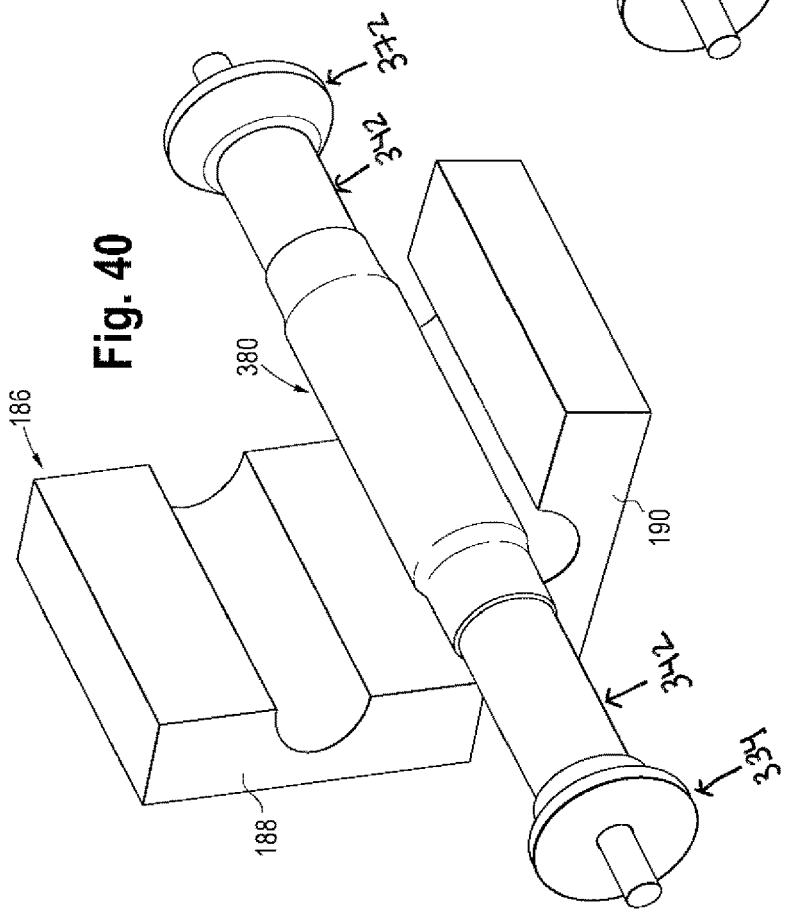

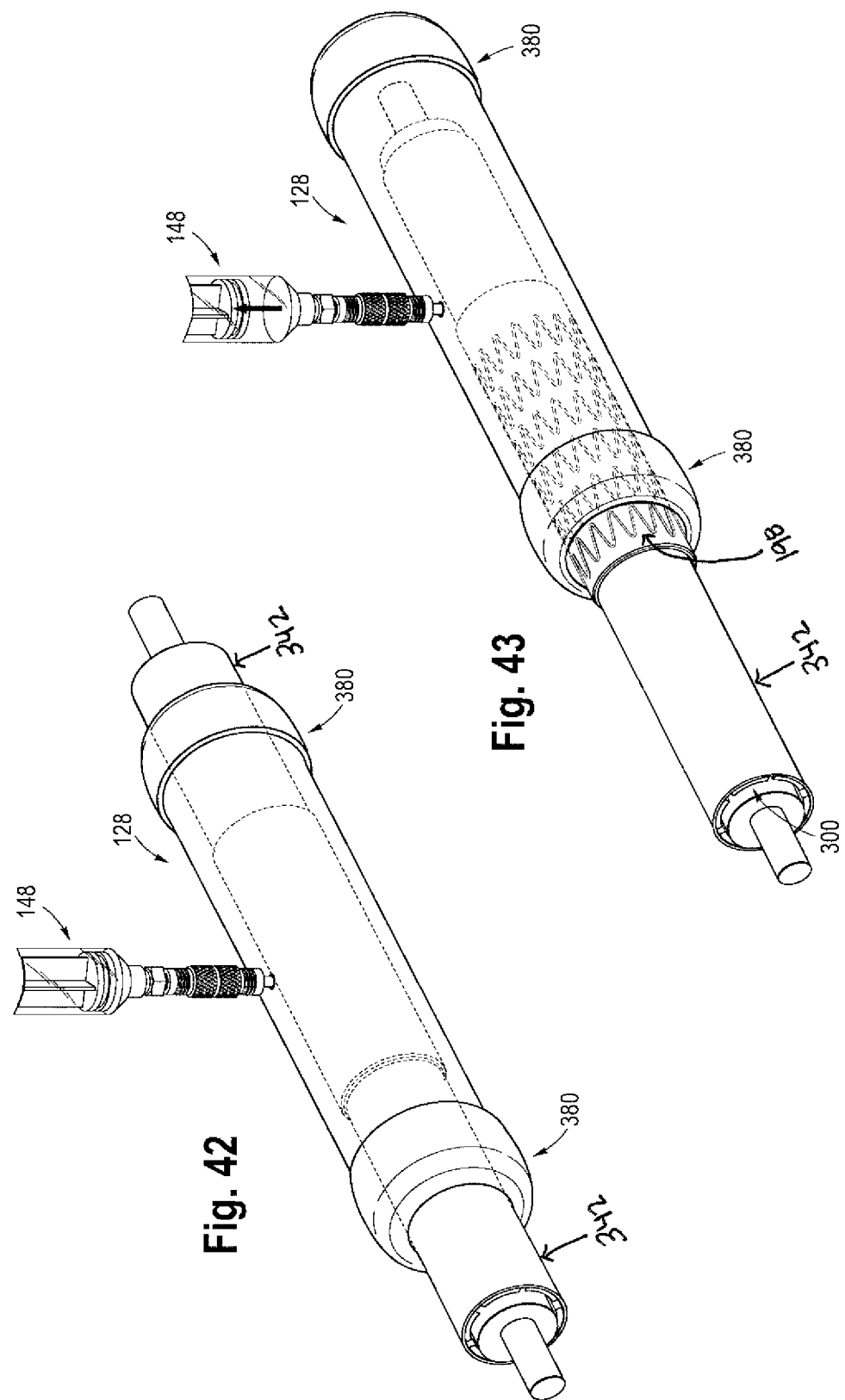

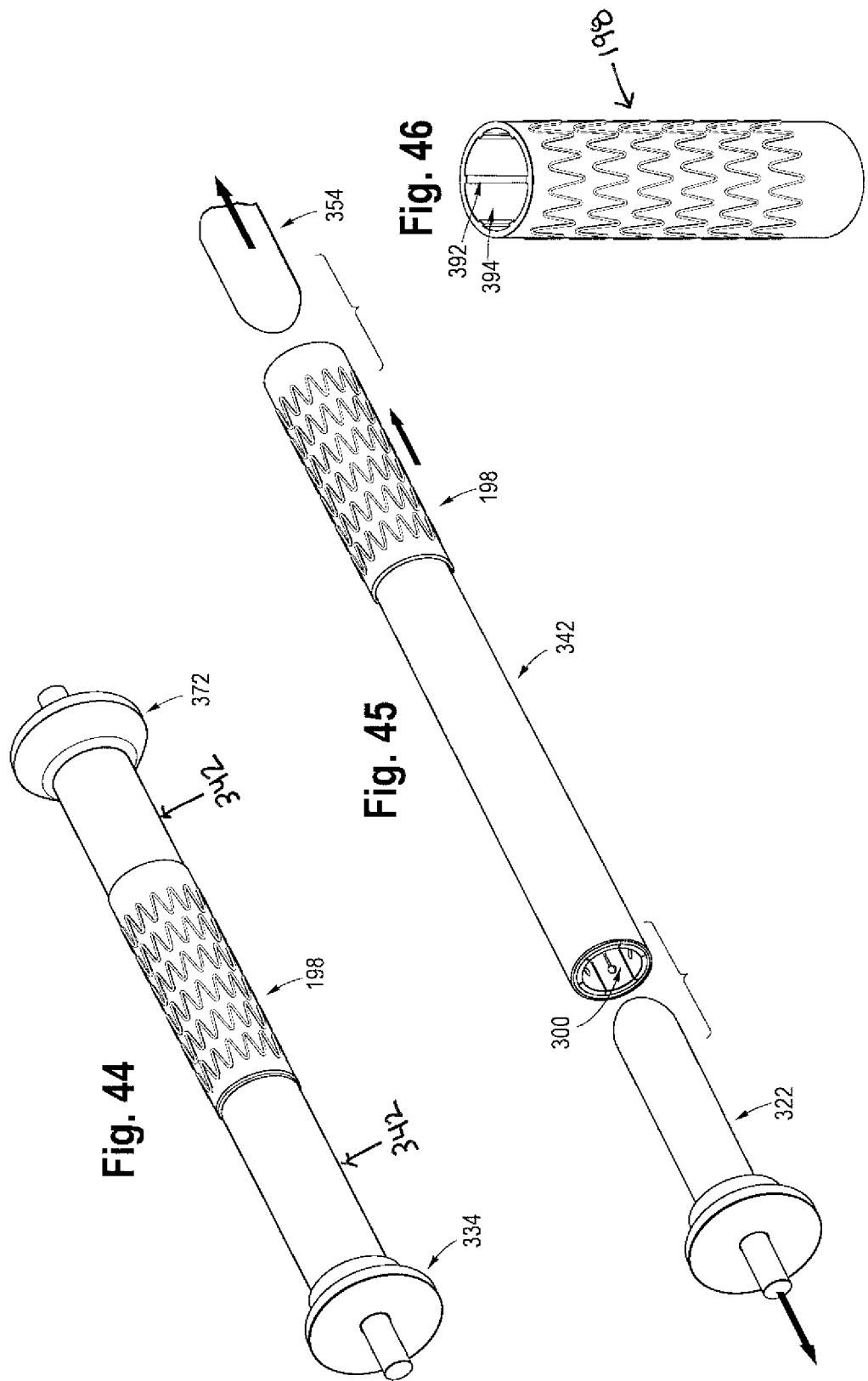

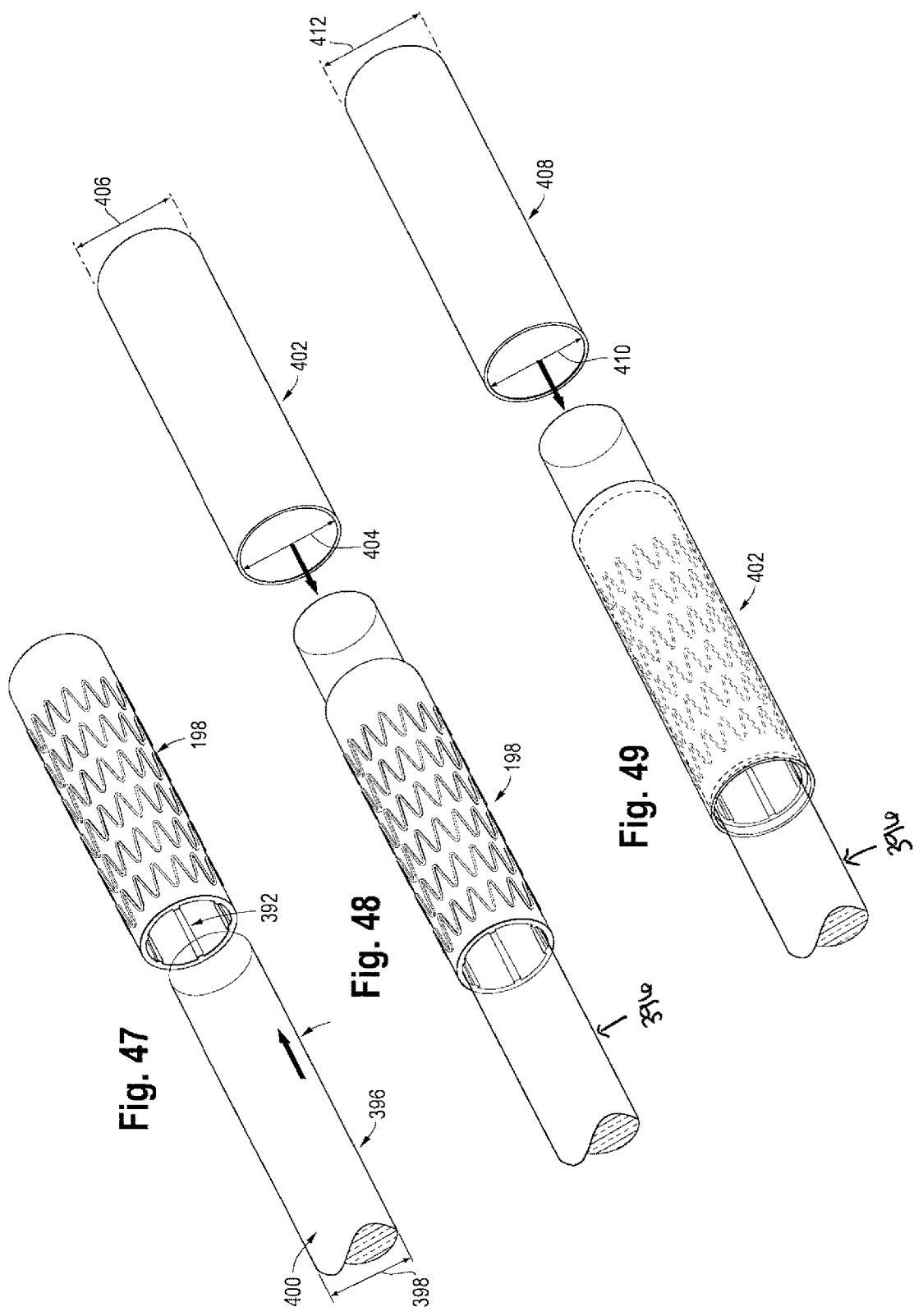

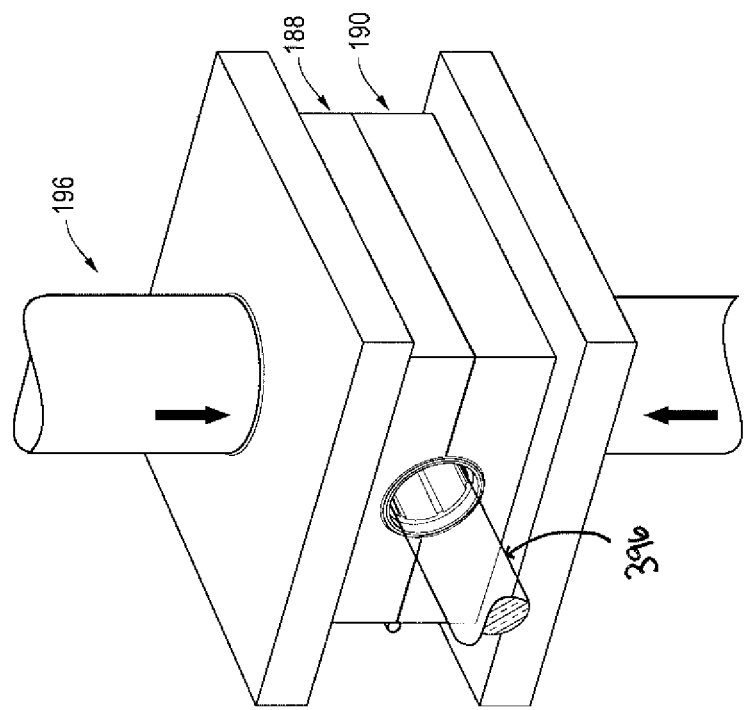
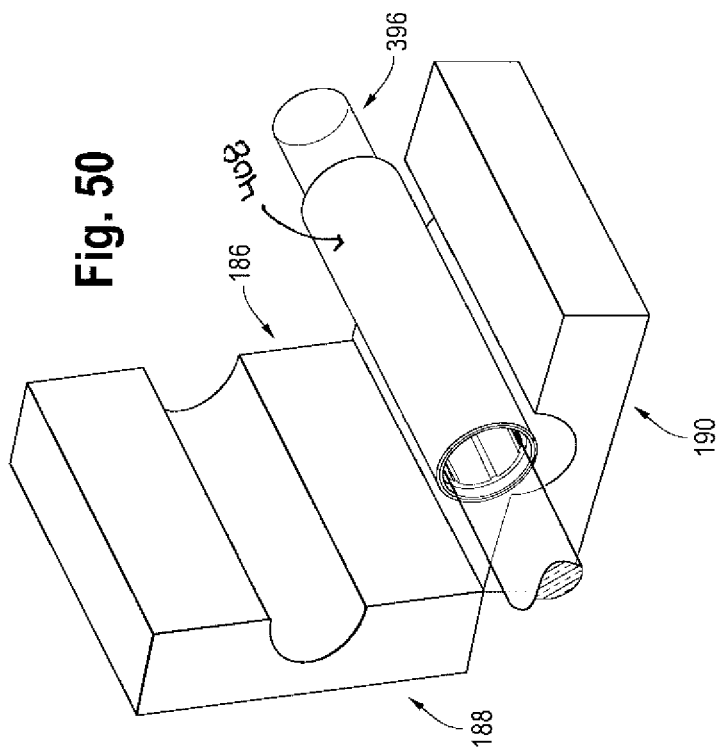

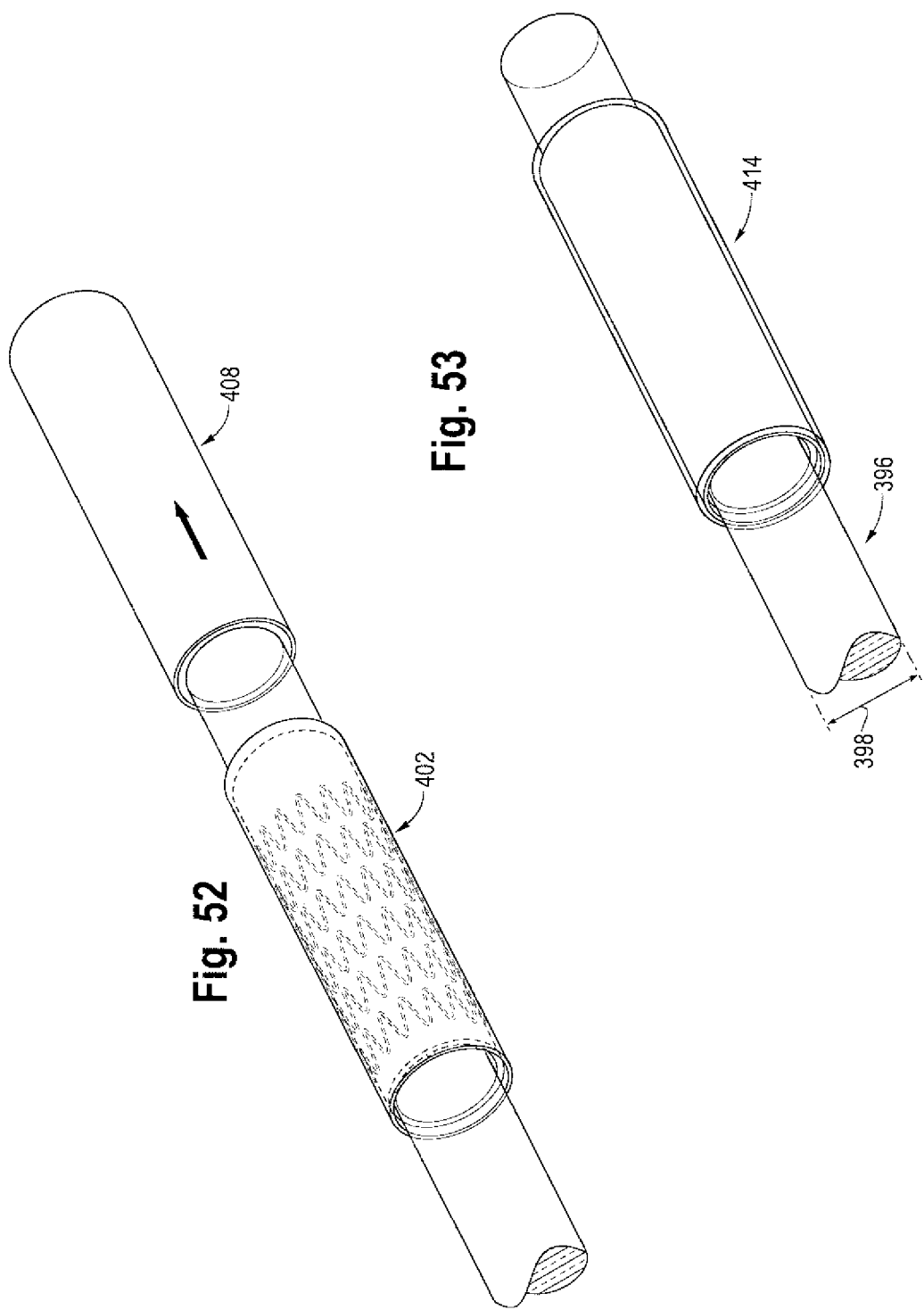

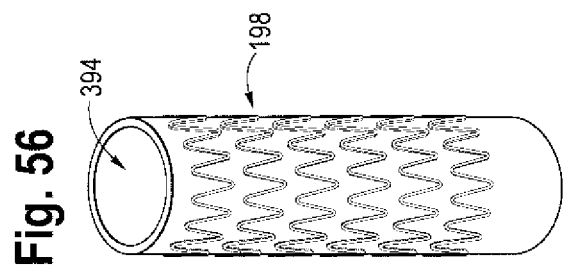
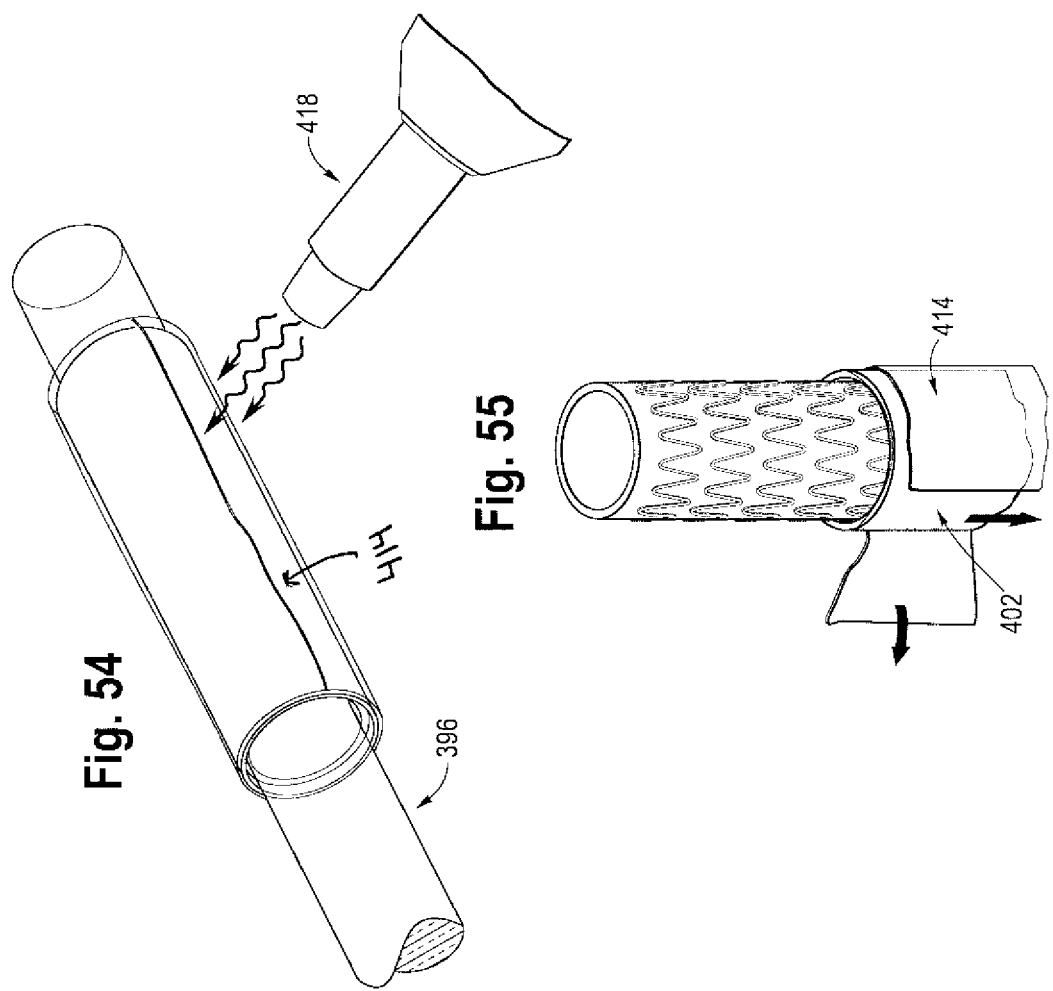

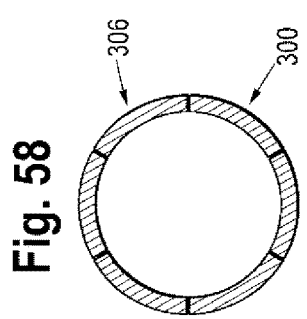
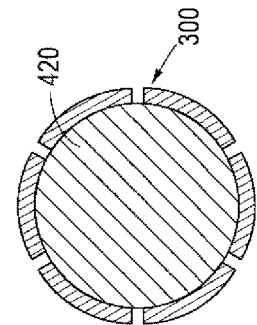
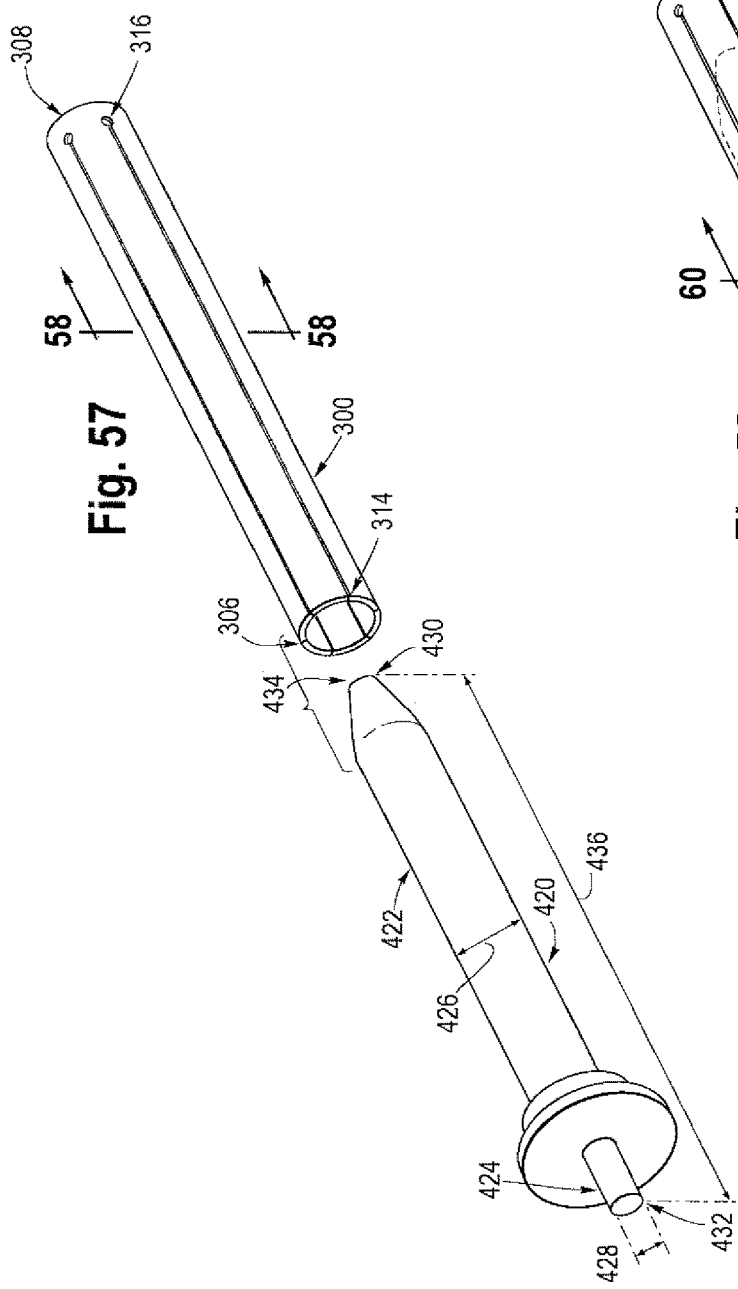
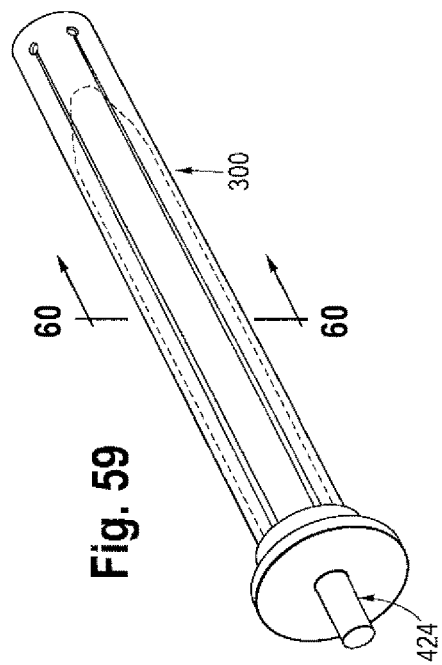

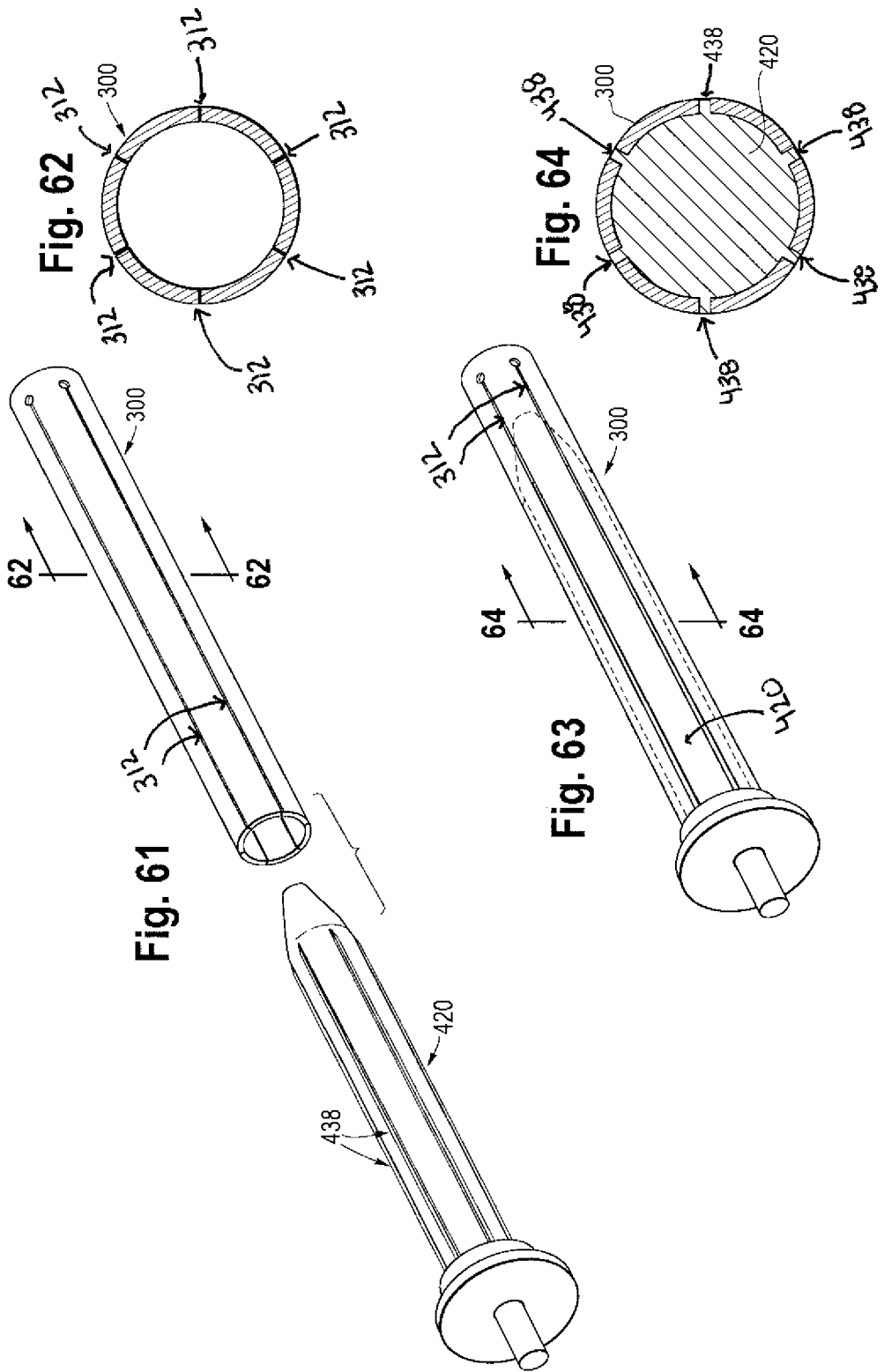

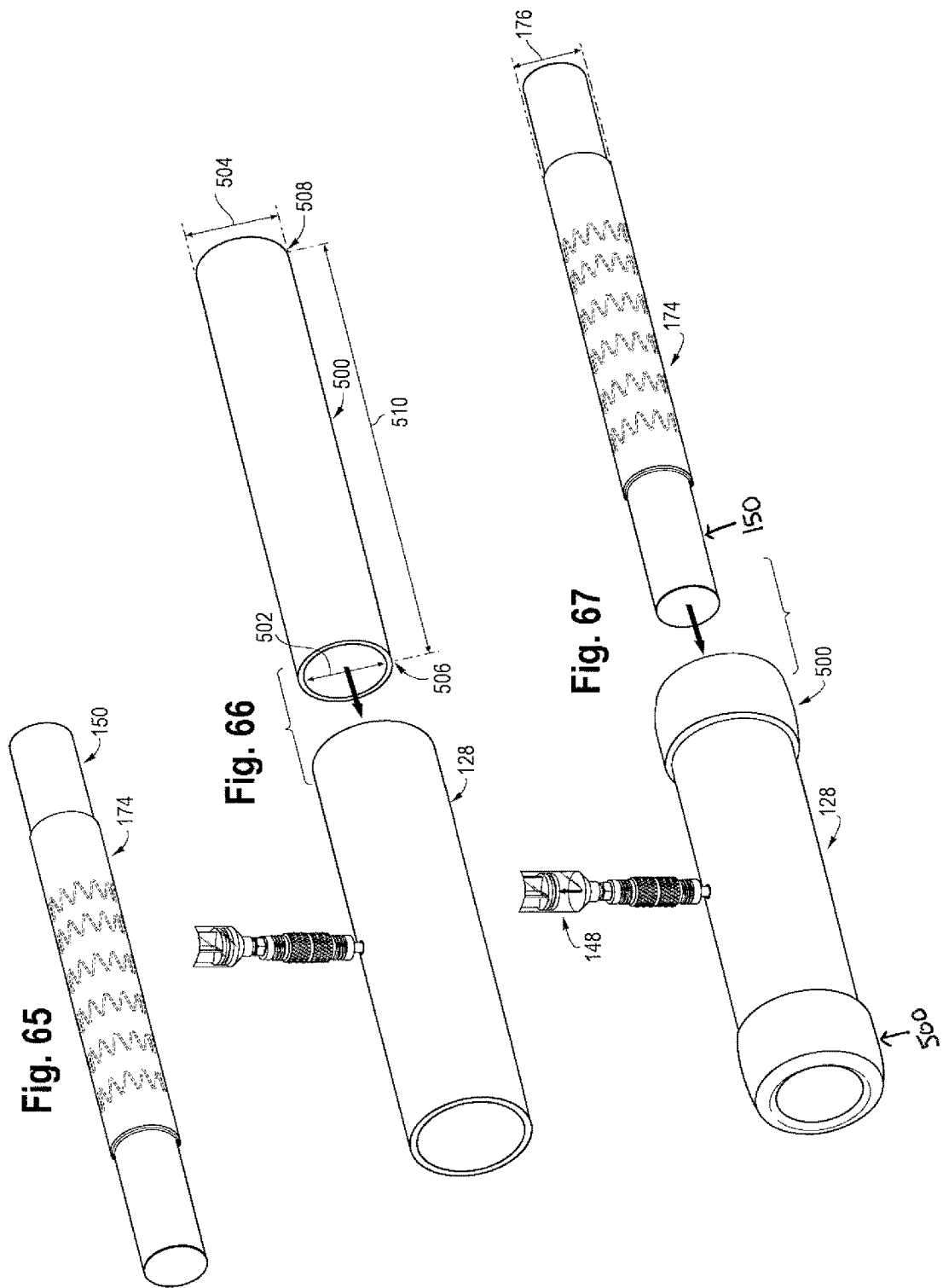

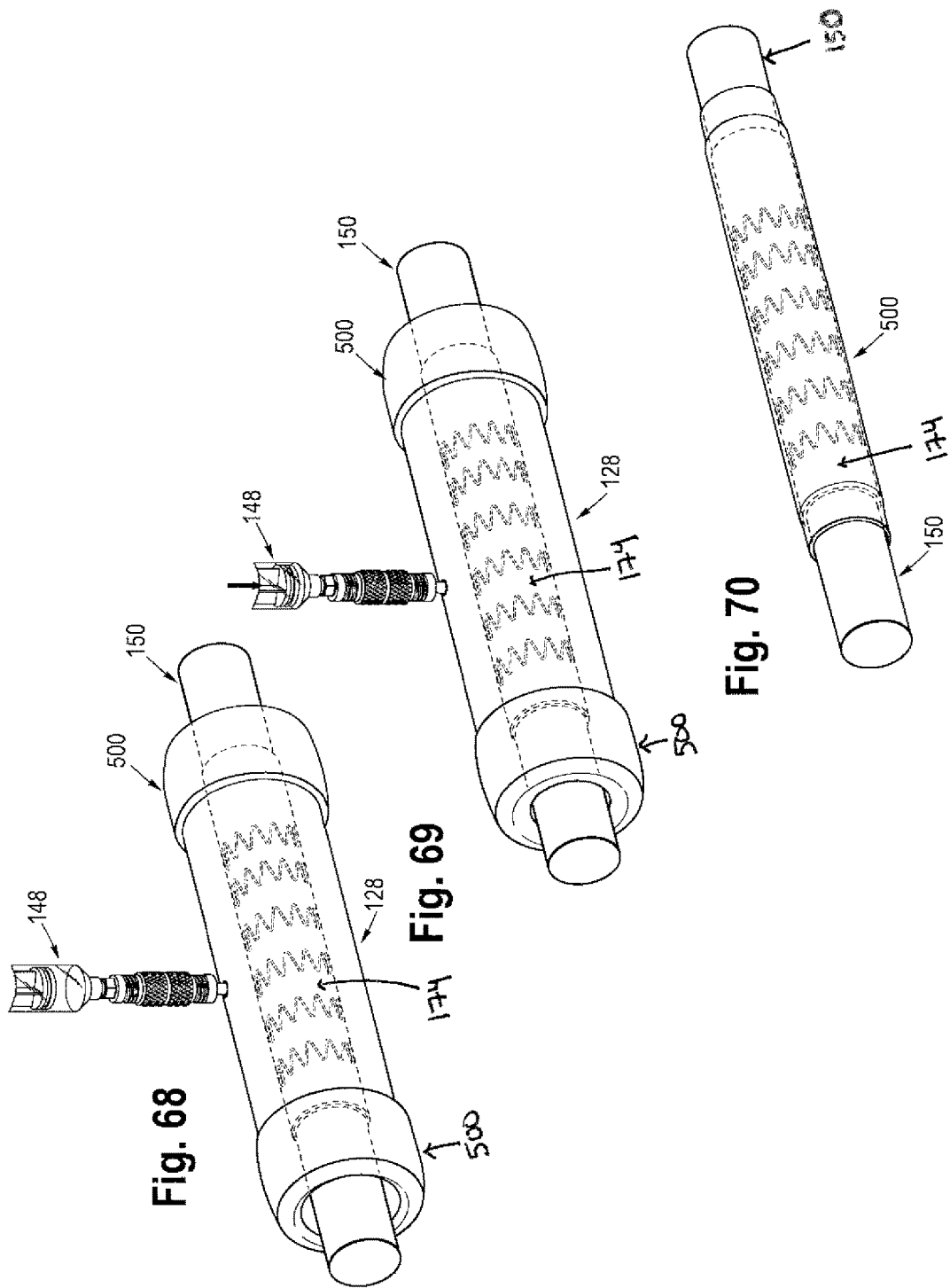

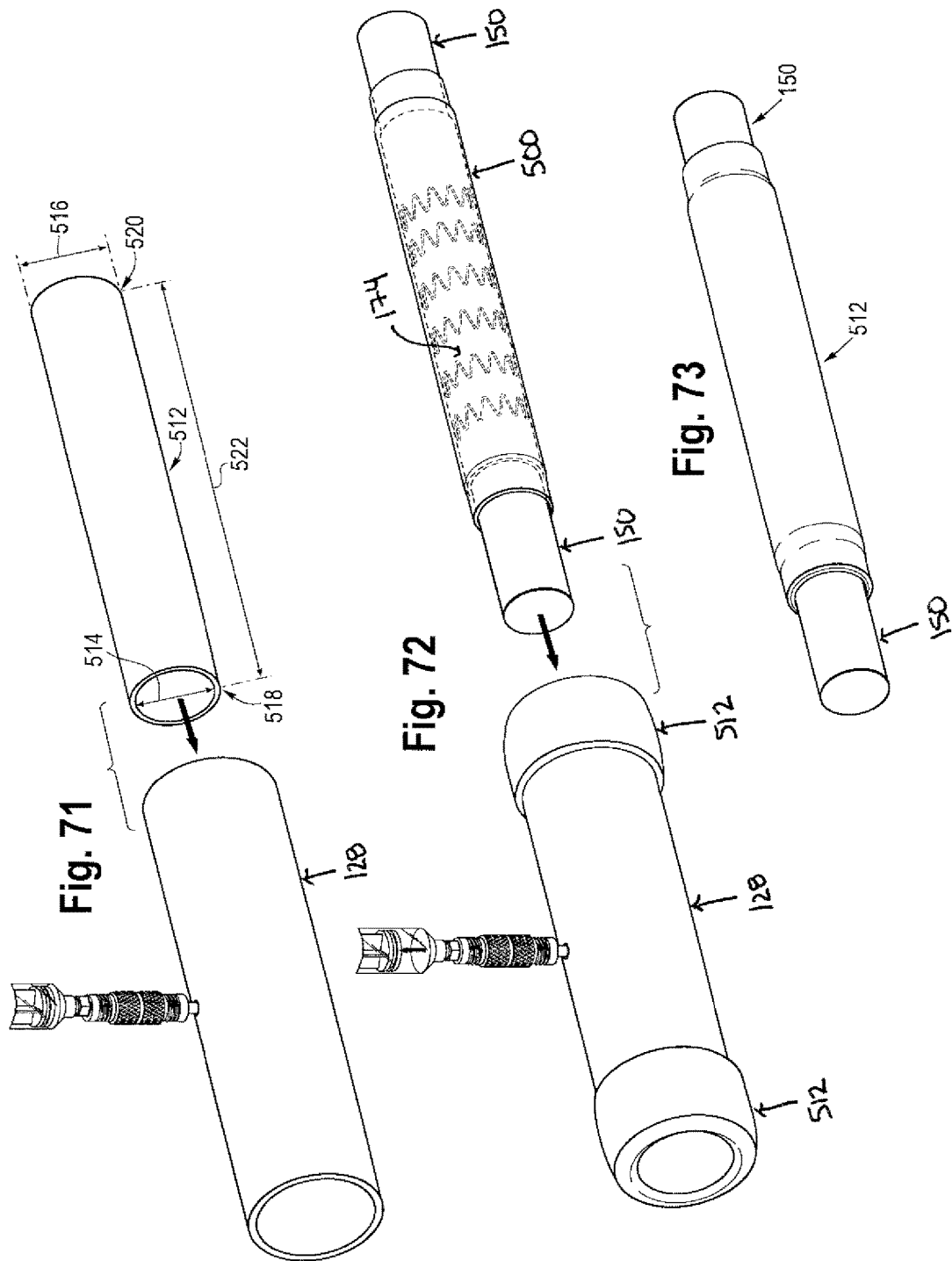

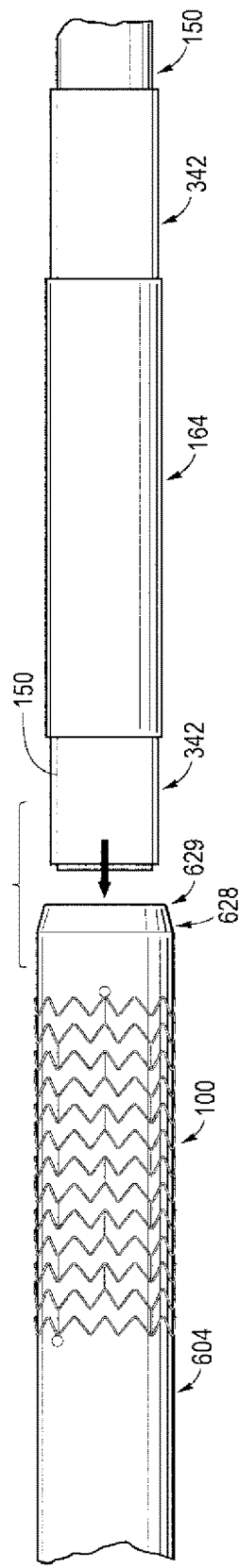
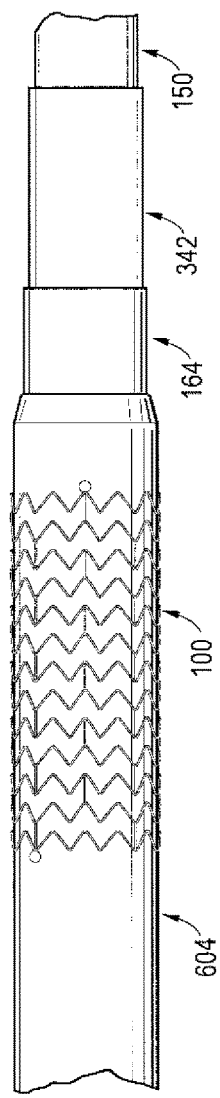
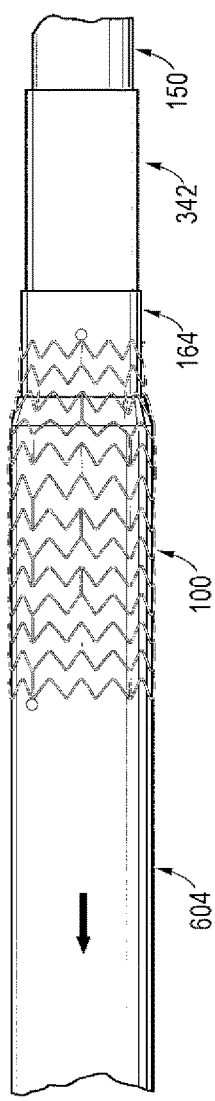
Fig. 85
Fig. 86
Fig. 87

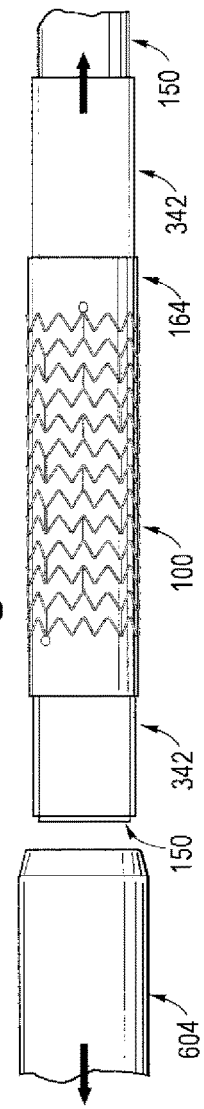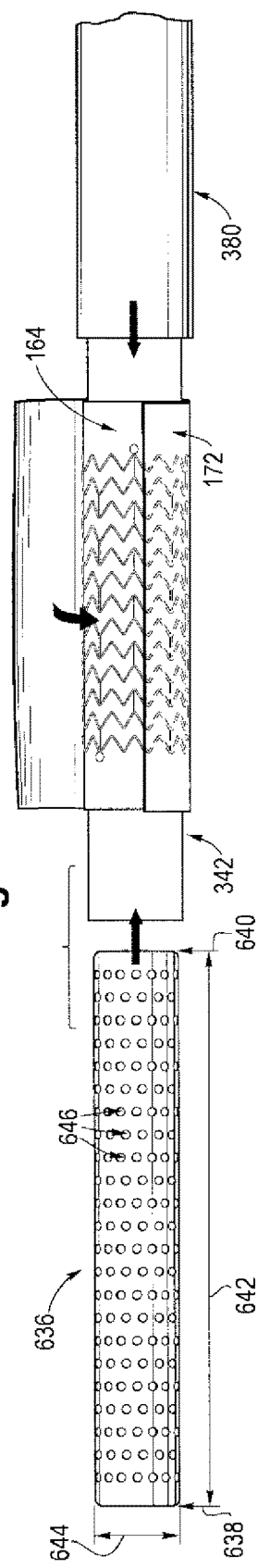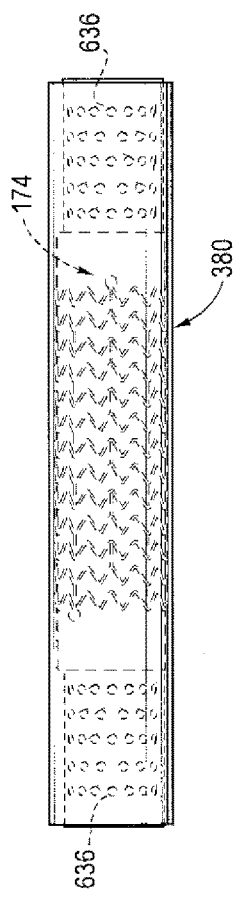

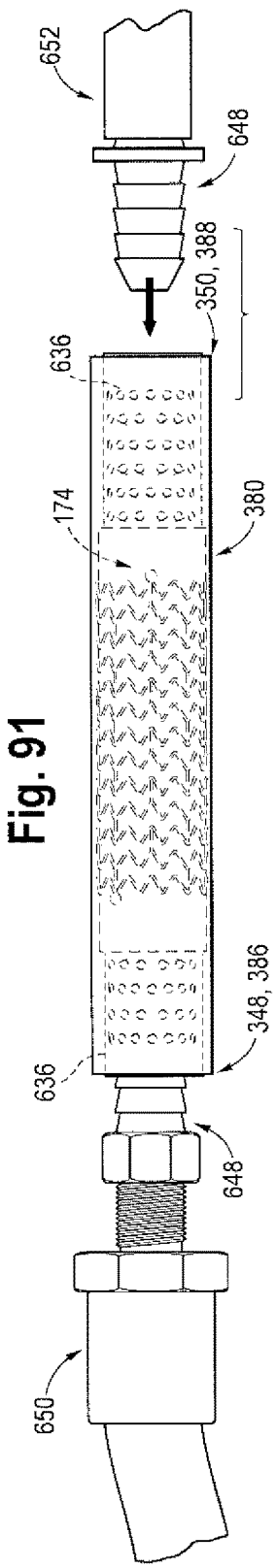
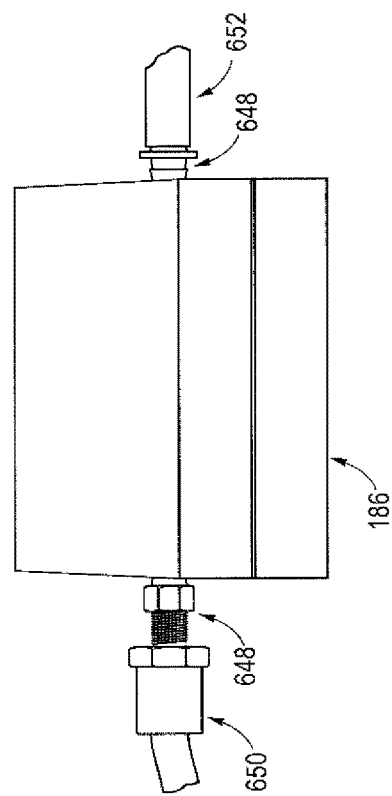
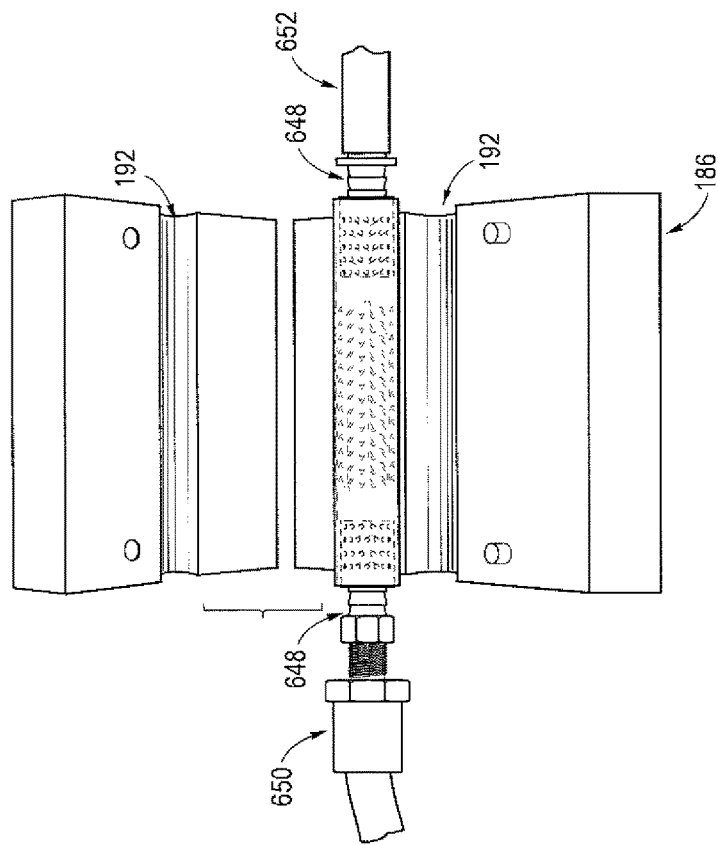

METHODS OF MAKING A PROSTHESIS WITH A SMOOTH COVERING

RELATED APPLICATIONS

The present patent document claims the benefit of the filing date under 35 U.S.C. § 119(e) of Provisional U.S. Patent Application Ser. No. 62/199,764, filed on Jul. 31, 2015, the entire contents of which are hereby incorporated by reference.

BACKGROUND

1. Technical Field

The present invention relates to methods of making a prosthesis with a smooth covering.

2. Background Information

Some medical prostheses, such as stents, include material, fabric or a graft to cover the prosthesis. Covered stents include a stent graft that includes fabric or other material that covers and is supported by a stent. Covered stents are manufactured by different methods. One method includes placing the stent on a mandrel between shells of a pressure applicator. The pressure applicator may include two halves or multiple components that form a cavity with a circular cross section. Each component of the pressure applicator may contain one or more layers of material for application to the stent. When the components of the pressure applicator are brought together to cover the stent, the resulting covered stent may have visible creases where the components meet. The creases create a lack of continuity in the material covering the stent and may cause premature failure of the material or an area that may catch on a vessel or collect undesirable material.

Other methods of manufacturing covered stents include using shrink tubes and/or tubing that are off the shelf and readily available to attach the fabric or graft on the stent. For example, covered stents have been made using off the shelf silicone tubing having a high durometer, such as high durometer silicone tubing including silicone tubing with a durometer of 50-70 Shore A. Manufacturers identify silicone tubing having a durometer of 50-70 Shore A as soft and silicone tubing having a durometer of 35-45 Shore A as very soft, both of which are readily available from manufacturers. Silicone tubing with a lower durometer is not readily available from manufacturers.

These methods to make covered stents using shrink tubes, tubing having a high durometer, and/or sheets of material having a high durometer to attach the fabric or graft on the stent may create visible creases or ridges that form on the graft of the stent, which create a lack of continuity on the stent. Previously used pressure methods also cause the struts of the stent to deform or distort when the shrink tubes or high durometer tubes are applied to the fabric and the stent because higher deformation forces and displacement of the tubes is needed to compress the fabric or graft around the struts of the stent for bonding. In addition, when using these methods, the fabric or graft is not able to conform to the struts of the stent, or otherwise profile the struts of the stent, to create a smooth covering over the stent.

BRIEF SUMMARY OF THE INVENTION

A method of making a stent with a smooth covering is described. The method includes using a low durometer elastomeric tube, preferably a low durometer silicone tube, in the method of making a covered prosthesis.

One exemplary method includes positioning the elastomeric tube in a tube expander, and applying a vacuum to the tube expander to increase both the inner and outer diameters of the elastomeric tube. In one example, a mandrel is then provided with an inner covering. A stent is positioned over the inner covering, and then an outer covering is positioned over the stent to form a covered stent. In some examples, only an inner covering may be used or only an outer covering may be used. The mandrel and the covered stent are placed in the tube while the elastomeric tube is still in the tube expander, and the vacuum is released. Release of the vacuum causes the elastomeric tube to return to its previous diameter. The elastomeric tube, the covered stent, and the mandrel are then removed from the tube expander. Pressure and heat are applied to the elastomeric tube, the covered stent, and the mandrel. The pressure and heat are then removed. The elastomeric tube is removed from the now covered stent and the covered stent is removed from the mandrel.

A variation of the method includes providing a slit cannula including an inner diameter, an outer diameter, and a plurality of slits. A first elastomeric tube is positioned over the slit cannula, and an inner covering is positioned over the first elastomeric tube. A stent is positioned over the inner covering. A mandrel is positioned within the slit cannula to expand the first elastomeric tube and the inner covering. A second covering is positioned over the stent. A second elastomeric tube is provided that includes an inner diameter and an outer diameter, and the second elastomeric tube is positioned in a tube expander including a vacuum. A vacuum is applied to expand the inner diameter and outer diameter of the second elastomeric tube. The covered stent, the first elastomeric tube, the slit cannula, and the mandrel are then positioned in the second elastomeric tube within the tube expander, and the vacuum is released. The first and second elastomeric tubes, the covered stent, the slit cannula, and the mandrel are removed from the tube expander, and heat and pressure are applied to the first and second elastomeric tubes, the covered stent, the slit cannula, and the mandrel. The first and second elastomeric tubes, the covered stent, the slit cannula, and the mandrel are removed from the pressure and the heat, and the second elastomeric tube is removed from the covered stent. The mandrel is removed from the slit cannula, and the covered stent is removed from the first elastomeric tube and the slit cannula.

Another variation includes encapsulating a prosthesis with a smooth covering. The method includes providing a mandrel and positioning a first covering over the mandrel. A prosthesis is positioned over the first covering, and a second covering is positioned over the prosthesis to form a covered prosthesis. A first tube is provided that includes an inner diameter and an outer diameter, and the first tube is positioned in a tube expander including a vacuum. A vacuum is applied to the tube expander to expand the inner and outer diameters of the first tube. The covered prosthesis and the mandrel are positioned in the tube expander, and the vacuum is released. The first tube, the covered prosthesis, and the mandrel are removed from the tube expander. A second tube is provided that includes an inner diameter and an outer diameter. The inner diameter of the second tube is smaller than the inner diameter of the first tube. The second tube is positioned over the first tube, and heat is applied to the first and second tubes, the covered prosthesis, and the mandrel. The first and second tubes, the covered prosthesis, and the mandrel are removed from the heat, and the second tube is removed from the first tube, the covered prosthesis, and the mandrel. The first tube is removed from the covered prosthesis and the mandrel, and the mandrel is removed from the covered prosthesis.

These methods provide, among others, the advantages of making a stent or a prosthesis with a covering that conforms to the struts of the stent or prosthesis, has a smooth covering, has no visible creases that form within the covering of the stent of prosthesis, and has a smooth covering that does not distort or deform the struts of the stent or prosthesis.

These methods also provide the advantages of making a stent or other prosthesis with a smooth inner surface and an outer surface that conforms to the struts of the stent or other prosthesis, which is not exposed to blood flow in the body. Therefore, the likelihood of turbulent blood flow and associated stagnation points is reduced with stents or other prosthesis formed by these methods.

At least one unique and important feature of the methods is that the tube used to apply the covering to the stent has a very low durometer on the Shore A or Shore 00 scale. Such low durometer tubes are not standard and not readily or commercially available from manufacturers. These low durometer tubes allow sufficient pressure to be applied to the stent or other prosthesis to displace the tube around the struts of the stent and ensure contact of the inner and outer coverings for increased surface area for bonding the inner and outer coverings without distorting or deforming the stent or other prosthesis.

The accompanying drawings, which are incorporated herein and constitute part of this specification, and, together with the general description give above and the detailed description given below, serve to explain features of the present invention.

BRIEF DESCRIPTION OF THE DRAWINGS

FIG. 1 shows a perspective view of an example of expanding an elastomeric tube by positioning the elastomeric tube in a tube expander to expand the elastomeric tube;

FIG. 2 shows a cross-sectional view of FIG. 1;

FIG. 3 shows a perspective view of wrapping the elastomeric tube around the ends of the tube expander to seal the elastomeric tube to the tube expander;

FIG. 4 shows a cross-sectional view of FIG. 3;

FIG. 5 shows a perspective view of connecting a vacuum source to a port of the tube expander;

FIG. 5A shows an example of rings positioned over the elastomeric tube to seal the elastomeric tube to the tube expander;

FIG. 5B shows an example of caps positioned over the elastomeric tube to seal the elastomeric tube to the tube expander;

FIG. 6 shows a perspective view of applying the vacuum source to the tube expander;

FIG. 7 shows a cross-sectional view of FIG. 6 after the vacuum source has been applied;

FIGS. 8 and 9 show perspective views of positioning a mandrel with a stent with inner and outer coverings in the elastomeric tube in the tube expander;

FIG. 10 shows a cross-sectional view of FIG. 9;

FIG. 10A shows a partial exploded view of FIG. 10;

FIG. 11 shows a perspective view of releasing the vacuum source from the tube expander;

FIG. 12 shows a cross-sectional view of FIG. 11 after the vacuum source has been released;

FIG. 12A shows a partial exploded view of FIG. 12;

FIG. 13 shows a perspective view of removing the elastomeric tube, the mandrel, and the stent with inner and outer coverings from the tube expander;

FIG. 14 shows a cross-sectional view of FIG. 13;

FIG. 15 shows a perspective view of positioning the elastomeric tube, the mandrel, and the stent with inner and outer coverings in a press fixture;

FIG. 15A shows a perspective view of an example of sleeves positioned over the mandrel;

FIG. 16 shows a perspective view of the elastomeric tube, the mandrel, and the stent with inner and outer coverings in the press fixture;

FIG. 17 shows a cross-sectional view of FIG. 16;

FIG. 17A shows a partial exploded view of FIG. 17;

FIG. 18 shows a perspective view of applying heat and pressure to the press fixture;

FIG. 19 shows a cross-sectional view of FIG. 18;

FIG. 19A shows a partial exploded view of FIG. 19;

FIG. 20 shows a perspective view of the elastomeric tube, the mandrel, and the stent after removal from the press fixture;

FIG. 21 shows a cross-sectional view of FIG. 20;

FIG. 22 shows an example of removing the elastomeric tube from the stent by peeling or ripping the elastomeric tube away from the stent;

FIG. 23 shows a side view of the stent after removal of the elastomeric tube;

FIG. 24 shows a side view of removing the mandrel from the stent;

FIG. 25 shows a cross-sectional view of the stent with the layer of the first material and the second material after removal of the mandrel;

FIG. 26 shows a side view of an example of a slit cannula for use in encapsulating a stent with a stent mandrel assembly;

FIG. 27 shows a cross-sectional view of FIG. 26 of a first end of the slit cannula;

FIG. 28 shows a cross-sectional view of FIG. 26 of a second end of the slit cannula;

FIG. 29 shows a perspective view of FIG. 26;

FIG. 30 shows a perspective view of an example of a first mandrel and a second mandrel for insertion within the first and second ends of the slit cannula;

FIG. 31 shows a perspective view of positioning the first mandrel within the first end of the slit cannula;

FIG. 32 shows a perspective view of expanding the slit cannula with the first mandrel;

FIG. 33 shows a perspective view of a first elastomeric tube over a non-expanded portion of the slit cannula;

FIG. 34 shows a perspective view of an inner covering over the elastomeric tube;

FIG. 35 shows a perspective view of a stent over the inner covering and positioning the second mandrel within the second end of the slit cannula;

FIG. 36 shows a perspective view of an outer covering over the stent;

FIG. 37 shows an example of removing handles from the first and second mandrels;

FIG. 38 shows a perspective view of positioning the first and second mandrels, the slit cannula, the first elastomeric tube, and the stent with the inner and outer coverings within a tube expander with a second elastomeric tube;

FIG. 39 shows a perspective view of the first and second mandrels, the slit cannula, the first elastomeric tube, the stent with the inner and outer coverings, and the second elastomeric tube after removal from the tube expander;

FIG. 40 shows a perspective view of FIG. 39 in a press fixture;

FIG. 41 shows a perspective view of FIG. 40 within a heat press;

FIG. 42 shows a perspective view of positioning the first and second mandrels, the slit cannula, the first elastomeric tube, the smooth covered stent, and the second elastomeric tube within a tube expander after applying heat and pressure;

FIG. 43 shows a perspective view of removing the first and second mandrels, the slit cannula, the first elastomeric tube, and the smooth covered stent from the tube expander;

FIG. 44 shows a perspective view of an example of positioning the end caps on the first and second mandrels;

FIG. 45 shows a perspective view of removing the first and second mandrels from the slit cannula and removing the smooth covered stent from the slit cannula;

FIG. 46 shows a perspective view of the smooth covered stent with stripes or indentations on the inner surface of the smooth covered stent;

FIG. 47 shows a perspective view of a third mandrel to be inserted into the smooth covered stent;

FIG. 48 shows a perspective view of the third mandrel with the smooth covered stent and a first elastomeric tube;

FIG. 49 shows a perspective view of the third mandrel, the smooth covered stent, and the first elastomeric tube and a second elastomeric tube;

FIG. 50 shows a perspective view of the third mandrel with the first elastomeric tube and the smooth covered stent with the second elastomeric tube with a press fixture;

FIG. 51 shows a perspective view of FIG. 50 within a heat press;

FIG. 52 shows a perspective view of removing the second elastomeric tube from the first elastomeric tube;

FIG. 53 shows a perspective view of positioning a shrink tube over the first elastomeric tube;

FIG. 54 shows a perspective view of applying heat to the smooth covered stent, the first elastomeric tube, and the shrink tube;

FIG. 55 shows a perspective view of removing the shrink tube form the first elastomeric tube;

FIG. 56 shows a perspective view of the smooth covered stent without the stripes or indentations on the inner surface of the smooth covered stent;

FIG. 57 shows a perspective view of an example of the slit cannula and an example of a single mandrel;

FIG. 58 shows a cross-sectional view of FIG. 57;

FIG. 59 shows a perspective view of the single mandrel within the slit cannula;

FIG. 60 shows a cross-sectional view of FIG. 59;

FIG. 61 shows a perspective view of the slit cannula of FIG. 57 with a second example of a single mandrel;

FIG. 62 shows a cross-sectional view of FIG. 61;

FIG. 63 shows a perspective view of the second example of the single mandrel within the slit cannula;

FIG. 64 shows a cross-sectional view of FIG. 63;

FIG. 65 shows a perspective view of a covered stent positioned on a mandrel;

FIG. 66 shows a perspective view of positioning a first tube in the tube expander;

FIG. 67 shows a perspective view of applying a vacuum source to the tube expander;

FIG. 68 shows a perspective view of positioning the covered stent and the mandrel in the tube expander;

FIG. 69 shows a perspective view of releasing the vacuum source from the tube expander;

FIG. 70 shows a perspective view of the first tube, the covered stent, and the mandrel after removal from the tube expander;

FIG. 71 shows a perspective view of positioning a second tube in the tube expander;

FIG. 72 shows a perspective view of applying a vacuum source to the tube expander;

FIG. 73 shows a perspective view of the covered stent and the mandrel after the first and second tubes are applied to the covered stent;

FIG. 85 shows a perspective view of providing a mandrel with a first layer of elastomeric tube and an inner covering;

FIG. 86 shows a perspective view of the mandrel with the first layer of elastomeric tube and inner covering positioned within the second hollow mandrel of FIG. 77;

FIG. 87 shows a perspective view of removing the second hollow mandrel from beneath the stent to allow the stent to position onto the inner covering, elastomeric tube, and mandrel;

FIG. 88 shows a perspective view of removing the mandrel from beneath the first layer of elastomeric tube;

FIG. 89 shows a perspective view of positioning a support mandrel with holes beneath the first layer of elastomeric tube, positioning the outer covering over the stent to form the covered stent, and positioning the second layer of elastomeric tube over the outer covering;

FIG. 90 shows a transparent perspective view of the support mandrel with holes, the first and second layers of elastomeric tube, and the covered stent;

FIG. 91 shows a transparent perspective view of the support mandrel with holes, the first and second layers of elastomeric tube, and the covered stent and a perspective view of connecting a barb fitting with a cap to first ends of the first and second layers of elastomeric tubes and a tubing line via a barb fitting to second ends of the first and second layers of elastomeric tubes;

FIG. 92 shows a perspective view of positioning the support mandrel with holes, the first and second layers of elastomeric tubes, and the covered stent connected to the tubing line into a press fixture;

FIG. 93 shows a perspective view of the press fixture of FIG. 92 in a closed position.

DETAILED DESCRIPTION OF THE DRAWINGS AND THE PREFERRED EMBODIMENTS

Figure 74:
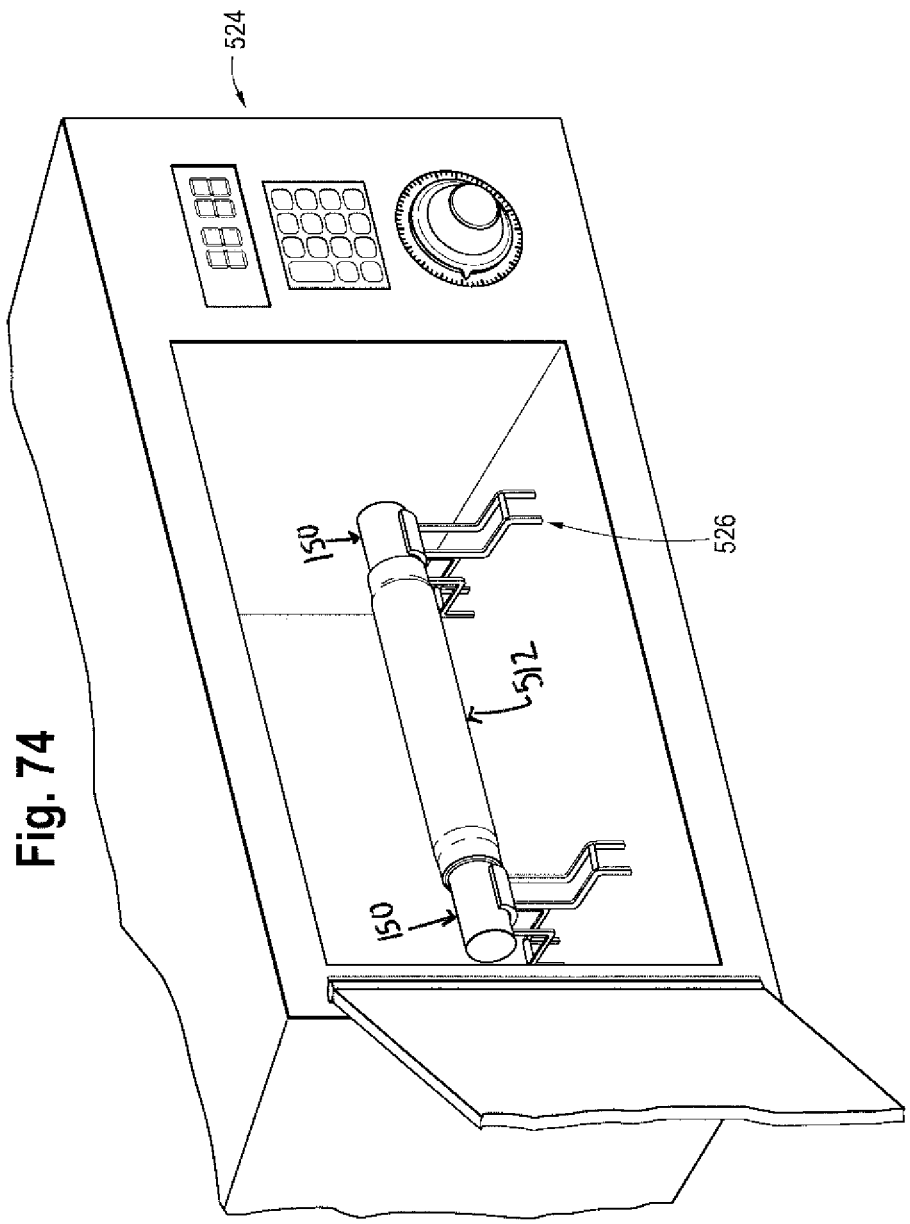
FIG. 74 shows a perspective view of the first and second tubes, the covered stent, and the mandrel on a rack in a heated oven.

In the following detailed description of the various embodiments of methods of making a stent with a smooth covering, like elements and structures are numbered or labeled alike.

Tube Expander with Press Fixture and Heated Press

FIGS. 1-25 illustrate an exemplary method of making a stent 100 with a smooth, uninterrupted covering. The stent 100 has a circular cross-section when expanded with an inner diameter 102, an outer diameter 104, a first end 106, a second end 108, a longitudinal length 110, an inner surface 112, an outer surface 114, and a plurality of struts 115.

The inner and outer diameters 102, 104 of the stent 100 may vary and are measured in the expanded state of the stent 100. For example, the expanded inner diameter 102 may range from 5.0 to 14.0 mm, and in some examples may range from 6.0 to 8.0 mm. When the stent 100 is used in aortic or venous indications, the expanded inner diameter 102 may range 5.0 to 40 mm. The nominal diameter of the stent 100 is defined as the unrestrained diameter of a stent 100 in its expanded form. For balloon-expandable stents, the diameter of the stent 100 is defined by the expanded inner diameter 102 of the stent 100, and the stent 100 in its nominal diameter state may be expanded into the intended vessel size to resist compression. For self-expanding stents, the diameter of the stent 100 is defined by the expanded outer diameter 104 of the stent 100, and the stent 100 will be oversized as compared to the intended vessel to ensure constant outward force against the vessel. The longitudinal length 110 of the stent 100 is defined from the first end 106 to the second end 108 of the stent 100 and will vary depending on the intended vessel for implantation. In one example, the longitudinal length 110 of the stent 100 is 120 mm. When the stent 100 is used in aortic or venous indications, the longitudinal length 110 of the stent 100 may be up to 300 mm.

A tube of elastomeric material 116 provides compression to the stent 100 during an encapsulation process. The elastomeric tube 116 is hollow and includes an inner diameter 118, an outer diameter 120, a first end 122, a second end 124, and a longitudinal length 126. The longitudinal length 126 is defined from the first end 122 to the second end 124 of the elastomeric tube 116. The inner diameter 118 of the elastomeric tube 116 may range from 2 mm to 15 mm. The outer diameter 120 of the elastomeric tube 116 may range from 3 mm to 21 mm.

Suitable materials for the elastomeric material of the tube 116 include silicone, neoprene, latex, butyl rubber, isoprene rubber, natural rubber, Thoralon® or other thermosets, or other known or discovered materials so long as they have the necessary properties described here.

Elastomeric materials are used because they have the capability of resuming their original shape after deformation. Elastomeric materials that have high temperature stability and thus can withstand high temperatures without melting are preferred. For example, silicone has the properties, among others, of high temperature stability, low volatile content, being capable of varying its hardness or softness, and chemical inertness that make it useful. The inventors have discovered that not all elastomeric tubes may be used in the methods here. The inventors have discovered that advantageously the tubes they designed having very low durometer are preferred. In one example, the elastomeric tube 116 includes a specifically designed low durometer silicone, such as MED-4014, MED-4020, or MED-4025 sold by NuSil Technology or other low durometer silicone, such as custom blends of raw silicone, that provide similar mechanical properties. On the shore hardness scale, the durometer of the silicone may range from 10 Shore 00 to 30 Shore A, preferably approximately 15 to 25 Shore A, and preferably 20 Shore A. Depending on the type of low durometer silicone used, the tensile strength may range from approximately 700 psi (4.8 MPa) to 1,400 psi (9.7 MPa), the tear strength is 130 ppi (22.9 kN/m) to 190 ppi (33.5 kN/m), the specific gravity is 1.08 to 1.11, the elongation is 890% to 1,330%, and stress at 200% strain of 40 psi (0.38 MPa) to 105 psi (0.72 MPa).

Another important feature the inventors have discovered is the application of a coating to the inner surface of the elastomeric tube 116. This reduces or eliminates tackiness of the elastomer to which the coating is applied. For example, the coating may include MED-6670 sold by NuSil Technology, MED-6671 sold by NuSil Technology, or a similar friction reducing coating for silicone surfaces. The coating helps to remove the stickiness of the elastomeric tube 116. The coating may include a thickness ranging from 20 to 100 micrometers (μm), or preferably a range of 40 to 50 micrometers (μm). In some examples, the coating may have a higher durometer than the elastomeric tube. In other examples, the durometers may be close or the same. The coating is cured after applying it to the elastomeric tube 116.

In the present method, to radially expand the elastomeric tube 116, the elastomeric tube 116 is positioned within a tube expander 128. FIG. 1 shows a perspective view of the tube expander 128 that includes an opening 130 to receive a port 132. As shown in FIGS. 1, 3 and 4, the port 132 may be positioned within and sealed to the opening 130 of the tube expander 128. The port 132 is configured to receive different sources or inputs, including a vacuum, a syringe, a pressure source, a heat source or other sources.

The tube expander 128 is hollow and includes a shape to conform to the tube and the device. Here it is shown having circular shape with an inner diameter 134, an outer diameter 136, a first end 138, a second end 140, and a longitudinal length 142. The longitudinal length 142 is defined from the first end 138 to the second end 140 of the tube expander 128. The elastomeric tube 116 is positioned through the first and second ends 138, 140 of the tube expander 128. In its original state, the elastomeric tube 116 includes an outer diameter 120 smaller than the inner diameter 134 of the tube expander 128. FIG. 2 shows a cross-sectional view of the elastomeric tube 116 within the tube expander 128.

After positioning the elastomeric tube 116 in the tube expander 128, the first and second ends 122, 124 of the elastomeric tube 116 may be rolled up over the first and second ends 138, 140 of the tube expander 128 to create a seal as shown in FIG. 3. The sealing of the elastomeric tube 116 to the tube expander 128 helps to keep the elastomeric tube 116 in position within the tube expander 128. Other sealing devices or techniques or devices to maintain the position of the elastomeric tube 116 within the tube expander 128 may be used. For example, devices such as rings, sleeves, ties, caps, or other clamping devices may also be positioned over the first and second ends 122, 124 of the elastomeric tube 116 and the first and second ends 138, 140 of the tube expander 128 to maintain the position of the elastomeric tube 116 within the tube expander 128 and to prevent the elastomeric tube 116 from moving along the longitudinal length 142 of the tube expander 128.

FIGS. 5A and 5B show rings 144 and caps 146, respectively, positioned over the first and second ends 122, 124 of the elastomeric tube 116 and the first and second ends 138, 140 of the tube expander 128. FIGS. 2 and 4 show cross-sectional views of the elastomeric tube 116 within the tube expander 128 before any source or input is applied to the tube expander 128.

To radially expand the inner and outer diameters 118, 120 of the elastomeric tube 116, a vacuum may be applied to the tube expander 128. FIG. 5 shows a perspective view of connecting a vacuum source 148 to the port 132 of the tube expander 128. The vacuum source 148 is applied to the tube expander 128 to uniformly expand the inner and outer diameters 118, 120 of the elastomeric tube 116. When the vacuum source 148 is applied, as described previously, the outer diameter 120 of the elastomeric tube 116 seals to the inner diameter 134 of the tube expander 128. This sealing of the elastomeric tube 116 to the tube expander 128 helps to prevent the elastomeric tube 116 from moving along the longitudinal length 142 of the tube expander 128. As shown in FIGS. 6 and 7, when the vacuum source 148 is applied, the outer diameter 120 of the elastomeric tube 116 is in contact with the inner diameter 134 of the tube expander 128.

A mandrel 150 is provided to support the stent 100 or other prosthesis and maintain the nominal diameter of the stent 100 or prosthesis during the covering or encapsulation process. FIG. 8 shows a perspective view of the mandrel 150 that includes a diameter 152, a first end 154, a second end 156, and a longitudinal length 158, which is defined as the length from the first end 154 to the second end 156. The mandrel 150 may be hollow or solid depending on the strength of the material of the mandrel 150 and the heating characteristics or capabilities of the mandrel 150. In some examples, the mandrel 150 may be hollow with an inner diameter 160. When the mandrel 150 is hollow, it may also include a plurality of holes 162. When the mandrel 150 is hollow, heat may be applied internally within the mandrel 150, such as with a cartridge heater, for allow for faster heating. A hollow mandrel 150 also allows for faster cooling. The material of the mandrel 150 may include glass, metal, stainless steel and/or an alloy. When the mandrel is solid, the diameter 152 of the mandrel 150 is smaller than the inner diameter 118 of the elastomeric tube 116 in its expanded state.

An inner covering 164 is provided that is positioned over and wrapped around the mandrel 150 as shown in FIG. 10A. In this example, the inner covering 164 includes a layer 164A of first material 166 and second material 168 that is used for covering the inner surface 112 of the stent 100 or a prosthesis. In an alternative example, the layer 164A of the inner covering 164 only includes the first material 166.

The dimensions of the inner covering 164 will vary depending on the inner diameter 102 and the longitudinal length 110 of the stent 100. For example, the inner covering 164 includes a rectangular or square cross section with a width and a length. The length of the inner covering 64 is the length of the inner covering 164 that wraps around the mandrel 150. The width of the inner covering 164 is the length of the inner covering 164 that extends along the longitudinal length 158 of the mandrel 150. In some examples, the width of the inner covering 164 may range from 1.25 to 6 inches.

The diameter 152 of the mandrel 150 and the inner and outer diameters 118, 120 of the elastomeric tube 116 will also vary depending on the inner and outer diameters 102, 104 of the stent 100. In one example, the diameter 152 of the mandrel 150 is 6.0 mm and the inner diameter 118 of the elastomeric tube 116 is 6.0 mm. In particular, the inner diameter 118 of the elastomeric tube 116 in its original state will vary depending on the outer diameter 104 of the stent 100.

The first material 166 and the second material 168 of the inner covering 164 are parallel to each other within the layer 164A. The inner covering 164 is positioned and wrapped around the mandrel 150 such that when the stent 100 is positioned over the inner covering 164 and the mandrel 150, the inner surface 112 of the stent 100 is completely covered with the inner covering 164. The inner covering 164 is positioned over the mandrel 150 such that the first material 166 is in contact with the mandrel 150 and the second material 168 is not in contact with the mandrel 150. The second material 168 of the inner covering 164 contacts the inner surface 112 of the stent 100 when the stent 100 is positioned over the inner covering 164.

The first material 166 preferably is a thermoplastic or a thermoset material, such as polytetrafluoroethylene (PTFE), including electrospun PTFE (esPTFE) and expanded PTFE (ePTFE), electrospun polymers, and other woven or non-woven polymers. The second material 168 preferably is a thermoplastic material, such as polyurethane, nylon, polyolefins, elastomers, fluorinate ethylene propylene (FEP), styrenic block copolymers (TPE-s), including SEBS, SIBS, SEBS, SEPS, SIS, polyolefin blends (TPE-o), elastomeric alloys (TPE-c or TPV), thermoplastic polyurethanes (TPU), thermoplastic copolyester, and thermoplastic polyamides. Electrospun materials and methods are disclosed in the following patents and patent applications and are incorporated herein by reference: U.S. Pat. Nos. 9,060,852; 8,876,849; 8,795,577; 8,637,109; 8,403,979; 8,211,168; 8,100,683; 7,779,261; 7,678,144; 7,641,844; U.S. Pub. No. 2015-0112383; U.S. Pub. No. 2014-0188212; U.S. Pub. No. 2014-0081386; U.S. Pub. No. 2013-0122248; U.S. Pub. No. 2013-0018220; U.S. Pub. No. 2012-0259170; U.S. Pub. No. 2012-0141656; U.S. Pub. No. 2011-0054512; U.S. Pub. No. 2010-0323052; U.S. Pub. No. 2009-0142505; U.S. Pub. No. 2008-0157444.

The inner covering 164 may include a second layer 164B of both the first material 166 and the second material 168. The inner covering 164 may include one to ten layers of the first material 166 and the second material 168. When more than one layer is used, the layers are positioned over the first layer 164A such that the first and second materials 166, 168 maintain an alternating pattern. For example, the first material 166 of the second layer 164B contacts the second material 168 of the first layer 164A, and the second material 168 of the second layer 164B does not contact either the first material 166 or the second material 168 of the first layer 164A.

The inner covering 164 may be rolled in a sterilized liquid, for example, 70% or 100% isopropanol, ethanol, processed deionized water, or propylene glycol, to assist the inner covering 164 to lay flat against the mandrel 150. Other sterilized liquids may also be used. To keep the inner covering 164 in place, a soldering iron may be used to tack or otherwise adhere edges of the inner covering 164 to the mandrel 150. Other types of adhesion or soldering devices, such as soldering guns and tips, may be used to adhere edges of the inner covering 164. For example, in one example, a soldering station, such as one sold by Weller, may be used with a blunt chisel tip.

The second material 168 may be referred to as a tie layer, a bonding layer or an adhesive because it helps to bond the first material 166 in each of the layers of the inner cover 164 together. The second material 168 may have a lower melting point than the first material 166 to melt and flow through the porous structure of the first material 166 to create a bond between the first materials 166 of the layers 164A, 164B of the inner covering 164. After the inner covering 164 is applied to the mandrel 150, the mandrel 150 and the inner covering 164 include a diameter 170.

In this example, the stent 100 includes a balloon expandable stent. A self-expanding stent may also be used, but a balloon-expanded stent may be preferred in this example. A variety of biocompatible materials may be used to construct the stent, including metals, and/or alloys, medically-acceptable polymers and/or bioabsorbable polymers or materials. For example, the metals and/or alloys may include stainless steel, tantalum, nitinol, tungsten, platinum, inconel, cobalt-chromium alloys, iridium, molybdenum, moly-rhenium, other alloys of nitinol (including ternary and quaternary alloys), and magnesium or its alloys (as degradable stents). If a self-expanding stent it used, other steps may be required to prevent the diameter restriction of the stent 100, including pre-expansion of the stent 100 and cooling of the stent 100 to allow it to be positioned over the inner covering 164.

The inner diameter 102 of the stent 100 is greater than the diameter 170 of the mandrel 150 and the inner covering 164 such that the stent 100 may slide over the mandrel 150 and the inner covering 164. As shown in FIG. 10A, the stent 100 is positioned over the inner covering 164 and the mandrel 150 and is in contact with the second material 168 of the inner covering 164. A crimper, such as an iris crimper, or other reducing device may be used to uniformly secure the stent 100 in place over the inner covering 164 and the mandrel 150. The stent 100 is approximately at its nominal diameter when positioned over the mandrel 150 and the inner covering 164, as well as after use of the crimper.

After the stent 100 is positioned over the inner covering 164 and the mandrel 150, in this example, an outer covering 172 is provided that includes a layer 172A of the first material 166 and the second material 168 that are parallel to each other within the layer 172A. In an alternative example, the layer 172A of the outer covering 172 only includes the first material 166. The outer covering 172 may be positioned over and wrapped around the stent 100 such that the second material 168 of the outer covering 172 is in contact with the stent 100 and the first material 166 is not in contact with the stent 100. The outer covering 172 is positioned over and wrapped around the stent 100 such that the outer surface 114 of the stent 100 is completely covered with the outer covering 172.

As with the inner covering 164, the outer covering 172 may include a second layer 172B of both the first material 166 and the second material 168. The outer covering 172 may include one to ten layers of the first material 166 and the second material 168. When more than one layer is used, the layers are positioned over the first layer 172A such that the first and second materials 166, 168 maintain an alternating pattern as described previously with the inner covering 164. For example, the second material 168 of the second layer 172B contacts the first material 166 of the first layer 172A, and the first material 166 of the second layer 172B does not contact either the first material 166 or the second material 168 of the first layer 172A.

As described previously with the inner covering 164, the outer covering 172 may be rolled in a sterilized liquid, for example, 70% or 100% isopropanol, ethanol, processed deionized water, or propylene glycol, to assist the outer covering 172 to lay flat against the stent 100. Other sterilized liquids may also be used. Also, other types of adhesion or soldering devices, such as soldering guns and tips, may be used to adhere edges of the outer covering 172.

After the outer covering 172 is applied to the stent 100, the inner surface 112 of the stent 100 is covered with the inner covering 164 and the outer surface 114 of the stent 100 is covered with the outer covering 172, resulting in covered stent 174. The covered stent 174 and the mandrel 150 include a diameter 176. The inner diameter 128 of the elastomeric tube 116 is smaller than or the same as the diameter 176.

The covered stent 174 and the mandrel 150 are then positioned within the lumen of the expanded elastomeric tube 116 in the tube expander 128 such that the elastomeric tube 116 covers the covered stent 174 as shown in FIGS. 8 and 9. For example, the longitudinal length 126 of the elastomeric tube 116 is greater than or the same as the longitudinal length 110 of the stent 100. FIGS. 10 and 10A show cross-sectional views of the elastomeric tube 116, the covered stent 174, and the mandrel 150 within the tube expander 128 when the elastomeric tube 116 is in its expanded state. Once the mandrel 150 is in position, as shown in FIG. 11, the vacuum source 148 may be released so that the elastomeric tube 116 recovers to the covered stent 174 and surrounds the covered stent 174. FIGS. 12 and 12A show cross-sectional views of the elastomeric tube 116, the covered stent 174, and the mandrel 150 in the tube expander 128 after the release of the vacuum source 148. After the release of the vacuum source 148, the outer diameter 120 of the elastomeric tube 116 is smaller than the inner diameter 134 of the tube expander 128.

After the vacuum source is released allowing the elastomeric tube 116 to recover to the covered stent 174, the elastomeric tube 116, the covered stent 174, and the mandrel 150 are removed from the tube expander 128 as shown in FIG. 13. The elastomeric tube 116, the covered stent 174, and the mandrel 150 together include a diameter 178. FIG. 14 shows a cross-sectional view of the mandrel 150, the covered stent 174, and the elastomeric tube 116 after removal from the tube expander 128. Pressure and heat are then applied to uniformly encapsulate and compress the inner and outer coverings 164, 172 and the stent 100 together.

In one example, after removal of the mandrel 150, the covered stent 174, and the elastomeric tube 166 from the tube expander 128 and prior to applying pressure and heat, the mandrel 150, the covered stent 174, and the elastomeric tube 166 may be placed in a vacuum chamber for a pretreatment vacuum step. The pretreatment vacuum step may remove any air bubbles from the elastomeric tube 166. Air bubbles within the elastomeric tube 166 may affect heating and bonding of the inner and outer coverings 164, 172 to the stent 100. The vacuum chamber may be any vacuum chamber known in the art, and the mandrel 150 may be positioned on a rack in the vacuum chamber to provide uniform distribution of the pressure around the elastomeric tube 166. In one example, the vacuum pressure applied may be approximately 500 to 700 mmHg (vacuum pressure) may be applied for approximately 15 minutes to two (2) hours. In another example, the vacuum pressure applied may be approximately 600 mmHg (absolute vacuum pressure) for approximately 1 hour. The vacuum pressure applied may vary and may range from approximately 50 mmHg to 760 mmHg (absolute vacuum pressure), and as the vacuum pressure applied increases, the time the vacuum pressure will be applied decreases.

To apply pressure and heat to uniformly encapsulate and compress the inner and outer coverings 164,172 and the stent 100 together, in one example, as shown in FIG. 15A, a sleeve or cap 180 that is hollow and includes an inner diameter 182 and an outer diameter 184 may be positioned on each of the first and second ends 154, 156 of the mandrel 150. The inner diameter 182 of the sleeve 180 is the same or slightly larger than the diameter 152 of the mandrel 150 such that the sleeves 180 may slide along the mandrel 150 to contact the first and second ends 122, 124 of the elastomeric tube 116. The sleeves 180 help to prevent or minimize the longitudinal length 126 of the elastomeric tube 116 from expanding when pressure, heat and/or compression are applied and help with heat transfer. The sleeves 180 may include metal and/or alloys.

To apply pressure and heat, in one example as shown in FIG. 15, the mandrel 150 with the covered stent 174, and the elastomeric tube 116 are positioned in a press fixture 186. The press fixture 186 includes a first portion 188 and a second portion 190. The first and second portions 188, 190 each include a slot 192 for receiving the mandrel 150 with the covered stent 174, and the elastomeric tube 116. The slots 192 each include a half circular cross-section such that when the first and second portions 188, 190 connect, or the press fixture is closed, the slots 192 form a hollow circle with a diameter 194. The diameter 194 is the same as or smaller than the diameter 178 of the mandrel 150, the covered stent 174, and the elastomeric tube 116 together. In other words, the diameter 178 is the same or slightly larger than the diameter 194 of the press fixture 186. Preferably, the diameter 178 is slightly larger than the diameter 194 of the press fixture 186 such that the first and second portions 188, 190 of the press fixture 186 do not contact each other when brought together until compression is applied to the press fixture 186. The press fixture 186 may include multiple slots 192 with varying diameters 194.

As shown in FIGS. 16 and 17, after positioning the mandrel 150 with the covered stent 174 and the elastomeric tube 116 in one of the slots 192 of the press fixture 186, the first and second portions 188, 190 are brought together. The press fixture 186 is not completely closed when the first and second portions 188, 190 are brought together because the diameter 178 is larger than the diameter 194 of the slots 192 of the press fixture 186. Thus, the first and second portions 188, 190 may not contact each other until compression is applied to the press fixture 186. FIGS. 17 and 17A show cross-sectional views of the mandrel 150, the covered stent 174, and the elastomeric tube 116 within the press fixture 186 before compression is applied.

As shown in FIG. 18, the press fixture 186 with the mandrel 150, the covered stent 174, and the elastomeric tube 116 are then positioned in a heated press 196, such as those sold by Carver, Inc., to uniformly apply compression and heat to the elastomeric tube 116 and the covered stent 174. When pressure is applied to the heated press 196, the pressure compresses the press fixture 196, which compresses the elastomeric tube 116 uniformly against the covered stent 174 and displaces the elastomeric tube 116 to ensure contact between the inner and outer coverings 164, 172 as shown in FIG. 19A. Heat is also applied to the press fixture 186 to uniformly melt the second material 168 of the inner and outer coverings 164, 172 to bond the first material 166 of the inner and outer coverings 164, 172 together around the struts 115 of the stent 100.

The amount of pressure applied may also vary, and in one example, is applied until a pressure gauge on the heated press 196 moves slightly or until the first and second portions 188, 190 contact each other. The amount of pressure applied depends on the size and durometer of the elastomeric tube 116, as more pressure will need to be applied to thicker and higher durometer elastomeric tubes 116. For example, rather than measuring the amount of pressure, the displacement of the thickness of the elastomeric tube 116 may be measured. The displacement of the thickness of the elastomeric tube 116 allows the elastomeric tube 116 to conform around struts 115 of the stent 100. The displacement may range from approximately 0.002 to 0.050 inches, and preferably will range from approximately 0.005 to 0.010 inches.

The amount of heat applied may vary depending on the material of the second material 168. For example, when the second material 168 is polyurethane, the heat temperature may range from 380±5 to 430±5 degrees Fahrenheit, and preferably is 390±5 degrees Fahrenheit. When the second material 168 is fluorinated ethylene propylene (FEP), the heat temperature may range from 490±5 to 540±5 degrees Fahrenheit, and preferably is 500±5 degrees Fahrenheit. The amount of heat applied should be sufficient to melt the second material 168 of the inner and outer coverings 164, 172 and will vary depending on the type of second material 168 used. When the inner and outer coverings 164, 172 only include the first material 166, the inner and outer coverings 164, 172 are heated to above the glass transition temperature of the first material 166.

The pressure applied minimizes the diameter 178 of the mandrel 150 with the covered stent 174, and the elastomeric tube 116 together to be the same as the diameter 194 of the slots 192 of the press fixture 186 and compresses the elastomeric tube 116 against the covered stent 174 in a uniform distribution around the elastomeric tube 116. The pressure and heat may be applied for a time of one minute. However, the time that the pressure and heat are applied may increase or decrease depending on the amount of pressure and heat necessary to displace the thickness of the elastomeric tube 116 to conform around the struts 115 of the stent 100 and melt the second material 168 of the inner and outer coverings 164, 172.

Alternatively, pressure may be applied to the press fixture 186 by compression molding or an alternative pressure source that would permit even pressure distribution around the elastomeric tube 116 and the covered stent 174. Also, heat may also be applied through the mandrel 150, such as described previously with a cartridge heater, if the mandrel 150 is hollow, to heat the covered stent 174 to melt the second material 168 of the inner and outer coverings 164, 172.

The application of heat and pressure to the covered stent 174 uniformly encapsulates the stent 100 with the inner and outer coverings 164, 172 to form a smooth covered stent 198. The smooth covered stent 198 includes no visible creases, and the inner and outer coverings 164, 172 include no creases or ridges that create distortions or lack of continuity on the inner and outer coverings 164, 172. The press fixture 196 and the elastomeric tube 116 permit uniform pressure and heat distribution around the covered stent 174. FIG. 19A shows a cross-sectional view of the mandrel 150, the smooth covered stent 198, and the elastomeric tube 116 after the heat and pressure are applied for a specific time. After the heat and pressure are applied, the press fixture 186 is removed from the heated press 196 and the elastomeric tube 116, the smooth covered stent 198, and the mandrel 150 are removed from the press fixture 186. The elastomeric tube 116, the smooth covered stent 198, and the mandrel 150 may be placed in room temperature water to cool, blown with compressed air to cool, allowed to cool to room temperature of the air, or cooled with freeze spray or liquid nitrogen.

In one example, the elastomeric tube 116 may be removed from the smooth covered stent 198 by positioning the elastomeric tube 116, the smooth covered stent 198, and the mandrel 150 through the tube expander 128. The first and second ends 122, 124 of the elastomeric tube 116 may be rolled up over the first and second ends 138, 140 of the tube expander 128 to create a seal. As discussed above, sealing devices or techniques to maintain the position of the elastomeric tube 116 within the tube expander 128 may be used.

Figure 75:
FIG. 75 shows a microscopic view of the smooth covered stent.
Figure 76:
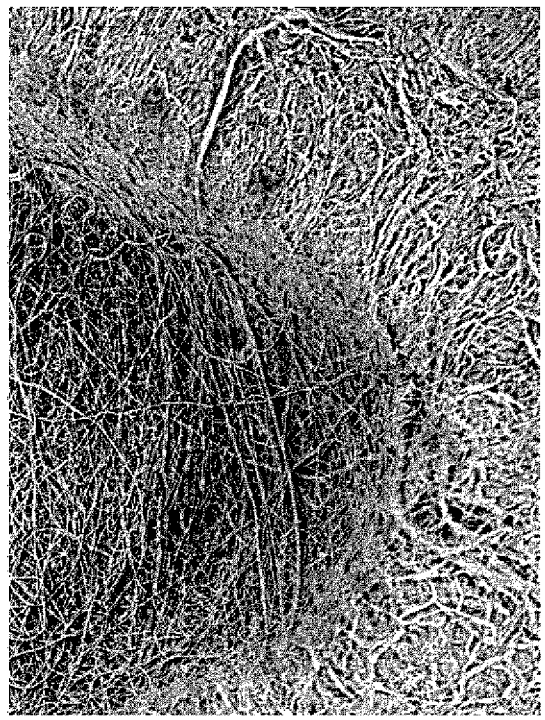
FIG. 76 shows a microscopic view of the smooth covered stent.

The vacuum source 148 is applied to the tube expander 128 to uniformly expand the inner and outer diameters 118, 120 of the elastomeric tube 116. The vacuum source 128 causes the inner and outer diameters 118, 120 of the elastomeric tube 116 to uniformly expand so that the outer diameter 120 of the elastomeric tube 116 is in contact with the inner diameter 134 of the tube expander 128. The smooth covered stent 198 and the mandrel 150 are removed from the tube expander 128, and the vacuum source 148 is released to allow the elastomeric tube 116 to recover. The mandrel 150 is then removed from the smooth covered stent 198 as shown in FIGS. 23 and 24. FIGS. 75 and 76 show microscopic views of the smooth covered stent 198, and the outer covering 172 conforming around struts of the stent 100.

During the encapsulation process, the inner and outer diameters 102, 104 of the stent 100 remain approximately the same to maintain integrity of the stent 100. Thus, from the beginning of the encapsulation process, when the stent 100 is positioned over the inner covering 164, until the end of the encapsulation process, when the smooth covered stent 198 is formed, the stent 100 maintains its nominal diameter.

In an alternative example, if a self-expanding stent is used, a second elastomeric tube may be positioned around the mandrel 150 via the tube expander 128 including the vacuum 148, as described previously above, prior to placement of the inner covering 164 over the mandrel 150. After placement of the second elastomeric tube around the mandrel 150, tension is applied to the second elastomeric tube to radially decrease the outer diameter of the second elastomeric tube to allow the stent 100 to slide or otherwise be positioned over the second elastomeric tube on the mandrel 150. Specifically, the tension applied outer diameter of the second elastomeric tube is less than the inner diameter 102 of the stent 100. The tension may be applied by using clamps to pull on the ends of the second elastomeric tube. With the tension applied to the second elastomeric tube on the mandrel 150, the inner covering 164 is positioned over and wrapped around the second elastomeric tube with the first material 166 of the inner covering 164 in contact with the second elastomeric tube, as described previously. The stent 100 is positioned over the inner covering 164 and in contact with the second material 168 of the inner covering 164. After the stent 100 is positioned over the inner covering 164, the tension applied to the second elastomeric tube may be released and the clamps removed. When the tension is released, the second elastomeric tube radially expands to a non-tension applied state. After expansion, the inner covering 164 contacts the inner diameter 102 of the stent 100, and the stent 100 maintains its nominal diameter and is not significantly expanded. The subsequent steps described above to form the smooth covered stent 198 may then be applied, including without limitation the application of an outer covering 172, the application of the elastomeric tube 116, and the application of heat and pressure using a press fixture 186 and heated press 196.

The tables and steps below provide examples of the materials and steps using the aforementioned method.

Example 1: Balloon-Expandable Stent and Inner and Outer Coverings Including First and Second Materials

| Element | Specifications |
| --- | --- |
| Stent 100 | Inner diameter 102 is 6.0 mm, outer diameter 104 is 6.4 mm, nominal diameter is 6 mm, longitudinal length 110 is 30 mm, balloon-expandable |
| Elastomeric tube 116 | inner diameter 118 is 6 mm, outer diameter 120 is 8 mm, longitudinal length 126 is 75 mm, and the material is silicone with a durometer of 20-25 Shore A |
| Coating | MED-6670, thickness is 45 µm |
| Tube expander 128 | inner diameter 134 is 14 mm |
| Inner covering 164 | includes first material 166 and second material 168 |
| First material 166 | esPTFE |
| Second material 168 | polyurethane |
| Outer covering 172 | includes first material 166 and second material 168 |
| Mandrel 150 | diameter is 6 mm, the material is glass with smooth finish |
| Slot 192 of Press Fixture 186 | diameter 194 of slot 192 is 8 mm |

Steps:
- The coating is applied to the inner diameter 118 of the elastomeric tube 116 and then cured;
- The elastomeric tube 116 is positioned within the tube expander 128 including the port 128 and the vacuum 148;
- The mandrel 150 is provided;
- The inner covering 164 is rolled in 70% isopropanol;
- The inner covering 164 is positioned or wrapped around the mandrel 150 with the first material 166 in contact with the mandrel 150;
- The stent 100 is initially slightly over-expanded and then positioned over the inner covering 164 and in contact with the second material 168 of the inner covering 164;
- An Iris crimper is used to secure the stent 100 to the inner covering 164;
- The outer covering 172 is rolled in 70% isopropanol;
- The outer covering 172 is positioned or wrapped around the stent 100 with the second material 168 of the outer covering 172 in contact with the stent 100 to form the covered stent 174;
- The first and second ends 122, 124 of the elastomeric tube 116 are rolled up and wrapped around the first and second ends 138, 140 of the tube expander 128;
- The vacuum 148 is applied expanding the inner and outer diameters 118, 120 of the elastomeric tube 116 until the outer diameter 120 of the elastomeric tube 116 contacts the inner diameter 134 of the tube expander 128;
- The covered stent 174 and the mandrel 150 are positioned in the tube expander 128;
- The vacuum 148 is released allowing the inner and outer diameters 118, 120 of the elastomeric tube 116 to retract to an unexpanded state and recover to the covered stent 174;

The elastomeric tube 116, the covered stent 174, and the mandrel 150 are positioned in a vacuum chamber with an applied pressure of 600 mmHg (absolute vacuum pressure) for 1 hour;

The elastomeric tube 116, the covered stent 174, and the mandrel 150 are removed from the vacuum chamber and positioned in the slot 192 of the press fixture 186 and the first and second portions 188, 190 of the press fixture 186 are brought together;

The press fixture 186 is positioned in the heated press 196;

Pressure is applied to the press fixture 186 to displace the thickness of elastomeric tube 116 by 0.005±0.001 inches;

Heat is applied to the press fixture 186 to 390±5 degrees Fahrenheit and is applied for 1 minute time;

The press fixture 186 is removed from the heated press 196;

The elastomeric tube 116, the smooth covered stent 198, and the mandrel 150 are removed from the press fixture 186 and positioned in room temperature water for cooling;

The elastomeric tube 116, the smooth covered stent 198, and the mandrel 150 are positioned in the tube expander 128;

The first and second ends 122, 124 of the elastomeric tube 116 are rolled up and wrapped around the first and second ends 138, 140 of the tube expander 128;

The vacuum 148 is applied allowing the inner and outer diameters 118, 120 of the elastomeric tube 116 to uniformly expand;

The smooth covered stent 198 and the mandrel 150 are removed from the tube expander 128; and The mandrel 150 is removed from the smooth covered stent 198.

Example 2: Balloon-Expandable Stent and Inner and Outer Coverings Including First Material

| Element | Specifications |
| --- | --- |
| Stent 100 | Inner diameter 102 is 8.0 mm, outer diameter 104 is 8.4 mm, nominal diameter is 8 mm, longitudinal length 126 is 30 mm, balloon-expandable |
| Elastomeric tube 116 | inner diameter 118 is 8 mm, outer diameter 120 is 10 mm, longitudinal length 126 is 75 mm, and the material is silicone with a durometer of 20 Shore A |
| Coating | MED-6670, thickness is 45 μm |
| Tube expander 128 | inner diameter 134 is 14 mm |
| Inner covering 164 | includes first material 166 only |
| First material 166 | esPET |
| Outer covering 172 | includes first material 166 only |
| Mandrel 150 | diameter is 8 mm, the material is stainless steel |
| Slot 192 of Press Fixture 186 | diameter 194 of slot 192 is 10 mm |

Steps:
The coating is applied to the inner diameter 118 of the elastomeric tube 116 and then cured;
The elastomeric tube 116 is positioned within the tube expander 128 including the vacuum 148;
The mandrel 150 is provided;
The inner covering 164 is rolled in 70% isopropanol;
The inner covering 164 is positioned or wrapped around the mandrel 150;
The stent 100 is initially slightly over-expanded and then positioned over the inner covering 164;
An Iris crimper is used to secure the stent 100 to the inner covering 164;
The outer covering 172 is rolled in 70% isopropanol;
The outer covering 166 is positioned or wrapped around the stent 100 to form the covered stent 174;
The first and second ends 122, 124 of the elastomeric tube 116 are rolled up and wrapped around the first and second ends 138, 140 of the tube expander 128;
The vacuum 148 is applied expanding the inner and outer diameters 118, 120 of the elastomeric tube 116 until the outer diameter 120 of the elastomeric tube 116 contacts the inner diameter 134 of the tube expander 128;
The covered stent 174 and the mandrel 150 are positioned in the tube expander 128;
The vacuum 148 is released allowing the inner and outer diameters 118, 120 of the elastomeric tube 116 to retract to an unexpanded state and recover to the covered stent 174;
The elastomeric tube 116, the covered stent 174, and the mandrel 150 are positioned in a vacuum chamber with an applied pressure of 600 mmHg (absolute vacuum pressure) for 1 hour;
The elastomeric tube 116, the covered stent 174, and the mandrel 150 are removed from the vacuum chamber and positioned in the slot 192 of the press fixture 186 and the first and second portions 188, 190 of the press fixture 186 are brought together;
The press fixture 186 is positioned in the heated press 196;
Pressure is applied to the press fixture 186 to displace the thickness of elastomeric tube 116 by 0.005±0.001 inches;
Heat is applied to the press fixture 186 to 365±5 degrees Fahrenheit and is applied for 1 minute time;
The press fixture 186 is removed from the heated press 196;
The elastomeric tube 116, the smooth covered stent 198, and the mandrel 150 are removed from the press fixture 186 and positioned in room temperature water for cooling;
The elastomeric tube 116, the smooth covered stent 198, and the mandrel 150 are positioned in the tube expander 128;
The first and second ends 122, 124 of the elastomeric tube 116 are rolled up and wrapped around the first and second ends 138, 140 of the tube expander 128;
The vacuum 148 is applied allowing the inner and outer diameters 118, 120 of the elastomeric tube 116 to uniformly expand;
The smooth covered stent 198 and the mandrel 150 are removed from the tube expander 128; and
The mandrel 150 is removed from the smooth covered stent 198.

Manual Removal of the Elastomeric Tube

In another example, as shown in FIG. 22, the elastomeric tube 116 may be removed from the smooth covered stent 198 by ripping or peeling the elastomeric tube 116 away from the smooth covered stent 198. The elastomeric tube 116 may also be removed by skiving or pulling the elastomeric tube 116 along a longitudinal length 200 of the smooth covered stent 198. The mandrel 150 is removed from the smooth covered stent 198 as shown in FIGS. 23 and 24. FIG. 25 shows a cross-sectional view of the smooth covered stent 198. If the longitudinal length 200 of the smooth covered stent 198 exceeds beyond the desired length, any excess on a first end 202 and second end 204 of the smooth covered stent 198 may be trimmed, cut, or otherwise removed.

Swelling Agent for Radial Expansion of Elastomeric Tube

Another example of expanding the inner and outer diameters 118, 120 of the elastomeric tube 116 includes placing the elastomeric tube 116 in a container including a swelling agent. The container may include a glass vial or any other container capable of holding a liquid. The swelling agent may include hexane, volatile methyl siloxane, Freon®, Swellex®, Swellex® P, or other swelling agents.

The elastomeric tube 116 remains in the container with the swelling agent until the elastomeric tube 116 is adequately expanded so that the inner diameter 118 of the elastomeric tube 116 is greater than the diameter 170 of the mandrel 150 and the covered stent 174. Thus, the time the elastomeric tube 116 remains in the container with the swelling agent may vary, and may include approximately ten minutes.

The elastomeric tube 116 is then removed from the container, and the mandrel 150 and the covered stent 174 may be positioned within the elastomeric tube 116 such that the elastomeric tube 116 surrounds the covered stent 174. For example, the longitudinal length 126 of the elastomeric tube 116 is greater than or the same as the longitudinal length 110 of the stent 100. The elastomeric tube 116, the mandrel 150, and the covered stent 174 are allowed to air dry under a fume hood, exposed to a dryer, such as an electric dryer, or otherwise permitted to dry to allow the elastomeric tube 116 to recover to the covered stent 174. Heat and pressure are then applied to the covered stent 174 as described previously including the press fixture 186 and the heated press 196 to uniformly form the smooth covered stent 198.

After the heat and pressure are applied, the press fixture 186 is removed from the heated press 196, and the mandrel 150, the smooth covered stent 198, and the elastomeric tube 116 are removed from the press fixture 186. The elastomeric tube 116 may then be removed from the smooth covered stent 198 by any of the methods previously described including by ripping or peeling the elastomeric tube 116 away from the smooth covered stent 198, by using the tube expander 128 to uniformly expand the inner and outer diameters 118, 120 of the elastomeric tube 116 away from the smooth covered stent 198, or by placing elastomeric tube 116, the smooth covered stent 198, and the mandrel 150 in the container with the swelling agent to uniformly expand the inner and outer diameters 118, 120 of the elastomeric tube 116 away from the smooth covered stent 198. After the elastomeric tube 116 is removed from the smooth covered stent 198, the mandrel 150 is then removed from the smooth covered stent 198.

Expansion Mandrels and Slit Cannula

FIGS. 26-64 show another example of a method of making a stent with a smooth covering. A slit cannula 300 is provided that is hollow and includes a circular cross section with an inner diameter 302, an outer diameter 304, a first end 306, a second end 308, and a longitudinal length 310, which is defined from the first end 306 to the second end 308 as shown in FIG. 26. The material of the slit cannula 300 is polytetrafluoroethylene (PTFE), including Teflon®, stainless steel or another material that is capable of withstanding the pressure and temperature without material failure.

In this example, the stent 100 includes a self-expanding stent. However, a balloon-expandable stent may also be used. A variety of biocompatible materials may be used to construct the stent, including metals, and/or alloys, medically-acceptable polymers and/or bioabsorbable polymers or materials. For example, the metals and/or alloys may include stainless steel, tantalum, nitinol, tungsten, platinum, inconel, cobalt-chromium alloys, iridium, molybdenum, moly-rhenium, other alloys of nitinol (including ternary and quaternary alloys), and magnesium or its alloys (as degradable stents).

The slit cannula 300 also includes a plurality of slits 312. The slits 312 include a first end 314, a second end 316, and a longitudinal length 318, which is defined from the first end 314 to the second end 316. The longitudinal length 318 of the slits 312 is smaller than the longitudinal length 310 of the slit cannula 300. The slits 312 allow radial expansion of the slit cannula 300 and the inner and outer diameters 302, 304 of the slit cannula 300 to increase.

In one example, as shown in FIGS. 26-32, the first ends 314 of the slits 312 begin either at the first or second ends 306, 308 of the slit cannula 300. The second ends 316 of the slits 312 do not interact with either the first or second ends 306, 308 of the slit cannula 300. The second ends 316 of the slits 312 each include a circular end 320. The circular ends 320 provide stress relief and release on the slits 312 during expansion of the slit cannula 300 and prevent the longitudinal length 318 of the slits 312 from increasing and thereby extending the second ends 316 of the slits 312 to either the first or second ends 306, 308 of the slit cannula 300.

The slits 312 form an alternating pattern around the outer diameter 304 of the slit cannula 300 such that if the first end 314 of one of the slits 312 begins at the first end 306 of the slit cannula 300, the first end 314 of the adjacent slits 312 begins at the second end 308 of the slit cannula 300. For example, as shown in FIGS. 26-32, the slit cannula 300 includes twelve slits 312. In other examples, 8 to 10 slits may be used depending on the outer diameter 104 of the stent 100. FIG. 27 shows a cross-sectional view of the first end 306 of the slit cannula 300, and FIG. 28 shows a cross-sectional view of the second end 308 of the slit cannula 300. The number of slits 312 will vary depending on the inner and outer diameters 302, 304 of the slit cannula 300.

The inner and outer diameters 302, 304 of the slit cannula 300 will vary depending on the nominal diameter of the stent 100. For example, the nominal diameter of the stent 100 may range from 5-14 mm. When the stent 100 is used in aortic or venous indications, the expanded outer diameter 104 may range 5.0 to 40 mm. The inner diameter 302 of the slit cannula 300 may range from 2.16±0.13 to 5.33±0.13 mm, and the outer diameter 304 may range from 3.175±0.13 to 6.35±0.13 mm.

In one example, as shown in FIGS. 30-32, a first mandrel 322 is provided as a support base for the slit cannula 300. The material of the first mandrel 322 includes glass, metal, stainless steel or an alloy, and preferably stainless steel. As shown in FIG. 32, when the first mandrel 322 is fully inserted within the slit cannula 300, the portion of the slit cannula 300 covering the first mandrel 322 is expanded. The first mandrel 322 includes a circular cross-section with a first portion 323 and a second portion 325. The first portion 323 includes a diameter 324, and the second portion 325 includes a diameter 327. The diameter 324 of the first portion 323 is greater than the diameter 327 of the second portion 325. In an alternative example, the first mandrel 322 may be hollow to allow for faster heating and cooling or alternative methods of heating and cooling underneath the stent 100.

The first mandrel 322 includes a first end 326, a second end 328, a tip 330, and a longitudinal length 332, which is defined from the first end 326 to the second end 328 of the first mandrel 322. The longitudinal length 332 of the first mandrel 322 is smaller than the longitudinal length 310 of the slit cannula 300. The tip 330 is located at the first end 326 of the first mandrel 322. In an alternative example, the first mandrel 322 may be permanently fixed with the slit cannula to provide stability.

As shown in FIGS. 30-32, in one example, the first mandrel 322 includes a handle 334. The handle 334 has a circular cross section, a first end 336, a second end 338, and a slot 340 that has a circular cross section for receiving the second portion 325 of the first mandrel 322. For example, when the diameter 327 of the second portion 325 is 0.1250±0.005 inches, the diameter of the slot 340 of the handle 334 is 0.1260±0.005 inches. The handle 334 slides onto the second portion 325 and is attached to the first mandrel 322 by a press fit and/or other fastening means that permit the handle 334 to be easily removed from the first mandrel 322. In an alternative example, the first mandrel 322 does not include a handle 334. In another example, the second portion 325 of the first mandrel 322 is knurled or machined to allow for gripping or handling of the first mandrel 322. The material of the handle 334 includes glass, metal, stainless steel or an alloy, and preferably stainless steel.

A first layer of elastomeric tube 342 is provided and positioned over a non-expanded portion of the slit cannula 300 as shown in FIG. 33. As described previously, the elastomeric material of the tube 342 may include the same material as the elastomeric tube 116 or, preferably, an elastomeric material with a higher durometer than the elastomeric tube 116. The elastomeric tube 342 includes an inner diameter 344, an outer diameter 346, and a thickness 345, which is defined from the inner diameter 344 to the outer diameter 346. In its original state, the inner diameter 344 of the elastomeric tube 342 is slightly smaller than the outer diameter 304 of the slit cannula 300. The inner and outer diameters 344, 346 will vary depending on the nominal diameter of the stent 100. For example, the nominal diameter of the stent 100 may range from 5 to 14 mm. The outer diameter 346 may range from 0.130±0.005 to 0.524±0.005 inches. The inner diameter 344 may range from 0.090±0.005 to 0.484±0.005 inches. When the stent 100 is used in aortic or venous indications, the expanded outer diameter 102 may range 5.0 to 40 mm. The first layer of elastomeric tube 342 is hollow and includes a first end 348, a second end 350, and a longitudinal length 352. The longitudinal length 352 is defined from the first end 348 to the second end 350 of the elastomeric tube 342 and is the same as or slightly smaller than the longitudinal length 310 of the slit cannula 300.

The inner covering 164 including the first material 166 and the second material 168, as described previously, that is used to cover the inner surface 112 of the stent 100 or a prosthesis, is positioned over and wrapped around the first layer of elastomeric tube 342 as shown in FIG. 34. The first material 166 is in contact with the first layer of the elastomeric tube 342. The stent 100 is then positioned over the inner covering 164 and is in contact with the second material 168 of the inner covering 164.

As described previously, the inner covering 164 may include more than one layer such that the first and second materials 166, 168 of the inner covering 164 to maintain an alternating pattern underneath the stent 100. To keep the layers in place, as previously described, a soldering iron may be used to tack or otherwise adhere edges of the inner covering 164. In other examples, the first mandrel 322 is provided after the first layer of elastomeric tube 342, the inner covering 164, and the stent 100 are positioned over the slit cannula 300.

A coating, as previously described, that reduces the friction on the surface of the first layer of elastomeric tube 342 may be applied to the outer diameter 346 of the first layer elastomeric tube 342. The coating helps to remove the stickiness or tackiness of the first layer of elastomeric tube 342, so that the first layer of elastomeric tube 342 does not stick to the inner covering 164.

As shown in FIG. 35, a second mandrel 354 is provided to expand the slit cannula 300, the first layer of elastomeric tube 342, and the inner covering 164. The material of the second mandrel 354 includes glass, metal, stainless steel or an alloy, and preferably stainless steel. After expansion, the inner covering 164 contacts the inner diameter 102 of the stent 100, and the stent 100 maintains its nominal diameter and is not significantly expanded.

The second mandrel 354 includes a circular cross-section with a first portion 356 and a second portion 358. The first portion 356 includes a diameter 360, and the second portion 358 includes a diameter 362. The diameter 360 of the first portion 356 is greater than the diameter 362 of the second portion 358. The second mandrel 354 includes a first end 364, a second end 366, a tip 368, and a longitudinal length 370, which is defined from the first end 364 to the second end 366 of the second mandrel 356. The longitudinal length 370 of the second mandrel 354 is smaller than the longitudinal length 310 of the slit cannula 300. The tip 368 is located at the first end 364 of the second mandrel 354. In an alternative example, the second mandrel 354 may be permanently fixed with the slit cannula to provide stability. In an alternative example, the first mandrel 322 may be hollow to allow for faster heating and cooling or alternative methods of heating and cooling underneath the stent 100.

When the second mandrel 354 is fully inserted within the slit cannula 300, the portion of the slit cannula 300 that covers the second mandrel 354 and the stent 100 is expanded, and the tip 368 of the second mandrel 354 is in contact with the tip 330 of the first mandrel 322. As shown in FIG. 36, the second mandrel 354 extends beneath the longitudinal length 110 of the stent 100 so the first layer of elastomeric tube 342 and the inner covering 164 are expanded to contact the inner diameter 102 of the stent 100. The stent 100 is not expanded and maintains its nominal diameter when the second mandrel 354 is fully inserted within the slit cannula 300.

The second mandrel 354 also includes a handle 372. The handle 372 has a circular cross section, a first end 374, a second end 376, and a slot 378 that has a circular cross section for receiving the second portion 358 of the second mandrel 354. For example, when the diameter 362 of the second portion 358 is 0.1250±0.005 inches, the diameter of the slot 378 of the handle 372 is 0.1260±0.005 inches. The handle 372 slides onto the second portion 358 of the second mandrel 354 and is attached to the second mandrel 354 by a press fit and/or other fastening means that permit the handle 372 to be easily removed from the second mandrel 354. In an alternative example, the second mandrel 354 does not include a handle 372. In another example, the second portion 358 of the second mandrel 354 is knurled or machined to allow for gripping or handling of the second mandrel 354. The material of the handle 373 includes glass, metal, stainless steel or an alloy, and preferably stainless steel.

After expanding the slit cannula 300, the outer covering 172, including the first material 166 and the second material 168, as described previously, that is used for encapsulating the stent 100 or a prosthesis, is positioned over and wrapped around the stent 100 as shown in FIG. 36. The second material 168 is in contact with the stent 100, and the first material 166 is not in contact with the stent 100. As described previously, additional layers may also be added such that the first and second materials 166, 168 of the layers maintain an alternating pattern over the stent 100. To keep the layers in place, as previously described, a soldering iron may be used to tack or otherwise adhere edges of the layers.

As shown in FIG. 38, a second layer of elastomeric tube 380 is positioned in the tube expander 128. As described previously, the elastomeric material of the tube 380 may include the same material as the elastomeric tube 116. The elastomeric tube 380 is hollow and includes a circular cross section with an inner diameter 382, an outer diameter 384, a first end 386, a second end 388, and a longitudinal length 390. The longitudinal length 390 is defined from the first end 386 to the second end 388 of the elastomeric tube 380. The second layer of elastomeric tube 380 is positioned within the tube expander 128, as previously described, to uniformly expand the inner and outer diameters 382, 384 of the elastomeric tube 380. As previously described, the first and second ends 386, 388 of the elastomeric tube 380 may be may be rolled up over the first and second ends 138, 140 of the tube expander 128 to create a seal. The vacuum source 148 is applied to the tube expander 128 to uniformly expand the inner and outer diameters 382, 384 of the elastomeric tube 380.

A coating, as previously described, that reduces the friction on the surface of the second layer of elastomeric tube 380 may be applied to the inner diameter 382 of the second layer elastomeric tube 380. The coating helps to remove the stickiness or tackiness of the second layer elastomeric tube 380, so that the second layer elastomeric tube 380 does not stick to the outer covering 172.

As shown in FIG. 37, one or both of the handles 334, 372 may be removed from the second portions 325, 358 of the first and second mandrels 322, 354 in order to position the slit cannula 300 with the covered stent 174 and the first and second mandrels 322, 354 within the tube expander 128. The slit cannula 300 and the covered stent 174 are positioned with the tube expander 128 as shown in FIG. 38, and then the vacuum source 148 is released to allow the inner and outer diameters 382, 384 of the second layer of elastomeric tube 380 to return to an unexpanded state and recover to the covered stent 174. The second layer of elastomeric tube 380 and the covered stent 174 are removed from the tube expander 128 as shown in FIG. 39, and the handles 334, 372 may then be positioned back on the first and second mandrels 322, 354.

In one example, as described previously, after removal from the tube expander 128 and prior to applying pressure and heat, the first and second layers of elastomeric tube 342, 380, the covered stent 174, the slit cannula 300, and the first and second mandrels 322, 354 may be placed in a vacuum chamber for a pretreatment vacuum step. The pretreatment vacuum step may remove any air bubbles from the first and second layers of elastomeric tube 342, 380. Air bubbles within the first and second layers of elastomeric tube 342, 380 may affect heating and bonding of the inner and outer coverings 164, 172 to the stent 100. The vacuum chamber may be any vacuum chamber known in the art, and the first and second mandrels 322, 354 may be positioned on a rack in the vacuum chamber to provide uniform distribution of the pressure around the first and second layers of elastomeric tube 342, 380. In one example, the vacuum pressure applied may be approximately 500 to 700 mmHg (vacuum pressure) may be applied for approximately 15 minutes to two (2) hours. In another example, the vacuum pressure applied may be approximately 600 mmHg (absolute vacuum pressure) for approximately 1 hour. The vacuum pressure applied may vary and may range from approximately 50 mmHg to 760 mmHg (absolute vacuum pressure), and as the vacuum pressure applied increases, the time the vacuum pressure will be applied decreases.

As shown in FIGS. 40-42, the first and second layers of elastomeric tube 342, 380, the covered stent 174, the slit cannula 300, and the first and second mandrels 322, 354 are positioned in the press fixture 186 and then in the heated press 196, where heat and pressure are applied as previously described to create the smooth covered stent 198. Alternatively, heat and pressure may be applied as described in the "First and Second Tubes with Heated Oven" example, or other heat and pressure applications.

The first and second layers of elastomeric tube 342, 380, the smooth covered stent 198, the slit cannula 300, and the first and second mandrels 322, 354 are cooled, and then the handles 334, 372 may be removed from the first and second mandrels 322, 354 to position the second layer of elastomeric tube 380 and the smooth covered stent 198 in the tube expander 128 to remove the second layer of elastomeric tube 380 as shown in FIGS. 42-43. Other removal methods as described previously may also be used to remove the second layer of elastomeric tube 380 from the smooth covered stent 198. The handles 334, 372 are positioned backed on the first and second mandrels 322, 354 as shown in FIG. 44. As shown in FIG. 45, the second mandrel 354 is removed from the slit cannula 300, which decreases the outer diameter 304 of the slit cannula 300, and then the smooth covered stent 198 is removed from the slit cannula 300.

As shown in FIG. 46, the smooth covered stent 198 may include a plurality of stripes or indentations 392 on an inner surface 394 of the smooth covered stent 198 from compression against the slits 312 of the slit cannula 300. When the material of the first layer of elastomeric tube 342 includes an elastomeric material with a higher durometer than the material of the elastomeric tube 116, the stripes or indentations 392 may not form or are reduced in frequency.

As shown in FIGS. 47-49, to remove the strips 392 and to smooth the inner surface 394 of the smooth covered stent 198, a mandrel 396 with a diameter 398 is provided. The mandrel 396 includes a smooth outer surface 400, which may include glass or other suitable material with a smooth outer surface. The mandrel 396 is positioned within the smooth covered stent 198, and a first layer of elastomeric tube 402 with an inner diameter 404 and an outer diameter 406 is positioned over the smooth covered stent 198. The first layer of elastomeric tube 402 may include the same material as the elastomeric tube 116 previously described. The tube expander 128 may be used to uniformly expand the first layer of elastomeric tube 402 over the smooth covered stent 198. A coating, as previously described, that reduces the friction on the surface of the first layer of elastomeric tube 402 may be applied to the inner diameter 404 of the first layer of elastomeric tube 402 so that the first layer of elastomeric tube 402 does not stick to the smooth covered stent 198.

As shown in FIG. 49, a second layer of elastomeric tube 408 with an inner diameter 410 and an outer diameter 412 is positioned over the first layer of elastomeric tube 402. The second layer of elastomeric tube 408 may include the same material as the elastomeric tube 116 previously described. The inner and outer diameters 410, 412 of the second layer of elastomeric tube 408 are smaller than the inner and outer diameters 404, 406 of the first layer of elastomeric tube 402. To position the second layer of elastomeric tube 408 over the first layer of elastomeric tube 402, the tube expander 128 may be used to uniformly expand the second layer of elastomeric tube 408 over the first layer of elastomeric tube 402. A coating, as previously described, that reduces the friction on the surface of the second layer of elastomeric tube 408 may be applied to the inner diameter 410 of the second layer of elastomeric tube 408 so that the second layer of elastomeric tube 408 does not stick to the first layer of elastomeric tube 402.

The mandrel 396, the smooth covered stent 198, and the first and second layers of elastomeric tube 402, 408 are positioned in the press fixture 186 and then in the heated press 196, where heat and pressure are applied as previously described and as shown in FIGS. 40-41. The amount of heat applied and the time of heat application may vary, and in one example is 420 degrees Fahrenheit for two minutes. Alternatively, heat and pressure may be applied as described in the "First and Second Tubes with Heated Oven" example, or other heat and pressure applications.

After removal from the heated press 196, cooling, and removal from the press fixture 186, the second layer of elastomeric tube 408 is removed from the first layer of elastomeric tube 402, as shown in FIGS. 52 and 53. Any of the removal methods as described previously may be used to remove the second layer of elastomeric tube 408 from the first layer of elastomeric tube 402. A shrink tube 414 may be positioned over or wrapped around the first layer of elastomeric tube 402 and smooth covered stent 198. The material of the shrink tube 414 may include shrink silicone, polyimide shrink, shrink polyetheretherketone (PEEK), fluorinated ethylene propylene (FEP), polytetrafluoroethylene (PTFE), or polyethylene terephthalate (PET), and the shrink tube 414 includes a diameter 416. The diameter 416 of the shrink tube 414 is sufficient to be positioned over the first layer of elastomeric tube 402.

As shown in FIG. 54, a heating source 418, such as a heating gun, is applied to the shrink tube 414 to shrink the first layer of elastomeric tube 402 and apply compression and heat to the smooth covered stent 198. The amount of heat and the time of heat application may vary, and in one example, may be 215 degrees Celsius (or 420 degrees Fahrenheit) for five minutes when a shrink tube 414 comprising FEP is used. The shrink tube 414 is removed from the first layer of elastomeric tube 402, and then the first layer of elastomeric tube 402 is removed from the smooth covered stent 198 using any of the removal methods as described previously. The smooth covered stent 198 is then removed from the mandrel 396. As shown in FIGS. 55 and 56, the inner surface 394 of the smooth covered stent 198 is smooth and the stripes 392 are removed. In another example, the strips 392 may be removed from the inner surface 394 of the smooth covered stent 198 without use of the press fixture 186 and the heated press 196.

FIGS. 57-60 show another example of the slit cannula 300 when only a single mandrel 420 is used. The first ends 314 of the slits 300 all begin at the first end 306 of the slit cannula 300. FIG. 58 shows a cross sectional view of the first end 306 of the slit cannula 300.

The mandrel 420 includes a circular cross-section with a first portion 422 and a second portion 424. The first portion 422 includes a diameter 426, and the second portion 424 includes a diameter 428. The diameter 426 of the first portion 422 is greater than the diameter 428 of the second portion 424. The mandrel 420 includes a first end 430, a second end 432, a tip 434, and a longitudinal length 436, which is defined from the first end 430 to the second end 432 of the mandrel 420. The longitudinal length 436 of the mandrel 420 is smaller than the longitudinal length 310 of the slit cannula 300. In an alternative example, the mandrel 420 may be permanently fixed with the slit cannula to provide stability.

FIGS. 59 and 60 show the mandrel 420 within the slit cannula 300. In this example, the mandrel 420 is positioned within the slit cannula 300 after the first layer of elastomeric tube 342, the inner covering 164, and the stent 100 are positioned over the slit cannula 300. The steps as previously described can then be used to encapsulate the stent 100, including application of the outer covering 172 and the second layer of elastomeric tube 380 and the use of the press fixture 186 and the heated press 196 to apply pressure and heat.

FIGS. 61-64 show another example of the mandrel 420 including a plurality of splines 438. The number of splines 438 is the same as the number of slits 312 of the slit cannula 300. The mandrel 420 with the splines 438 helps to prevent the plurality of stripes or indentations 392 on the inner surface 394 of the smooth covered stent 198 from forming during compression. FIG. 64 shows a cross-sectional view of the mandrel 420 with the splines 438 when positioned within the slit cannula 300.

The tables and steps below provide examples of the materials and steps using the aforementioned method.

Example 3: Self-Expandable Stent, Slit Cannula and Two Mandrels with Handles

| Element | Specifications |
| --- | --- |
| Stent 100 | inner diameter 102 is 7.6 mm, outer diameter 104 is 8.0 mm, nominal diameter is 8 mm, longitudinal length 126 is 70 mm, self-expanding |
| Slit cannula 300 | inner diameter 302 is 3.76 mm, outer diameter 304 is 4.76 mm, longitudinal length is 210 mm, material is stainless steel |
| Slits 312 | number slits 312 is 10, longitudinal length 318 of slits is 208 mm |
| First mandrel 322 | longitudinal length 332 is 92 mm, diameter 324 is first portion 323 is 6.22 mm, diameter 327 of second portion 325 is 3.175 mm, material is stainless steel, |
| Handle 334 of first mandrel 322 | diameter of slot 340 is 3.20 mm, material is stainless steel |
| First layer of elastomeric tube 342 | material is silicone with a durometer of 50 Shore A, longitudinal length 352 is 210 mm, inner diameter 344 is 4.29 mm, outer diameter 346 is 5.31 mm |
| Coating | MED-6670, thickness is 45 μm |
| Inner covering 164 | includes first material 166 and second material 168 |
| First material 166 | ePTFE |
| Second material 168 | FEP |
| Second mandrel 354 | longitudinal length 370 is 144 mm, diameter 324 is first portion 356 is 6.22 mm, diameter 327 of second portion 358 is 3.175 mm, material is stainless steel, |
| Handle 372 of second mandrel 354 | diameter of slot 378 is 3.20 mm, material is stainless steel |

-continued

| Element | Specifications |
|---|---|
| Outer covering 172 | includes first material 166 and second material 168 |
| Second layer of elastomeric tube 380 | material is silicone with a durometer of 20 Shore A, longitudinal length 390 is 114 mm, inner diameter 382 is 6 mm, outer diameter 384 is 8 mm |
| Tube expander 128 | inner diameter 134 is 14 mm |
| Slot 192 of Press Fixture 186 | diameter 194 of slot 192 is 9.6 mm |

Steps:

The first mandrel 322 is positioned within the slit cannula 300;

The coating is applied to the outer diameter 346 of the first elastomeric tube 342 and then cured;

The first layer of elastomeric tube 342 is positioned over the slit cannula 300;

The inner covering 164 is rolled in 70% isopropanol;

The inner covering 164 is positioned over and wrapped around a non-expanded portion of the slit cannula 300 with the first material 166 of the inner covering 164 in contact with the first elastomeric tube 342;

The stent 100 is positioned over the inner covering 164 and in contact with the second material 168 of the inner covering 164;

The second mandrel 354 is positioned within the slit cannula 300 and radially expands the slit cannula 300, the first layer of elastomeric tube 342, and the inner covering 164 such that the inner covering 164 is in contact with the inner diameter 102 of the stent 100;

The outer covering 172 is rolled in 70% isopropanol;

The outer covering 172 is positioned over and wrapped around the stent 100 with the second material 168 in contact with the stent 100 to form the covered stent 174;

The coating is applied to the inner diameter 382 of the second layer of elastomeric tube 380 and then cured;

The second layer of elastomeric tube 380 is positioned within the tube expander 128 including the vacuum 148;

The first and second ends 306, 308 of the second layer of elastomeric tube 380 are rolled up and wrapped around the first and second ends 138, 140 of the tube expander 128;

The vacuum 148 is applied expanding the inner and outer diameters 382, 384 of second layer of elastomeric tube 380 until the outer diameter 384 of the second elastomeric tube 380 contacts the inner diameter 134 of the tube expander 128;

One of the handles 334, 372 is removed from either the first or second mandrel 322, 354;

The covered stent 174, the first layer of elastomeric tube 342, the slit cannula 300, and the first and second mandrels 322, 354 are positioned in the tube expander 128;

The vacuum 148 is released allowing the inner and outer diameters 382, 384 of second layer of elastomeric tube 380 to retract to an unexpanded state and recover to the covered stent 174;

The first and second layers of elastomeric tube 342, 380, the covered stent 174, the slit cannula 300, and the first and second mandrels 322, 354 are removed from the tube expander 128;

One of the handles 344, 372 previously removed is positioned back on either the first or second mandrel 322, 354;

The first and second layers of elastomeric tube 342, 380, the covered stent 174, the slit cannula 300, and the first and second mandrels 322, 354 are positioned in a vacuum chamber with an applied pressure of 600 mmHg (absolute vacuum pressure) for 1 hour;

The first and second layers of elastomeric tube 342, 380, the covered stent 174, the slit cannula 300, and the first and second mandrels 322, 354 are removed from the vacuum chamber and positioned in the slot 192 of the press fixture 186 and the first and second portions 188, 190 of the press fixture 186 are brought together;

The press fixture 186 is positioned in the heated press 196;

Pressure is applied to the press fixture 186 to displace the thickness of second layer of elastomeric tube 380 by 0.005±0.001 inches;

Heat is applied to the press fixture 186 to 500±5 degrees Fahrenheit and is applied for 1 minute time;

The press fixture 186 is removed from the heated press 196;

The first and second layers of elastomeric tube 342, 380, the smooth covered stent 198, the slit cannula 300, and the first and second mandrels 322, 354 are removed from the press fixture 186 and positioned in room temperature water for cooling;

One of the handles 334, 372 is removed from either the first or second mandrel 322, 354;

The first and second layers of elastomeric tube 342, 380, the smooth covered stent 198, the slit cannula 300, and the first and second mandrels 322, 354 are positioned in the tube expander 128;

The vacuum 148 is applied allowing the inner and outer diameters 382, 384 of second layer of elastomeric tube 380 to uniformly expand;

The smooth covered stent 198, the first layer of elastomeric tube 342, the slit cannula 300, and the first and second mandrels 322, 354 are removed from the tube expander 128;

One of the handles 344, 372 previously removed is positioned back on either the first or second mandrel 322, 354;

The second mandrel 354 is removed from the slit cannula 300; and

The smooth covered stent 198 is removed from the slit cannula 300.

Example 4: Self-Expandable Stent, Slit Cannula and Single Mandrel without Handle

| Element | Specifications |
|---|---|
| Stent 100 | inner diameter 102 is 7.6 mm, outer diameter 104 is 8.0 mm, nominal diameter is 8 mm, longitudinal length 126 is 70 mm, self-expandable |
| Slit cannula 300 | inner diameter 302 is 3.76 mm, outer diameter 304 is 4.76 mm, longitudinal length is 210 mm, material is stainless steel |
| Slits 312 | number slits 312 is 10, longitudinal length 318 of slits is 208 mm |
| Mandrel 420 | longitudinal length 436 is 236 mm, diameter 426 of first portion 422 is 6.22 mm, diameter 428 of second portion 424 is 3.175 mm, material is stainless steel |

-continued

| Element | Specifications |
|---|---|
| First layer of elastomeric tube 342 | material is silicone with a durometer of 50 Shore A, longitudinal length 352 is 210 mm, inner diameter 344 is 4.29 mm, outer diameter 346 is 5.31 mm |
| Coating | MED-6670, thickness is 45 μm |
| Inner covering 164 | includes first material 166 and second material 168 |
| First material 166 | esPTFE |
| Second material 168 | Polyurethane |
| Outer covering 172 | includes first material 166 and second material 168 |
| Second layer of elastomeric tube 380 | material is silicone with a durometer of 20 Shore A, longitudinal length 390 is 114 mm, inner diameter 382 is 6 mm, outer diameter 384 is 8 mm |
| Tube expander 128 | inner diameter 134 is 14 mm |
| Slot 192 of Press Fixture 186 | diameter 194 of slot 192 is 9.6 mm |

Steps:
The coating is applied to the outer diameter 346 of the first elastomeric tube 342 and then cured;
The first layer of elastomeric tube 342 is positioned over the slit cannula 300;
The inner covering 164 is rolled in 70% isopropanol;
The inner covering 164 is positioned over and wrapped around the slit cannula 300 with the first material 166 of the inner covering 164 in contact with the first elastomeric tube 342;
The stent 100 is positioned over the inner covering 164 and in contact with the second material 168 of the inner covering 164;
The mandrel 420 is positioned within the slit cannula 300 and radially expands the slit cannula 300, the first layer of elastomeric tube 342, and the inner covering 164 such that the inner covering 164 is in contact with the inner diameter 102 of the stent 100;
The outer covering 172 is rolled in 70% isopropanol;
The outer covering 172 is positioned over and wrapped around the stent 100 with the second material 168 in contact with the stent 100 to form the covered stent 174;
The coating is applied to the inner diameter 382 of the second layer of elastomeric tube 380 and then cured;
The second layer of elastomeric tube 380 is positioned within the tube expander 128 including the vacuum 148;
The first and second ends 306, 308 of the second layer of elastomeric tube 380 are rolled up and wrapped around the first and second ends 138, 140 of the tube expander 128;
The vacuum 148 is applied expanding the inner and outer diameters 382, 384 of second layer of elastomeric tube 380 until the outer diameter 384 of the second elastomeric tube 380 contacts the inner diameter 134 of the tube expander 128;
The covered stent 174, the first layer of elastomeric tube 342, the slit cannula 300, and the mandrel 420 are positioned in the tube expander 128;
The vacuum 148 is released allowing the inner and outer diameters 382, 384 of second layer of elastomeric tube 380 to retract to an unexpanded state and recover to the covered stent 174;
The first and second layers of elastomeric tube 342, 380, the covered stent 174, the slit cannula 300, and the mandrel 420 are removed from the tube expander 128;
The first and second layers of elastomeric tube 342, 380, the covered stent 174, the slit cannula 300, and the first and second mandrels 322, 354 are positioned in a vacuum chamber with an applied pressure of 600 mmHg (absolute vacuum pressure) for 1 hour;
The first and second layers of elastomeric tube 342, 380, the covered stent 174, the slit cannula 300, and the mandrel 420 are removed from the vacuum chamber and positioned in the slot 192 of the press fixture 186 and the first and second portions 188, 190 of the press fixture 186 are brought together;
The press fixture 186 is positioned in the heated press 196;
Pressure is applied to the press fixture 186 to displace the thickness of second layer of elastomeric tube 380 by 0.005±0.001 inches;
Heat is applied to the press fixture 186 to 390±5 degrees Fahrenheit and is applied for 1 minute time;
The press fixture 186 is removed from the heated press 196;
The first and second layers of elastomeric tube 342, 380, the smooth covered stent 198, the slit cannula 300, and the mandrel 420 are removed from the press fixture 186 and positioned in room temperature water for cooling;
The first and second layers of elastomeric tube 342, 380, the smooth covered stent 198, the slit cannula 300, and the mandrel 420 are positioned in the tube expander 128;
The vacuum 148 is applied allowing the inner and outer diameters 382, 384 of second layer of elastomeric tube 380 to uniformly expand;
The smooth covered stent 198, the first layer of elastomeric tube 342, the slit cannula 300, and the mandrel 420 are removed from the tube expander 128;
The mandrel 420 is removed from the slit cannula 300; and
The smooth covered stent 198 is removed from the slit cannula 300.

Applied Tension to Elastomeric Tube

In an alternative embodiment, when a self-expanding stent is used, tension may be applied to an elastomeric tube positioned on the mandrel rather than use of the slit cannula 300. For example, the first layer of elastomeric tube 342 is positioned within the tube expander 128 including the vacuum 148, and the first and second ends 348, 350 are rolled up and wrapped around the first and second ends 138, 140 of the tube expander 128. The vacuum 148 is applied expanding the inner and outer diameters 344, 346 of the first layer of elastomeric tube 342. The mandrel 150 is positioned in the tube expander 128, and the vacuum 148 is released allowing the inner and outer diameters 344, 346 of the first layer of elastomeric tube 342 to retract to an unexpanded state and recover to the mandrel 150. The outer diameter 346 of the first layer of elastomeric tube 342 on the mandrel 150 is then reduced by applying tension to the first layer of elastomeric tube 342 to allow the stent 100 to slide or otherwise be positioned over the first layer of elastomeric tube 342. Specifically, the tension applied outer diameter 346 of the first layer of elastomeric tube 342 is less than the inner diameter 102 of the stent 100. The tension may be applied by using clamps to pull on the first and second ends 348, 350 of the first layer of elastomeric tube 342.

With the tension applied to the first layer of elastomeric tube 342 on the mandrel 150, the inner covering 164 is positioned over and wrapped around the first layer of elastomeric tube 342 with the first material 166 of the inner covering 164 in contact with the first layer of elastomeric tube 342, as described previously. The stent 100, which in this example is a self-expanding stent, is positioned over the inner covering 164 and in contact with the second material 168 of the inner covering 164. After the stent 100 is positioned over the inner covering 164, the tension applied to the first layer of elastomeric tube 342 may be released and the clamps removed. When the tension is released, the first layer of elastomeric tube 342 expands to a non-tension applied state. After expansion, the inner covering 164 contacts the inner diameter 102 of the stent 100, and the stent 100 maintains its nominal diameter and is not significantly expanded. The subsequent steps described above to form the smooth covered stent 198 may then be applied, including without limitation the application of the outer covering 172, the application of the second layer of elastomeric tube 380, the application of heat and pressure using the press fixture 186 and heated press 196, may be used.

First and Second Tubes with Heated Oven

FIGS. 65-74 show another example of a method of making a stent with a smooth cover. FIG. 65 shows the covered stent 174 positioned over the mandrel 150 using the process steps as described previously. A first tube of elastomeric tube 500 is positioned in the tube expander 128. The first tube of elastomeric tube 500 may include the same material as the elastomeric tube 116 previously described. The first tube of elastomeric tube 500 includes an inner diameter 502, an outer diameter 504, a first end 506, a second end 508, and a longitudinal length 510, which is defined from the first end 506 to the second end 508. The longitudinal length 510 of the first tube 500 is longer than the longitudinal length of the covered stent 174 to completely cover the covered stent 174. In this example, the stent 100 is a balloon expandable stent. The inner diameter 502 of the elastomeric tube 500 may range from 2 mm to 15 mm. The outer diameter 504 of the elastomeric tube 500 may range from 3 mm to 21 mm.

A coating, as previously described, that reduces the friction on the surface of the first tube 500 may be applied to the inner diameter 502 of the first tube 500. The coating helps to remove the stickiness or tackiness of the first tube 500, so that the first tube 500 does not stick to the outer covering 172 of the covered stent 174.

As shown in FIG. 67, the first and second ends 506, 508 of the first tube 500 are wrapped around the first and second ends 138, 140 of the tube expander 128 to seal the first tube 500 to the tube expander 128, and then the vacuum 148 is applied to uniformly expand the inner and outer diameters 502, 504 of the first tube 500. The covered stent 174 and the mandrel 150 are then positioned in the tube expander 128 as shown in FIG. 68, and the vacuum source 148 is released to allow the first tube 500 to recover to the covered stent 100 as shown in FIG. 69. In its original state, the inner diameter 502 of the first tube 500 is smaller than the diameter 176 of the covered stent 100 and the mandrel 150.

A second tube 512 is provided as shown in FIG. 71. The second tube 512 may include the same material as the elastomeric tube 116 previously described, or the second tube 512 may include a shrink tube as previously described including shrink silicone, polyimide shrink, shrink polyetheretherketone (PEEK), fluorinated ethylene propylene (FEP), polytetrafluoroethylene (PTFE), or polyethylene terephthalate (PET). The material of the second tube 512 has a higher durometer than the material of the first tube 500. The second tube 512 includes an inner diameter 514, an outer diameter 516, a first end 518, a second end 520, and a longitudinal length 522, which is defined from the first end 518 to the second end 520. The inner diameter 514 of the second tube 512 may range from 2 mm to 17 mm. The outer diameter 516 of the second tube 512 may range from 3 mm to 23 mm.

The longitudinal length 522 is the same as or longer than the longitudinal length 510 of the first tube 500. The inner diameter 514 of the second tube 510 is smaller than the outer diameter 504 of the first tube 500 such that when the second tube 510 is applied to the first tube 500, the second tube 510 compresses the first tube 500 to the covered stent 174 and compresses the inner and outer coverings 164, 172 of the covered stent 174 sufficiently together to conform the outer covering 174 around the stent 100. When the second tube 512 is a shrink tube, the inner diameter 514 of the shrink tube 512 is initially larger than the outer diameter 504 of the first tube 500 to allow the second tube 512 to position over the first tube 500. The inner diameter 514 of the shrink tube 512 will decrease when heat is applied to apply compression.

When the second tube 512 includes an elastomeric tube, the second tube 512 is positioned in the tube expander to uniformly expand the inner and outer diameters 514, 516 of the second tube 512 as shown in FIGS. 71-73. The mandrel 150 with the covered stent 174 and the first tube 500 is then positioned in the tube expander 128, and the vacuum source 148 is released to allow the inner and outer diameters 514, 516 of the second tube 512 to return to an unexpanded state and recover to the first tube 500. As described previously, when the second tube 512 recovers to the first tube 500, the second tube 512 compresses the first tube 500 to the covered stent 174. FIG. 73 shows the mandrel 150 with the covered stent 174 and the first and second tubes 500, 512. When the second tube 512 includes a shrink tube, the second tube 512 is positioned over and wrapped around the first tube 500 and the tube expander 128 is not used. If the second tube 512 includes shrink tape rather than a shrink tube, the shrink tape may be wrapped around the first tube 500.

In one example, when the second tube 512 includes an elastomeric tube, prior to applying pressure and heat, the mandrel 150 with the covered stent 174 and the first and second tubes 500, 512 may be placed in a vacuum chamber for a pretreatment vacuum step. The pretreatment vacuum step may remove any air bubbles from the first and second tubes 500, 512. Air bubbles within the first and second tubes 500, 512 may affect heating and bonding of the inner and outer coverings 164, 172 to the stent 100. The vacuum chamber may be any vacuum chamber known in the art, and the mandrel 150 may be positioned on a rack in the vacuum chamber to provide uniform distribution of the pressure around the first and second tubes 500, 512. In one example, the vacuum pressure applied may be approximately 500 to 700 mmHg (vacuum pressure) may be applied for approximately 15 minutes to 2 hours. In another example, the vacuum pressure applied may be approximately 600 mmHg (absolute vacuum pressure) for approximately 1 hour. The vacuum pressure applied may vary and may range from approximately 50 mmHg to 760 mmHg (absolute vacuum pressure), and as the vacuum pressure applied increases, the time the vacuum pressure will be applied decreases.

As shown in FIG. 74, to melt the second material 168 of the inner and outer coverings 164, 172 of the covered stent 174, the mandrel 150 with the covered stent 174 and the first and second tubes 500, 512 are positioned in an oven 524 on an elevated rack 526 to apply uniform heat to the covered stent 174. The temperature applied may be the same as described previously for approximately 5 minutes. If the second tube 512 is a shrink tube, the temperature applied is above the recovery temperature of the shrink tube. The time will vary based on the melting temperature of the second material 168 or above the glass transition temperature of the first material 166 if the second material 168 is not used. Thus, the time period of heat application from range from 2 to 30 minutes.

After the heat is applied, the mandrel 150 with the smooth covered stent 198 and the first and second tubes 500, 512 are removed from the oven 524 and cooled. The first and second tubes 500, 512 may then be removed from the smooth covered stent 198 using any of the removal methods previously described, including use of the tube expander 128. The mandrel 150 is then removed from the smooth covered stent 198.

In another example, the aforementioned method may be used with a self-expanding stent. When a self-expanding stent is used, the slit cannula 300 is used with either the first and second mandrels 322, 354 previously described or the single mandrel 420 rather than the mandrel 150. In this example, the first and second tubes 500, 512 may be applied, as described above, to the covered stent 174, the slit cannula 300, and the first and second mandrels 322, 354 or the single mandrel 420. If the second tube 512 is elastomeric, the first and second mandrels 322, 354 or the single mandrel 420 and the slit cannula 300 with the covered stent 174 and the first and second tubes 500, 512 may be placed in a vacuum chamber for the pretreatment vacuum step. After removal from the vacuum chamber, heat may be applied as described above using the oven 524 and the first and second tubes 500, 512 may be removed from the smooth covered stent 198 using any of the removal methods previously described, including use of the tube expander 128. After the removal of the first and second tubes 500, 512, if the first and second mandrels 322, 354 are used, rather than the single mandrel 420, the smoother covered stent 198 may include the plurality of stripes or indentations 392 on the inner surface 394 of the smooth covered stent 198 from compression against the slits 312 of the slit cannula 300. The plurality of stripes or indentations 392 may be removed using the steps previously described above.

In an alternative example, as described previously above, if a self-expanding stent is used, tension may be applied to an additional elastomeric tube, or a third tube, positioned on the mandrel rather than use of the slit cannula 300. Specifically, the third tube may be positioned around the mandrel 150 via the tube expander 128 including the vacuum 148, as described previously above, prior to placement of the inner covering 164 over the mandrel 150. After placement of the third tube around the mandrel 150, tension is applied to the third tube to radially decrease the outer diameter of the third tube to allow the stent 100 to slide or otherwise be positioned over the third tube on the mandrel 150. Specifically, the tension applied outer diameter of the third tube is less than the inner diameter 102 of the stent 100. The tension may be applied by using clamps to pull on the ends of the second elastomeric tube.

With the tension applied to the third tube on the mandrel 150, the inner covering 164 is positioned over and wrapped around the third tube with the first material 166 of the inner covering 164 in contact with the third tube, as described previously. The stent 100 is positioned over the inner covering 164 and in contact with the second material 168 of the inner covering 164. After the stent 100 is positioned over the inner covering 164, the tension applied to the third tube may be released and the clamps removed. When the tension is released, the third tube radially expands to a non-tension applied state. After expansion, the inner covering 164 contacts the inner diameter 102 of the stent 100, and the stent 100 maintains its nominal diameter and is not significantly expanded. The subsequent steps described above to form the smooth covered stent 198 may then be applied, including without limitation the application of an outer covering 172, the application of the first and second tubes 500, 512, and the application of heat using the oven 524, may be used.

The tables and steps below provide examples of the materials and steps using the aforementioned method.

Example 5: Balloon-Expandable Stent, First and Second Tubes, and Inner and Outer Coverings with First and Second Materials

| Element | Specifications |
| --- | --- |
| Stent 100 | inner diameter 102 is 8.0 mm, outer diameter 104 is 8.4 mm, nominal diameter is 8 mm, longitudinal length 126 is 30 mm, balloon-expandable |
| Mandrel 150 | diameter is 8 mm, the material is stainless steel |
| First tube 500 | material is silicone with a durometer of 20 Shore A, longitudinal length 510 is 75 mm, inner diameter 502 is 6 mm, outer diameter 504 is 8 mm |
| Coating | MED-6670, thickness is 45 μm |
| Inner covering 164 | includes first material 166 and second material 168 |
| First material 166 | esPTFE |
| Second material 168 | Polyurethane |
| Outer covering 172 | includes first material 166 and second material 168 |
| Second tube 512 | material is silicone with a durometer of 25 Shore A, longitudinal length 522 is 75 mm, inner diameter 514 is 6 mm, outer diameter 516 is 8 mm |
| Tube expander 128 | inner diameter 134 is 14 mm |

Steps:

The inner covering 164 is rolled in 70% isopropanol;

The inner covering 164 is positioned over and wrapped around the mandrel 150 with the first material 166 of the inner covering 164 in contact with the mandrel 150;

The stent 100 is initially slightly over-expanded and then positioned over the inner covering 164 and in contact with the second material 168 of the inner covering 164;

An Iris crimper is used to secure the stent 100 to the inner covering 164;

The outer covering 172 is rolled in 70% isopropanol;

The outer covering 172 is positioned over and wrapped around the stent 100 with the second material 168 in contact with the stent 100 to form the covered stent 174;

The coating is applied to the inner diameter 502 of the first tube 500 and then cured;

The first tube 500 is positioned within the tube expander 128 including the vacuum 148;

The first and second ends 506, 508 of the first tube 500 are rolled up and wrapped around the first and second ends 138, 140 of the tube expander 128;

The vacuum 148 is applied expanding the inner and outer diameters 502, 504 of the first tube 500 until the outer diameter 504 of the first tube 500 contacts the inner diameter 134 of the tube expander 128;

The covered stent 174 and the mandrel 150 are positioned in the tube expander 128;

The vacuum 148 is released allowing the inner and outer diameters 502, 504 of the first tube 500 to retract to an unexpanded state and recover to the covered stent 174;

The first tube 500, the covered stent 174, and the mandrel 150 are removed from the tube expander 128;

The coating is applied to the inner diameter 514 of the second tube 512 and then cured;

The second tube 512 is positioned within the tube expander 128 including the vacuum 148;

The first and second ends 518, 520 of the second tube 512 are rolled up and wrapped around the first and second ends 138, 140 of the tube expander 128;

The vacuum 148 is applied expanding the inner and outer diameters 514, 516 of the second tube 512 until the outer diameter 516 of the second tube 512 contacts the inner diameter 134 of the tube expander 128;

The first tube 500, the covered stent 174, and the mandrel 150 are positioned in the tube expander 128;

The vacuum 148 is released allowing inner and outer diameters 514, 516 of the second tube 512 to retract to an unexpanded state and recover to the first tube 500 and the covered stent 174;

The first and second tubes 500, 512 the covered stent 174, and the mandrel 150 are removed from the tube expander 128;

The first and second tubes 500, 512, the covered stent 174, and the mandrel 150 are positioned in a vacuum chamber with an applied pressure of 600 mmHg (absolute vacuum pressure) for 1 hour;

The first and second tubes 500, 512, the covered stent 174, and the mandrel 150 are removed from the vacuum chamber and positioned on the rack 526 in the heated oven 524 and heated to 390±5 degrees Fahrenheit and is applied for 5 minutes time;

The first and second tubes 500, 512, the smooth covered stent 198, and the mandrel 150 are removed from the heated oven 524 and then compressed air or freeze spray is applied for cooling;

The first and second tubes 500, 512, the smooth covered stent 198, and the mandrel 150 are positioned in the tube expander 128;

The vacuum 148 is applied allowing the inner and outer diameters 514, 516 of the second tube 512 to expand away from the first tube 500;

The first tube 500, the smooth covered stent 198, and the mandrel 150 are removed from the tube expander 128;

The vacuum 148 is released allowing the inner and outer diameters 514, 516 of the second tube 512 to retract to an unexpanded state and the second tube 512 is removed from the tube expander 128;

The first tube 500, the smooth covered stent 198, and the mandrel 150 are positioned in the tube expander 128;

The vacuum 148 is applied allowing the inner and outer diameters 502, 504 of the first tube 500 to expand away from the smooth covered stent 198;

The smooth covered stent 198 and the mandrel 150 are removed from the tube expander 128; and The mandrel 150 is removed from the smooth covered stent 198.

Example 6: Balloon-Expandable Stent, First and Second Tubes, and Inner and Outer Coverings with First Material

| Element | Specifications |
| --- | --- |
| Stent 100 | inner diameter 102 is 8.0 mm, outer diameter 104 is 8.4 mm, nominal diameter is 8 mm, longitudinal length 126 is 30 mm, balloon-expandable |
| Mandrel 150 | diameter is 8 mm, the material is stainless steel |
| First tube 500 | material is silicone with a durometer of 20 Shore A, longitudinal length 510 is 75, inner diameter 502 is 6 mm, outer diameter 504 is 8 mm |
| Coating | MED-6670, thickness is 45 µm |
| Inner covering 164 | includes first material 166 |
| First material 166 | PET |
| Outer covering 172 | includes first material 166 |
| Second tube 512 | material is silicone with a durometer of 25 Shore A, longitudinal length 522 is 75 mm, inner diameter 514 is 6 mm, outer diameter 516 is 8 mm |
| Tube expander 128 | inner diameter 134 is 14 mm |

Steps:

The inner covering 164 is rolled in 70% isopropanol;

The inner covering 164 is positioned over and wrapped around the mandrel 150;

The stent 100 is initially slightly over-expanded and then positioned over the inner covering 164;

An Iris crimper is used to secure the stent 100 to the inner covering 164;

The outer covering 172 is rolled in 70% isopropanol;

The outer covering 172 is positioned over and wrapped around the stent 100 to form the covered stent 174;

The coating is applied to the inner diameter 502 of the first tube 500 and then cured;

The first tube 500 is positioned within the tube expander 128 including the vacuum 148;

The first and second ends 506, 508 of the first tube 500 are rolled up and wrapped around the first and second ends 138, 140 of the tube expander 128;

The vacuum 148 is applied expanding the inner and outer diameters 502, 504 of the first tube 500 until the outer diameter 504 of the first tube 500 contacts the inner diameter 134 of the tube expander 128;

The covered stent 174 and the mandrel 150 are positioned in the tube expander 128;

The vacuum 148 is released allowing the inner and outer diameters 502, 504 of the first tube 500 to retract to an unexpanded state and recover to the covered stent 174;

The first tube 500, the covered stent 174, and the mandrel 150 are removed from the tube expander 128;

The coating is applied to the inner diameter 514 of the second tube 512 and then cured;

The second tube 512 is positioned within the tube expander 128 including the vacuum 148;

The first and second ends 518, 520 of the second tube 512 are rolled up and wrapped around the first and second ends 138, 140 of the tube expander 128;

The vacuum 148 is applied uniformly expanding the inner and outer diameters 514, 516 of the second tube 512 until the outer diameter 516 of the second tube 512 contacts the inner diameter 134 of the tube expander 128;

The first tube 500, the covered stent 174, and the mandrel 150 are positioned in the tube expander 128;

The vacuum 148 is released allowing inner and outer diameters 514, 516 of the second tube 512 to retract to an unexpanded state and recover to the first tube 500 and the covered stent 174;

The first and second tubes 500, 512 the covered stent 174, and the mandrel 150 are removed from the tube expander 128;

The first and second tubes 500, 512, the covered stent 174, and the mandrel 150 are positioned in a vacuum chamber with an applied pressure of 600 mmHg (absolute vacuum pressure) for 1 hour;

The first and second tubes 500, 512, the covered stent 174, and the mandrel 150 are removed from the vacuum chamber and positioned on the rack 526 in the heated oven 524 and heated to 365±5 degrees Fahrenheit and is applied for 5 minutes time;

The first and second tubes 500, 512, the smooth covered stent 198, and the mandrel 150 are removed from the heated oven 524 and then compressed air or freeze spray is applied for cooling;

The first and second tubes 500, 512, the smooth covered stent 198, and the mandrel 150 are positioned in the tube expander 128;

The vacuum 148 is applied allowing the inner and outer diameters 514, 516 of the second tube 512 to expand away from the first tube 500;

The first tube 500, the smooth covered stent 198, and the mandrel 150 are removed from the tube expander 128;

The vacuum 148 is released allowing the inner and outer diameters 514, 516 of the second tube 512 to retract to an unexpanded state and the second tube 512 is removed from the tube expander 128;

The first tube 500, the smooth covered stent 198, and the mandrel 150 are positioned in the tube expander 128;

The vacuum 148 is applied allowing the inner and outer diameters 502, 504 of the first tube 500 to expand away from the smooth covered stent 198;

The smooth covered stent 198 and the mandrel 150 are removed from the tube expander 128; and The mandrel 150 is removed from the smooth covered stent 198.

Internal Pressure Application

Figure 77:
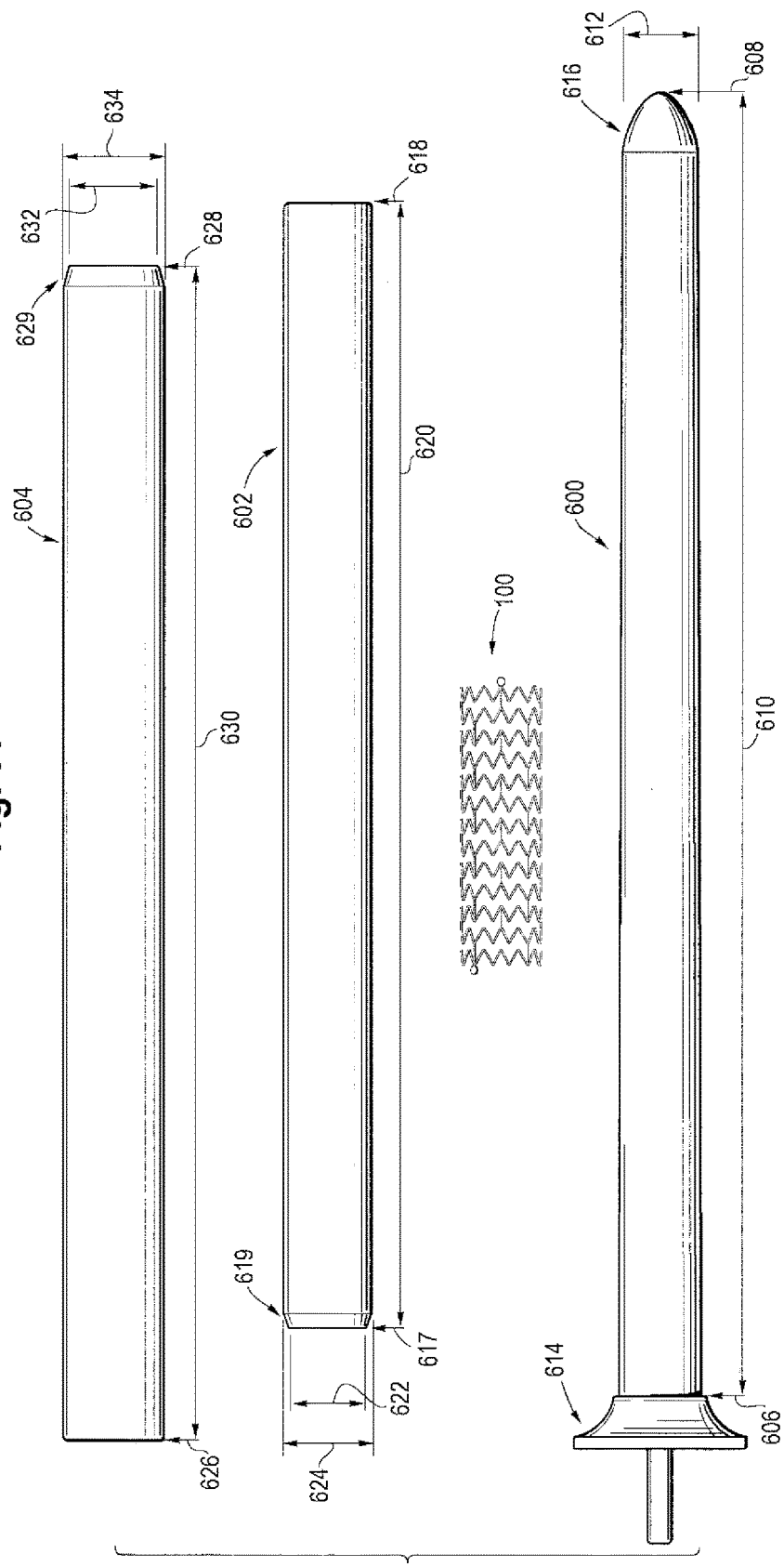
FIG. 77 shows a perspective view of a tapered rod, a first hollow mandrel, a second hollow mandrel, and a stent.

FIGS. 77-94 show another example of a method of making a stent with a smooth cover. FIG. 77 shows a tapered rod 600, a first hollow mandrel 602, a second hollow mandrel 604, and the stent 100, described previously above. In this example, the stent 100 is a self-expanding stent. As described in more detail below, the use of the tapered rod 600, the first hollow mandrel 602, and the second hollow mandrel 604 allow for gradual radial expansion of the inner and outer diameters 102, 104 of the stent 100. The tapered rod 600 includes a first end 606, a second end 608, a length 610 extending from the first end 606 to the second end 608, and a diameter 612. The diameter 612 of the tapered rod 610 is less than the inner and outer diameters 102, 104 of the stent 100. A handle 614 is positioned over or otherwise connected to the first end 606 of the tapered rod 600. The second end 608 of the tapered rod is a tapered end 616. The material of the tapered rod 600 and the handle 614 may include glass, metal, stainless steel, brass and/or an alloy.

The first hollow mandrel 602 includes a first end 617, a second end 618, a length 620 extending from the first end 617 to the second end 618, an inner diameter 622, and an outer diameter 624. The first end 617 of the first hollow mandrel 602 may include a tapered portion 619, as shown in FIG. 77. The inner diameter 622 of the first hollow mandrel 602 is greater than the diameter 612 of the tapered rod 600 such that the tapered rod 600 may be inserted into the first hollow mandrel 602.

The second hollow mandrel 604 includes a first end 626, a second end 628, a length 630 extending from the first end 626 to the second end 628, an inner diameter 632, and an outer diameter 634. The second end 628 of the second hollow mandrel 604 may include a tapered portion 629, as shown in FIG. 77. The inner diameter 632 of the second hollow mandrel 604 is greater than the outer diameter 624 of the first hollow mandrel 602 such that the first hollow mandrel 602 may be inserted into the second hollow mandrel 604. The material of the first hollow mandrel 602 and the second hollow mandrel 604 may include glass, metal, stainless steel, brass and/or an alloy. In an alternative embodiment, a hollow mandrel with a gradually expanding outer diameter along its length may be used rather than the first hollow mandrel 602 and the second hollow mandrel 604 to allow for gradual radial expansion of the stent 100.

Figure 78:
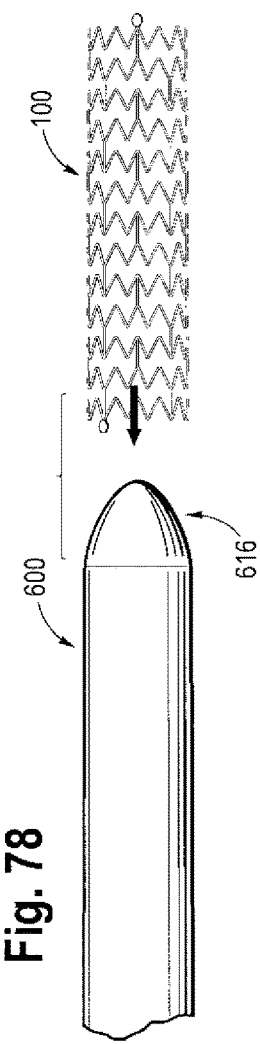
FIG. 78 shows a perspective view of positioning the stent on the tapered rod of FIG. 77.
Figure 79:
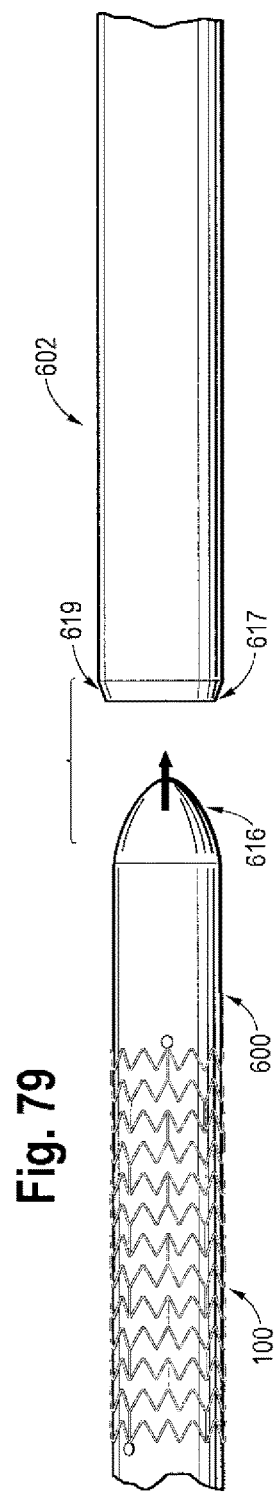
FIG. 79 shows a perspective view of positioning the tapered end of the tapered rod into the first hollow mandrel of FIG. 77.
Figure 80:
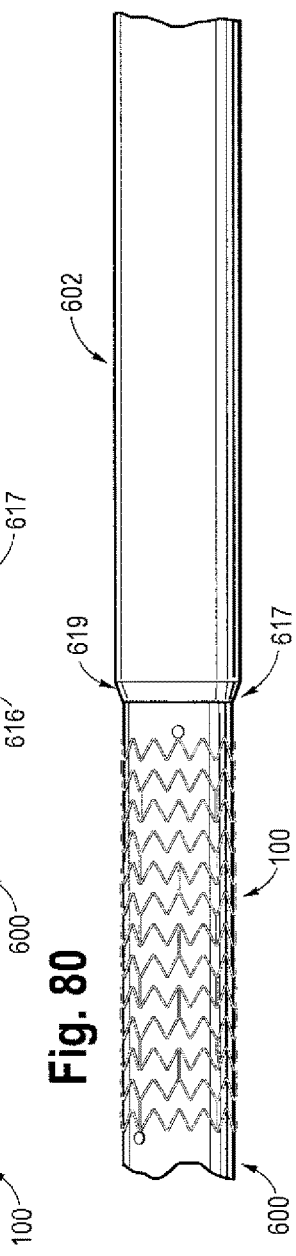
FIG. 80 shows a perspective view of the first hollow mandrel positioned over the tapered end of the tapered rod of FIG. 77.
Figure 81:
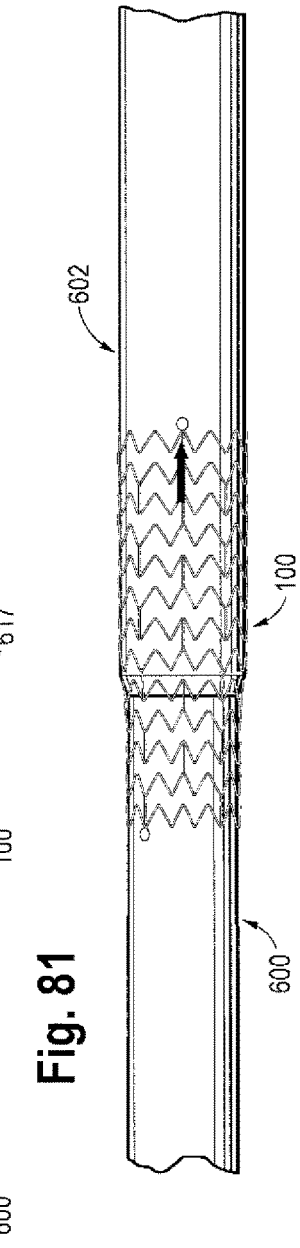
FIG. 81 shows a perspective view of sliding the stent along the tapered rod onto the first hollow mandrel of FIG. 77.

FIG. 78 shows the stent 100 to be positioned over the tapered end 616 and onto the tapered rod 600. As described previously, the diameter 612 of the tapered rod 600 is less than the inner and outer diameters 102, 104 of the stent 100 such that the stent 100 may slide onto the tapered rod 600 without the inner and outer diameters 102, 104 of the stent 100 significantly expanding. The tapered rod 600 with the stent 100 may be inserted into the first end 617 having the tapered portion 619 of the first hollow mandrel 602, as shown in FIG. 79. FIG. 80 shows that tapered end 616 of the tapered rod 600 positioned within the first hollow mandrel 602. As described previously, the diameter 612 of the tapered rod 600 is less than the inner diameter 622 of the first hollow mandrel 602 such that the tapered rod 600 may be inserted into the first hollow mandrel 602. The stent 100 may then slide along the tapered rod 600 and onto the first hollow mandrel 602, as shown in FIG. 81, which allows for gradual radial expansion of the stent 100. After the stent 100 is positioned over the first hollow mandrel 602, the tapered rod 600 is removed from the first hollow mandrel 602.

Figure 82:
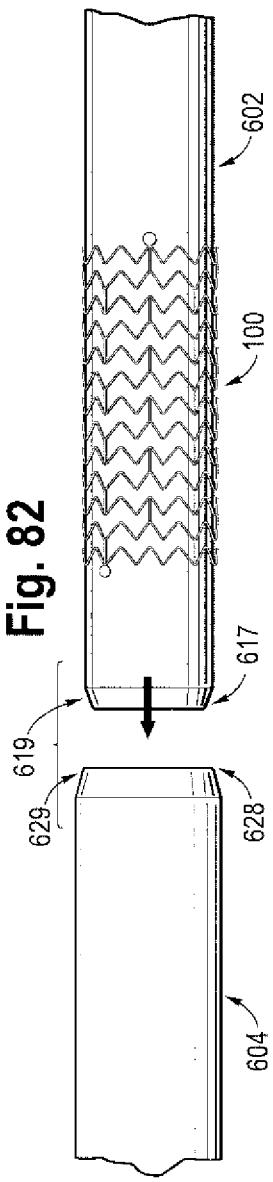
FIG. 82 shows a perspective of positioning the second hollow mandrel over the over an end of the first hollow mandrel of FIG. 77.
Figure 83:
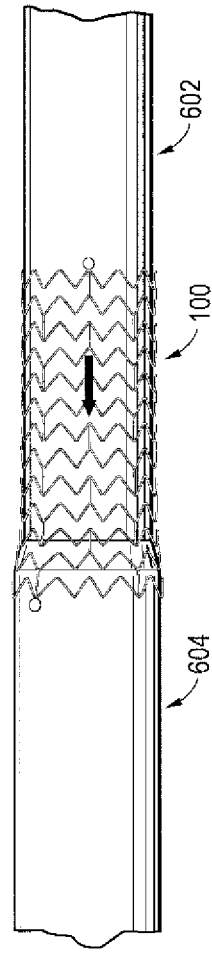
FIG. 83 shows a perspective view of the second hollow mandrel positioned over the end of the first hollow mandrel of FIG. 77 and sliding the stent along the first hollow mandrel onto the second hollow mandrel.
Figure 84:
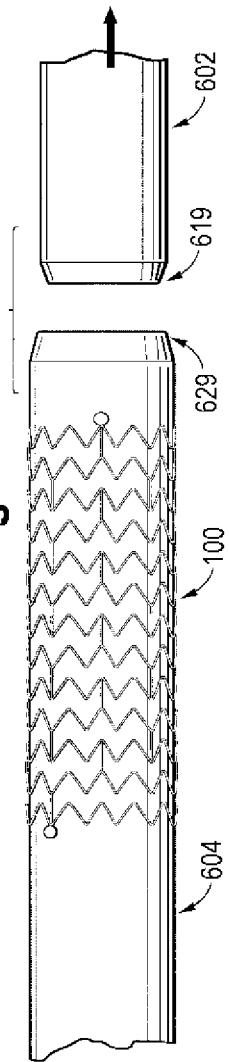
FIG. 84 shows a perspective view of the stent positioned on the second hollow mandrel of FIG. 77.

The first hollow mandrel 602 with the stent 100 may be inserted into the second end 628 having the tapered portion 629 of the second hollow mandrel 604, as shown in FIG. 82. As described previously, the outer diameter 624 of the first hollow mandrel 602 is less than the inner diameter 632 of the second hollow mandrel 604 such that the first hollow mandrel 602 may be inserted into the second hollow mandrel 604. The stent 100 may then slide along the first hollow mandrel 602 and onto the second hollow mandrel 604, as shown in FIG. 83, which allows for gradual radial expansion of the stent 100. After the stent 100 is positioned over the second hollow mandrel 604, the first hollow mandrel 602 may be removed from the second hollow mandrel 604, as shown in FIG. 84.

As shown in FIG. 85, the mandrel 150 with the first layer of elastomeric tube 342 positioned over the mandrel 150 and the inner covering 164 wrapped around the first layer of elastomeric tube 342 is provided. As described previously, the first layer of elastomeric tube 342 may include the same material as the elastomeric tube 116, and the coating may be applied to the outer diameter 346 of the first layer of elastomeric tube 342 to remove the stickiness or tackiness of the first layer of elastomeric tube 342 so that the first layer of elastomeric tube 342 does not stick to the inner covering 164. The first layer of elastomeric tube 342 may be positioned over the mandrel 150 using steps described previously.

Also, as previously described, the inner covering 164, including the first material 166 and the second material 168, is positioned over and wrapped around the first layer of elastomeric tube 342 such that the first material 166 is in contact with the first layer of the elastomeric tube 342. Additional layers may also be added such that the first and second materials 166, 168 of the layers maintain an alternating pattern over the stent 100, as described previously. To keep the layers in place, the soldering iron, described previously, may be used to tack or otherwise adhere edges of the inner covering 164. In an alternative embodiment, the mandrel 150 is not used and the inner covering 164 is wrapped around the first layer of elastomeric tube 342 without the mandrel 150 beneath the first layer of elastomeric tube.

The mandrel 150 with the first layer of elastomeric tube 342 and the inner covering 164 is positioned within the second hollow mandrel 604, as shown in FIG. 86. Once the second hollow mandrel 604 is positioned over the inner covering 164, the second hollow mandrel 604 is pulled away such that the stent 100 is positioned over the inner covering 164, as shown in FIG. 87, and the stent 100 recovers to its nominal diameter. When the stent 100 is positioned over the inner covering 164, the second material 168 of the inner covering 164 is in contact with the stent 100. The mandrel 150 may then be removed from the first layer of elastomeric tube 342 by pulling the mandrel 150 from beneath the first layer of elastomeric tube 342, as shown in FIG. 88.

In one example, freeze spray or liquid nitrogen may be applied to the stent 100 positioned on the second hollow mandrel 604 prior to removing the second hollow mandrel 604 from beneath the stent 100. The freeze spray or liquid nitrogen freezes the stent 100 in its expanded state, which facilitates positioning and placement of the stent 100 over the inner covering 164. When the stent 100 returns to room temperature, the stent 100 recovers to its nominal diameter and to the inner covering 164.

A support mandrel 636 is inserted into the first layer of elastomeric tube 342, as shown in FIG. 89. The support mandrel 636 includes a first end 638, a second end 640, a length 642 extending from the first end 638 to the second end 640, and an outer diameter 644 is shown in FIG. 89. The outer diameter 644 of the support mandrel 636 is less than the inner diameter 344 of the first layer of elastomeric tube 342 in an unexpanded state such that the support mandrel 636 may slide into the first layer of elastomeric tube 342. In this example, the support mandrel 636 is hollow and includes an inner diameter and a plurality of holes 646 along its length 642, as shown in FIG. 89. The plurality of holes 646 within the hollow support mandrel 636 allow for air, gas or hydraulic pressure to contact the first layer of elastomeric tube 342 and allow for expansion of the first layer of elastomeric tube 342. The support mandrel 636 provides support to the stent 100 during the pressurization and heating process. In alternative examples, the support mandrel may be solid and/or include supporting rib elements that extend along its length.

In another alternative example, the support mandrel 636 may be used rather than the mandrel 150 such that the first layer of elastomeric tube 342 is positioned over the support mandrel 636, the inner covering 164 is wrapped around the first layer of elastomeric tube 342, and the stent 100 is positioned over the inner covering 164, as described previously above. In this alternative example, the support mandrel 636 would not be removed prior to applying heat and pressure and would remain within the first layer of elastomeric tube 342 until after heat and pressure are applied, as described in more detail below.

The outer covering 172, including the first material 166 and the second material 168, is positioned over and wrapped around the stent 100 as described previously and as shown in FIG. 89 to form the covered stent 174. The second material 168 is in contact with the stent 100, and the first material 166 of the outer covering 172 is not in contact with the stent 100. As described previously, additional layers may also be added such that the first and second materials 166, 168 of the layers maintain an alternating pattern over the stent 100. To keep the layers in place, the soldering iron, described previously, may be used to tack or otherwise adhere edges of the outer covering 172.

The second layer of elastomeric tube 380, as described previously, is positioned over the covered stent 174 and the first layer of elastomeric tube 342 as shown in FIGS. 89-90. The inner diameter 382 of the second layer of elastomeric tube 380 is greater than the outer diameter 104 of the stent 100 with the outer covering 172 applied such that the second layer of elastomeric tube 380 may be positioned over the outer covering 172 and the stent 100. In an alternative embodiment, if the inner diameter 382 of the second layer of elastomeric tube 380 is smaller than or the same as the outer diameter 104 of the stent with the outer covering 172 applied, then the tube expander 128 may be used to radially expand the second layer of elastomeric tube 380 to be positioned over the outer covering 172 and the stent 100, as described previously. In one example, prior to applying pressure and heat, the pretreatment vacuum step may be used, including the vacuum chamber, to remove any air bubbles from the first and second layers of elastomeric tube 324, 380, as described previously.

As described previously, the second layer of elastomeric tube 380 may include the same material as the elastomeric tube 116, and the coating may be applied to the inner diameter 382 of the second layer of elastomeric tube 380 to remove the stickiness or tackiness of the second layer of elastomeric tube 380 so that the second layer of elastomeric tube 380 does not stick to the outer covering 172. In one example, the first layer of elastomeric tube 342 includes a durometer smaller than the durometer of the second layer of elastomeric tube 380. Specifically, the durometer of the first layer of elastomeric tube 342 may be 25 Shore A, and the durometer of the second layer of elastomeric tube 380 may be 30 Shore A. In an alternative example, the durometer of the first layer of elastomeric tube 342 is greater than the durometer of the second layer of elastomeric tube 380. Specifically, the durometer of the first layer of elastomeric tube 342 may be 50 Shore A, and the durometer of the second layer of elastomeric tube 380 may be 25 Shore A.

To apply pressure and heat to the first and second layers of elastomeric tube 324, 380 and the covered stent 174, a pair of barb fittings 648 are inserted into the first ends 348, 386 and the second ends 350, 388 of the first and second layers of elastomeric tube 324, 380, as shown in FIG. 91. The barb fittings 648 are barb fittings known in the art including hose barb fittings. A cap 650 is attached to the barb fitting 648 that is inserted into the first ends 348, 386 of the first and second layers of elastomeric tube 324, 380. The cap 650 acts as a plug to seal off the first ends 348, 386 of the second and second layers of elastomeric tube 324, 380. A tubing line 652 is attached to the barb fittings 648 that is inserted into the second ends 350, 388 of the first and second layers of elastomeric tube 324, 380, as shown in FIG. 91.

The tubing line 652 allows pressure, such as air, gas or hydraulic pressure, to enter into the first layer of elastomeric tube 324. A safety guard (not shown) may be positioned on the barb fittings 648 to secure the position of the barb fittings 648 to the first and second layers of elastomeric tube 324, 380.

Figure 94:
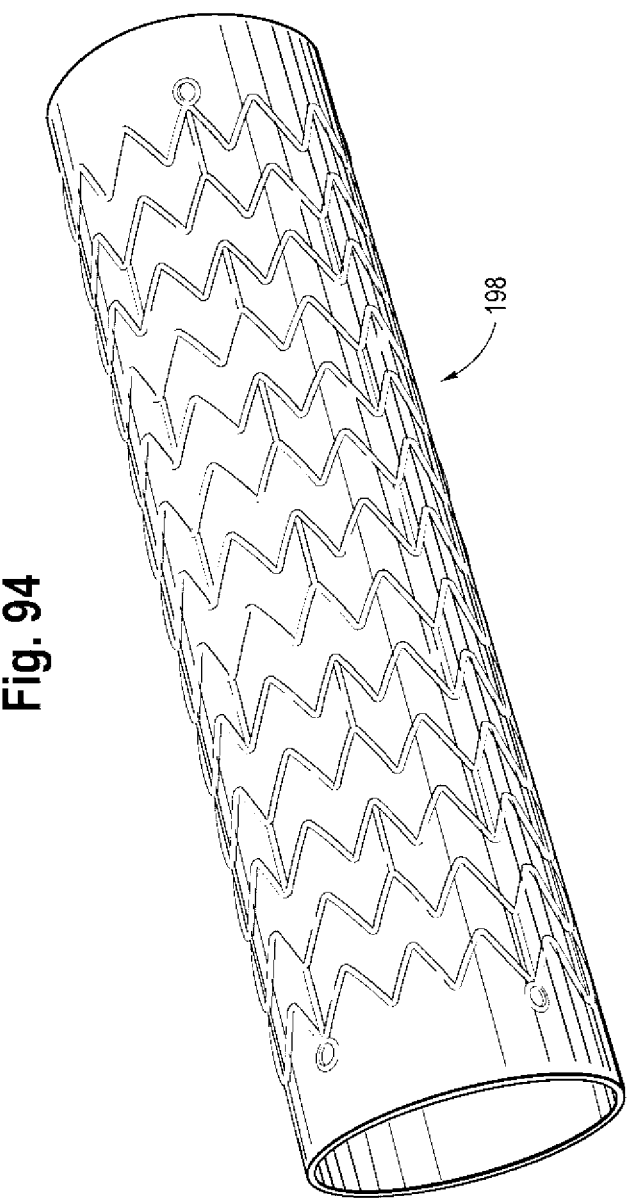
FIG. 94 shows a perspective view of a smooth covered stent.

The first and second layers of elastomeric tube 324, 380, the covered stent 174, the support mandrel 636, and the barb fittings 648 may be inserted into the slot 192 of the press fixture 186, as shown in FIG. 92. In this example, the outer diameter of the first and second layers of elastomeric tube 324, 380 and the covered stent 174 is less than the diameter 194 of the slot 192 such that there is space for the outer diameter of the first and second layers of elastomeric tube 324, 380 and the covered stent 174 to radially expand within the slot 192 when pressure is applied. After the press fixture 186 is closed, as shown in FIG. 93, the press fixture 186 may be positioned in the heated press 196, as described previously. Heat may be applied via the heated press 196, and pressure is applied via the tubing line 652 to apply pressure internally to the first layer of elastomeric tube 324. The internal pressure causes the first layer of elastomeric tube 324 to expand against the inner covering 164 toward the second layer of elastomeric tube 380. As described previously, the heat and pressure uniformly encapsulate and compress the inner and outer coverings 164, 172 and the stent 100 together to form the smooth covered stent 198, as shown in FIG. 94.

After removal from the heated press 196, cooling, and removal from the press fixture 186, the barb fittings 648, including the cap 650 and tubing line 652, are also removed from the first and second layers of elastomeric tube 324, 380 and the support mandrel 636 is also removed. The first and second layers of elastomeric tube 324, 380 are removed from the smooth covered stent 198 using any of the removal methods as described previously.

In an alternative example, when a self-expanding stent is used, tension may be applied to an elastomeric tube positioned on the mandrel rather than use of the tapered rod 600, the first hollow mandrel 602 and the second hollow mandrel 604. For example, the first layer of elastomeric tube 342 is positioned over the mandrel 150 via the tube expander 128 including the vacuum 148. The outer diameter 346 of the first layer of elastomeric tube 342 on the mandrel 150 is then reduced by applying tension to the first layer of elastomeric tube 342 to allow the stent 100 to slide or otherwise be positioned over the first layer of elastomeric tube 342. Specifically, the tension applied outer diameter 346 of the first layer of elastomeric tube 342 is less than the inner diameter 102 of the stent 100. The tension may be applied by using clamps to pull on the first and second ends 348, 350 of the first layer of elastomeric tube 342.

With the tension applied to the first layer of elastomeric tube 342 on the mandrel 150, the inner covering 164 is positioned over and wrapped around the first layer of elastomeric tube 342 with the first material 166 of the inner covering 164 in contact with the first layer of elastomeric tube 342, as described previously. The stent 100, which in this example is a self-expanding stent, is positioned over the inner covering 164 and in contact with the second material 168 of the inner covering 164. After the stent 100 is positioned over the inner covering 164, the tension applied to the first layer of elastomeric tube 342 may be released and the clamps removed. When the tension is released, the first layer of elastomeric tube 342 expands to a non-tension applied state. After expansion, the inner covering 164 contacts the inner diameter 102 of the stent 100, and the stent 100 maintains its nominal diameter and is not significantly expanded. The subsequent steps described above to form the smooth covered stent 198 may then be applied, including without limitation the removal of the mandrel 150, the positioning of the support mandrel 636 within the first layer of elastomeric tube 342, the positioning of the second layer of elastomeric tube 380, and the application of heat and internal pressure using the barb fittings 648, the cap 650, the tubing line 652, the press fixture 186, and the heated press 196, may be used.

The tables and steps below provide examples of the materials and steps using the aforementioned method.

Example 7: Self-Expanding Stent, First and Second Tubes, Inner and Outer Coverings with First and Second Materials, and Internal Pressurization

| Element | Specifications |
|---|---|
| Stent 100 | inner diameter 102 is 7.6 mm, outer diameter 104 is 8 mm, nominal diameter is 8 mm, longitudinal length 126 is 30 mm, self-expanding |
| Tapered Rod 600 | diameter 612 is 8.2 mm, material is stainless steel |
| First Hollow Mandrel 602 | outer diameter 624 is 9.5 mm, inner diameter 622 is 7.8 mm, material is brass |
| Second Hollow Mandrel 604 | outer diameter 634 is 10.3 mm, inner diameter 632 is 9.5 mm, material is brass |
| First layer of elastomeric tube 342 | material is silicone with a durometer of 25 Shore A, longitudinal length 352 is 5.25 inches, inner diameter 344 is 6 mm, outer diameter 346 is 8 mm |
| Coating | MED-6670, thickness is 45 μm |
| Inner covering 164 | includes first material 166 and second material 168 |
| First material 166 | esPTFE |
| Second material 168 | Polyurethane |
| Outer covering 172 | includes first material 166 and second material 168 |
| Second layer of elastomeric tube 380 | material is silicone with a durometer of 30 Shore A, longitudinal length 390 is 5.5 inches, inner diameter 382 is 6 mm, outer diameter 384 is 8 mm |
| Support mandrel 636 | length 642 is less than 30 mm, diameter 644 is 4.17 mm |
| Slot 192 of Press Fixture 186 | diameter 194 of slot 192 is 9.64 mm |

Steps:
 The coating is applied to the outer diameter 346 of the first elastomeric tube 342 and then cured;
 The first layer of elastomeric tube 342 is positioned over the mandrel 150;
 The inner covering 164 is rolled in 100% isopropanol;
 The inner covering 164 is positioned over and wrapped around the first elastomeric tube 342 with the first material 166 of the inner covering 164 in contact with the first elastomeric tube 342;
 The stent 100 is positioned on the tapered rod 600;
 The tapered end 616 of the tapered rod 600 is inserted into the first end 617 of the first hollow mandrel 602;
 The stent 100 is pushed along the tapered rod 600 onto the first hollow mandrel 602;
 The tapered rod 600 is removed from the first hollow mandrel 602;
 The first end 617 of the first hollow mandrel 602 is inserted into the second end 628 of the second hollow mandrel 604;

The stent 100 is pushed along the first hollow mandrel 602 onto the second hollow mandrel 604;

The first hollow mandrel 602 is removed from the second hollow mandrel 604;

The mandrel 150 with the first layer of elastomeric tube 342 and the inner covering 164 is inserted into the second end 628 of the second hollow mandrel 604 until the second hollow mandrel 604 is substantially covering the inner covering 164;

The stent 100 is held in place while the second hollow mandrel 604 is removed from beneath the stent 100 such that the stent 100 recovers to and is positioned over the inner covering 164 and in contact with the second material 168 of the inner covering 164;

The mandrel 150 is removed from the first layer of elastomeric tube 342;

The support mandrel 636 is inserted into the first layer of elastomeric tube 342;

The outer covering 172 is rolled in 100% isopropanol;

The outer covering 172 is positioned over and wrapped around the stent 100 with the second material 168 in contact with the stent 100 to form the covered stent 174;

The coating is applied to the inner diameter 382 of the second layer of elastomeric tube 380 and then cured;

The second layer of elastomeric tube 380 is positioned over the outer covering 172;

The first and second layers of elastomeric tube 342, 380, the covered stent 174, and the support mandrel 636 are positioned in a vacuum chamber with an applied pressure of 600 mmHg (absolute vacuum pressure) for one (1) hour;

The first and second layers of elastomeric tube 342, 380, the covered stent 174, and the support mandrel 636 are removed from the vacuum chamber;

The barb fittings 648 are inserted into the first ends 348, 386 and the second ends 350, 388 of the first and second layers of elastomeric tube 342, 380;

The cap 650 is connected to one of the barb fittings 648 and the tubing line 652 is connected to the other of the barb fittings 648;

The first and second layers of elastomeric tube 342, 380, the covered stent 174, the support mandrel 636, the barb fittings 648, the cap 650, and the tubing line 652 are positioned in the slot 192 of the press fixture 186 and the first and second portions 188, 190 of the press fixture 186 are brought together;

The press fixture 186 is positioned in the heated press 196;

Air pressure of approximately 35 PSI is applied to the tubing line 642 for approximately 1 minute;

Heat is applied to the press fixture 186 to 390±5 degrees Fahrenheit and is applied for 1 minute time;

The press fixture 186 is removed from the heated press 196;

The barb fittings 648 are removed from the first ends 348, 386 and the second ends 350, 388 of the first and second layers of elastomeric tube 342, 380;

The support mandrel 636 is removed from the first layer of elastomeric tube 342;

The first and second layers of elastomeric tube 342, 380 and the covered stent 174 are removed from the press fixture 186 and positioned in room temperature water for cooling; and The first and second layers of elastomeric tube 342, 380 are removed from the smooth covered stent 198.

Example 8: Self-Expanding Stent, First and Second Tubes, Inner and Outer Coverings with First and Second Materials, and Internal Pressurization

| Element | Specifications |
| --- | --- |
| Stent 100 | inner diameter 102 is 7.6 mm, outer diameter 104 is 8 mm, nominal diameter is 8 mm, longitudinal length 126 is 30 mm, self-expanding |
| Tapered Rod 600 | diameter 612 is 8.2 mm, material is stainless steel |
| First Hollow Mandrel 602 | outer diameter 624 is 9.5 mm, inner diameter 622 is 7.8 mm, material is brass |
| Second Hollow Mandrel 604 | outer diameter 634 is 10.3 mm, inner diameter 632 is 9.5 mm, material is brass |
| First layer of elastomeric tube 342 | material is silicone with a durometer of 50 Shore A, longitudinal length 352 is 5.25 inches, inner diameter 344 is 4.76 mm, outer diameter 346 is 7.94 mm |
| Coating | MED-6670, thickness is 45 μm |
| Inner covering 164 | includes first material 166 and second material 168 |
| First material 166 | esPTFE |
| Second material 168 | Polyurethane |
| Outer covering 172 | includes first material 166 and second material 168 |
| Second layer of elastomeric tube 380 | material is silicone with a durometer of 25 Shore A, longitudinal length 390 is 5.5 inches, inner diameter 382 is 6 mm, outer diameter 384 is 8 mm |
| Support mandrel 636 | length 642 is less than 30 mm, diameter 644 is 4.17 mm |
| Slot 192 of Press Fixture 186 | diameter 194 of slot 192 is 9.64 mm |

Steps:

The coating is applied to the outer diameter 346 of the first elastomeric tube 342 and then cured;

The first layer of elastomeric tube 342 is positioned over the mandrel 150;

The inner covering 164 is rolled in 70% isopropanol;

The inner covering 164 is positioned over and wrapped around the first elastomeric tube 342 with the first material 166 of the inner covering 164 in contact with the first elastomeric tube 342;

The stent 100 is positioned on the tapered rod 600;

The tapered end 616 of the tapered rod 600 is inserted into the first end 617 of the first hollow mandrel 602;

The stent 100 is pushed along the tapered rod 600 onto the first hollow mandrel 602;

The tapered rod 600 is removed from the first hollow mandrel 602;

The first end 617 of the first hollow mandrel 602 is inserted into the second end 628 of the second hollow mandrel 604;

The stent 100 is pushed along the first hollow mandrel 602 onto the second hollow mandrel 604;

The first hollow mandrel 602 is removed from the second hollow mandrel 604;

The mandrel 150 with the first layer of elastomeric tube 342 and the inner covering 164 is inserted into the second end 628 of the second hollow mandrel 604 until the second hollow mandrel 604 is substantially covering the inner covering 164;

The stent 100 is held in place while the second hollow mandrel 604 is removed from beneath the stent 100 such that the stent 100 recovers to and is positioned over the inner covering 164 and in contact with the second material 168 of the inner covering 164;

The mandrel 150 is removed from the first layer of elastomeric tube 342;

The support mandrel 636 is inserted into the first layer of elastomeric tube 342;

The outer covering 172 is rolled in 70% isopropanol;

The outer covering 172 is positioned over and wrapped around the stent 100 with the second material 168 in contact with the stent 100 to form the covered stent 174;

The coating is applied to the inner diameter 382 of the second layer of elastomeric tube 380 and then cured;

The second layer of elastomeric tube 380 is positioned over the outer covering 172;

The first and second layers of elastomeric tube 342, 380, the covered stent 174, and the support mandrel 636 are positioned in a vacuum chamber with an applied pressure of 600 mmHg (absolute vacuum pressure) for one (1) hour;

The first and second layers of elastomeric tube 342, 380, the covered stent 174, and the support mandrel 636 are removed from the vacuum chamber;

The barb fittings 648 are inserted into the first ends 348, 386 and the second ends 350, 388 of the first and second layers of elastomeric tube 342, 380;

The cap 650 is connected to one of the barb fittings 648 and the tubing line 652 is connected to the other of the barb fittings 648;

The first and second layers of elastomeric tube 342, 380, the covered stent 174, the support mandrel 636, the barb fittings 648, the cap 650, and the tubing line 652 are positioned in the slot 192 of the press fixture 186 and the first and second portions 188, 190 of the press fixture 186 are brought together;

The press fixture 186 is positioned in the heated press 196;

Air pressure of approximately 35 PSI is applied to the tubing line 642 for approximately 5 minutes;

Heat is applied to the press fixture 186 to 390±5 degrees Fahrenheit and is applied for 5 minutes;

The press fixture 186 is removed from the heated press 196;

The barb fittings 648 are removed from the first ends 348, 386 and the second ends 350, 388 of the first and second layers of elastomeric tube 342, 380;

The support mandrel 636 is removed from the first layer of elastomeric tube 342;

The first and second layers of elastomeric tube 342, 380 and the covered stent 174 are removed from the press fixture 186 and positioned in room temperature water for cooling; and The first and second layers of elastomeric tube 342, 380 are removed from the smooth covered stent 198.

It will be appreciated by those skilled in the art that changes could be made to the examples described above without departing from the broad inventive conceptive therefor. For example, heat and pressure application steps of one example may be used with the expansion and removal steps of the elastomeric tube 116 of a different example to encapsulate the stent 100 with a smooth covering. It is understood, therefore, that this invention is not limited to the particular examples disclosed, but it is intended to cover modifications within the spirit and scope of the present invention as defined by the appended claims.

We claim:

1. A method of making a stent with a smooth covering, said method comprising:

positioning an elastomeric tube comprising an inner diameter and an outer diameter and first and second ends in a tube expander having first and second ends and comprising a vacuum;

wrapping the first and second ends of the elastomeric tube around the first and second ends of the tube expander;

expanding the inner diameter and the outer diameter of the elastomeric tube by applying the vacuum;

positioning an inner covering over a mandrel;

positioning a stent over the inner covering;

positioning an outer covering over the stent to form a covered stent;

positioning the mandrel and the covered stent in the tube expander;

releasing the vacuum;

removing the elastomeric tube, the covered stent, and the mandrel from the tube expander;

applying pressure and heat to the elastomeric tube, the covered stent, and the mandrel;

removing the elastomeric tube, the covered stent, and the mandrel from the pressure and the heat;

removing the elastomeric tube from the covered stent; and removing the mandrel from the covered stent.

2. The method of claim 1, wherein the inner covering comprises a first material and a second material, and the outer covering comprises the first material and the second material.

3. The method of claim 2, wherein the second material of the inner covering contacts the second material of the outer covering, and the second material of the inner covering and the second material of the outer covering contacts the stent.

4. The method of claim 1, wherein applying the pressure comprises positioning the elastomeric tube, the covered stent, and the mandrel in a press fixture comprising a slot to receive the elastomeric tube, the covered stent, and the mandrel and applying compression to the press fixture.

5. The method of claim 4, wherein applying the heat comprises positioning the press fixture in a heated press.

6. The method of claim 1, wherein the elastomeric tube comprises silicone comprising a durometer of 20 Shore A.

7. The method of claim 6, the method further comprising applying a coating to the elastomeric tube.

8. The method of claim 1, wherein the stent comprises a balloon-expandable stent.

9. The method of claim 1, wherein the stent comprises a nominal diameter and maintains the nominal diameter during the steps of the method of claim 1.

10. A method of making a stent with a smooth covering, said method comprising:

positioning a first elastomeric tube having first and second ends over a slit cannula comprising an inner diameter, an outer diameter, and a plurality of slits;

positioning an inner covering over the first elastomeric tube;

positioning a stent over the first elastomeric tube;

positioning a stent over the first elastomeric tube;

positioning a mandrel having an outer diameter within the slit cannula to expand the first elastomeric tube and the inner covering;

positioning an outer covering over the stent to form a covered stent;

positioning a second elastomeric tube having first and second ends and comprising an inner diameter and an outer diameter in a tube expander comprising a vacuum, wherein the outer diameter of the mandrel is greater than the inner diameter of at least one of the slit cannula;

wrapping the first and second ends of one of the first and second elastomeric tubes around the first and second ends of the tube expander;

applying the vacuum to the tube expander to expand the inner diameter and the outer diameter of the second elastomeric tube;

positioning the covered stent, the first elastomeric tube, the slit cannula, and the mandrel in the tube expander;

releasing the vacuum;

removing the first and second elastomeric tubes, the covered stent, the slit cannula, and the mandrel from the tube expander;

applying pressure and heat to the first and second elastomeric tubes, the covered stent, the slit cannula, and the mandrel;

removing the first and second elastomeric tubes, the covered stent, the slit cannula, and the mandrel from the pressure and the heat;

removing the second elastomeric tube from the covered stent;

removing the mandrel from the slit cannula; and removing the covered stent from the first elastomeric tube and the slit cannula.

11. The method of claim 10, wherein the inner covering comprises a first material and a second material, and the outer covering comprises the first material and the second material.

12. The method of claim 10, wherein the mandrel comprises a handle.

13. The method of claim 10, wherein the stent comprises a balloon-expandable stent.

14. The method of claim 13, the method further comprising applying a coating to the first and second elastomeric tubes.

15. The method of claim 10, wherein the stent comprises a self-expanding stent.

16. The method of claim 10, wherein the stent comprises a nominal diameter and maintains the nominal diameter during the steps of the method of claim 10.

17. The method of claim 10, wherein applying the pressure comprises positioning the first and second elastomeric tubes, the covered stent, the slit cannula, and the mandrel in a press fixture comprising a slot to receive the first and second elastomeric tubes, the covered stent, the slit cannula, and the mandrel and applying compression to the press fixture.

18. The method of claim 10, wherein the mandrel comprises a plurality of splines.

19. A method of making a prosthesis with a smooth covering, said method comprising:

positioning an inner covering over a mandrel;

positioning a prosthesis over the inner covering;

positioning an outer covering over the prosthesis to form a covered prosthesis;

positioning a first tube having first and second ends and comprising an inner diameter and an outer diameter in a tube expander having first and second ends comprising a vacuum;

wrapping the first and second ends of the tube around the first and second ends of the tube expander;

applying the vacuum to the tube expander and expanding the inner and outer diameters of the first tube;

positioning the covered prosthesis and the mandrel in the tube expander;

releasing the vacuum from the tube expander;

removing the first tube, the covered prosthesis, and the mandrel from the tube expander;

positioning a second tube over the first tube, wherein the second tube comprises an inner diameter and an outer diameter, and wherein the inner diameter of the second tube is smaller than the inner diameter of the first tube;

applying heat to the first and second tubes, the covered prosthesis, and the mandrel;

removing the first and second tubes, the covered prosthesis, and the mandrel from the heat;

removing the second tube from the first tube, the covered prosthesis, and the mandrel;

removing the first tube from the covered prosthesis and the mandrel; and removing the mandrel from the covered prosthesis.

* * * * *